US010588968B2

(12) United States Patent
Lu et al.

(10) Patent No.: US 10,588,968 B2
(45) Date of Patent: Mar. 17, 2020

(54) HUMAN ANTI-VEGFR-2/KDR ANTIBODIES

(71) Applicant: KADMON CORPORATION, LLC, New York, NY (US)

(72) Inventors: Dan Lu, Montvale, NJ (US); Zhenping Zhu, Woodcliff Lake, NJ (US)

(73) Assignee: KADMON CORPORATION, LLC, New York, NY (US)

( * ) Notice: Subject to any disclaimer, the term of this patent is extended or adjusted under 35 U.S.C. 154(b) by 0 days.

(21) Appl. No.: 15/517,778

(22) PCT Filed: Oct. 7, 2015

(86) PCT No.: PCT/US2015/054569
§ 371 (c)(1),
(2) Date: Apr. 7, 2017

(87) PCT Pub. No.: WO2016/057726
PCT Pub. Date: Apr. 14, 2016

(65) Prior Publication Data
US 2018/0250392 A1    Sep. 6, 2018

Related U.S. Application Data

(60) Provisional application No. 62/061,097, filed on Oct. 7, 2014.

(51) Int. Cl.
*A61K 39/395* (2006.01)
*C07K 16/28* (2006.01)
*C07K 16/30* (2006.01)
*A61P 35/00* (2006.01)

(52) U.S. Cl.
CPC .......... *A61K 39/3955* (2013.01); *A61P 35/00* (2018.01); *C07K 16/2863* (2013.01); *C07K 2317/33* (2013.01); *C07K 2317/76* (2013.01); *C07K 2317/92* (2013.01)

(58) Field of Classification Search
CPC ............ C07K 2317/33; C07K 2317/76; C07K 2317/92; C07K 16/2863; A61K 39/3955
See application file for complete search history.

(56) References Cited

U.S. PATENT DOCUMENTS

| | | | |
|---|---|---|---|
| 2005/0147612 A1* | 7/2005 | Yayon ................ | C07K 16/2863 424/146.1 |
| 2012/0316071 A1 | 12/2012 | Smider et al. | |
| 2013/0011409 A1* | 1/2013 | Shipp .................... | C07K 16/18 424/156.1 |
| 2016/0237095 A1* | 8/2016 | Kim ..................... | C07D 401/14 |

FOREIGN PATENT DOCUMENTS

| | | |
|---|---|---|
| WO | 2013/149219 A2 | 10/2013 |
| WO | 2014/055996 A2 | 4/2014 |
| WO | 2014/055998 A1 | 4/2014 |
| WO | 2014/055999 A2 | 4/2014 |
| WO | 2015/054317 A1 | 4/2015 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*

* cited by examiner

*Primary Examiner* — Hong Sang
(74) *Attorney, Agent, or Firm* — Fox Rothschild LLP

(57) ABSTRACT

The invention relates to antibodies that bind to VEGFR-2. The antibodies are used for treating neoplastic diseases, hyperproliferative disorders, and angiogenic disorders and can be used alone or in combination with other agents.

13 Claims, 19 Drawing Sheets

Specification includes a Sequence Listing.

| Kabat No. | | 1 2 3 4 5 6 7 8 9 | 1 0 1 2 3 4 5 | 6 7 8 9 | 1 2 3 4 5 A B | 6 7 8 9 | 4 0 1 2 3 |
|---|---|---|---|---|---|---|---|
| SEQ ID NO. | 4 | E V Q L L E S G G | G L V Q P G G | S L R L S C A A S | G F T F S W Y V M G – – | W V R Q A P G K |
| | 12 | E V Q L L E S G G | G L V Q P G G | S L R L S C A A S | G F T F S W Y I M L – – | W V R Q A P G K |

| Kabat No. | | 4 5 6 7 8 9 | 5 0 1 2 A B C 3 4 5 | 6 6 7 8 9 0 1 2 3 4 5 | 6 7 8 9 | 7 0 1 2 3 4 5 | 6 7 8 9 | 8 0 1 2 A B C |
|---|---|---|---|---|---|---|---|---|
| SEQ ID NO. | 4 | G L E W V S | S I Y P – – S G G A T N | Y A D S V K G | R F T I S R D N S K N T L Y L Q M N S L |
| | 12 | G L E W V S | S I G S – – S G G F T D | Y A D S V K G | R F T I S R D N S K N T L Y L Q M N S L |

| Kabat No. | | 8 9 | 9 0 1 2 3 4 | 5 6 7 8 9 0 A B C D E F G H I J K 1 2 | 3 4 5 | 6 7 8 9 | 1 0 0 1 2 3 |
|---|---|---|---|---|---|---|---|
| SEQ ID NO. | 4 | R A E D T A V Y Y C A R | G N Y F – – – – – – – – – – – D Y | W G Q G T L V T V S S |
| | 12 | R A E D T A V Y Y C A R | G L A A P – – – – – – – – – – R S | W G R G T L V T V S S |

```
Kabat                      1111111111222 2222 27      3333334   333
No.        123456789012345678901234 567ABCDEF01234   567

SEQ
ID NO.
  8    QSVLTQDPA-VSVALGQTVRIHTC  QGDSL------RSYYAS    WYQ
 24    QSALTQPPS-VSVSPGQTASIHTC  SGDKL------GDEYAS    WYQ
 28    QYELTQPPS-VSVSPGQTASIHTC  SGDNL------RHEYAS    WYQ
 32    QSVLTQPPS-VSVSPGQTASIHTC  SGEKL------GDEYAS    WYQ
 36    QSELTQPPS-VSVSPGQTATIHTC  SGDKL------GDQFAS    WYQ
 40    QYELTQPPS-VSVSPGQTAAIHTC  SGDKL------GERSAS    WYQ
 44    QSALTQPPS-VSVSPGQTAAIHTC  TGDAL------GNNYAS    WYQ
 48    QSALTQPPS-VSVSPGHTARVHTC  SGQIL-----HIGNNAVI   WYQ
 16    QSALTQPAS-VSASGTPGQRVTIHSC SSSSN----HIGNNAVI   WYK
 20    QSELTQPPS-VEAPGTPGQRVTIHSC SSSSN----HIGTYPVN   WYQ
 52    QSALTQPPS-VSGTPGQRVTIHSC  SSSSN-----HIGTNTLN   WYQ
 56    QSELTQPDS-VASGTPGQRVTIHSC SSSSN-----HIGNNAVI   WYQ
 60    QSALTQPPS-VSGSPGQSSIHSC   SSSSN------IESNYYVS  WYQ
 64    QSALTQPDS-VSGSPGQSSIHSC   SSSSN-----HIGSYDYVS  WYQ
 68    QSELTQPAS-VSGSPGRSSIHSC   SSSND-----HVGAYDYVS  WYK
 72    QSALTQPDS-VMSGSPGQSSIHSC  TGSSN-----HIGSYDYVS  WYK
 76    QSVLTQPAS-VSGSPGQSSIHSC   AGTSS-----DIGAYDYVS  WYK
 80    QSVLTQPYS-VSGSPGQSSIHSC   TGSSH-----DIGAYDYVS  WYK
 84    QSALTQPAS-VSGSPGQSSIHSC   TGSSH-----DIGAYDYVS  WYK
 88    QSELTQPDS-VSGSPGQSSIHSC   TGSSH-----DIGAYDYVS  WYK
 92    QSVLTQPDS-VSGSPGQSSIHSC   TGSSH-----DIGAYDYVS  WYK
 96    QSELTQPDS-VSGSPGQSSIHSC   TGSSH-----DIGAYDYVS  WYK
```

Fig. 1B2

| Kabat No. | | | | | | | | | | 89 | 90 | 1 | 2 | 3 | 4 | 5 ABCDEF | 6 | 7 | 8 | 9 | 100 | 1 | 2 | 3 | 4 | 5 | 6 | 7A | 8 | 9 | P |
|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | | | | | | | | | | | | | | | | | | | | | | | |
| SEQ ID NO: | | | | | | | | | | | | | | | | | | | | | | | | | | | | | | | |
| 8 | M | D | E | A | D | Y | Y | C | Q | A | W | D | S | N | T | | A | V | F | G | G | G | T | K | L | T | V | L | G | Q | P |
| 24 | M | D | E | A | D | Y | Y | C | Q | A | W | D | S | S | T | | V | V | F | G | G | G | T | K | L | T | V | L | G | Q | P |
| 28 | L | D | E | A | D | Y | Y | C | Q | A | W | G | S | S | T | | V | V | F | G | G | G | T | K | V | T | V | L | R | Q | P |
| 32 | M | D | E | A | D | Y | Y | C | Q | A | W | D | S | S | T | | L | L | F | G | G | G | T | K | L | T | V | L | G | Q | P |
| 36 | M | D | E | A | D | Y | Y | C | Q | A | W | D | F | S | S | | L | L | F | G | G | G | T | K | L | T | V | L | G | Q | P |
| 40 | I | D | E | A | H | Y | Y | C | Q | A | W | D | T | S | | | A | L | F | G | A | G | T | K | V | T | V | L | G | Q | P |
| 44 | M | D | E | A | D | Y | Y | C | Q | T | W | D | R | N | T | P | I | Y | F | G | G | G | T | K | L | T | V | L | G | Q | P |
| 48 | M | D | E | A | D | Y | Y | C | Q | T | W | D | D | N | L | N G | Y | P | F | G | G | G | T | K | L | T | V | L | R | Q | P |
| 16 | E | D | E | A | D | Y | Y | C | A | S | W | D | S | S | T | | V | V | F | G | G | G | T | K | L | T | V | L | G | Q | P |
| 20 | M | D | E | A | D | Y | Y | C | Q | A | W | D | D | S | L | H G | P | V | F | G | G | G | T | K | R | T | V | L | S | Q | P |
| 52 | D | D | E | A | D | Y | Y | C | A | S | W | D | D | N | L | N G | P | L | F | G | G | G | T | K | L | T | V | L | G | Q | P |
| 56 | E | D | E | A | D | Y | Y | C | A | A | W | D | D | S | L | S G | W | V | F | G | G | G | T | K | L | T | V | L | R | Q | P |
| 60 | E | D | E | A | D | Y | Y | C | A | S | W | D | S | L | T | A | V | L | F | G | G | G | T | R | R | T | V | L | S | Q | P |
| 64 | D | D | E | A | D | Y | F | C | M | S | Y | T | T | T | T | | L | L | F | G | T | G | T | R | V | T | V | L | G | Q | P |
| 68 | D | D | E | A | D | Y | F | C | M | S | Y | T | T | T | T | | L | L | F | G | T | G | T | R | V | T | V | L | S | Q | P |
| 72 | D | D | E | A | D | Y | F | C | M | S | Y | T | T | T | T | | L | L | F | G | T | G | T | R | V | T | V | L | S | Q | P |
| 76 | D | D | E | A | D | Y | F | C | M | S | Y | T | T | T | T | | L | L | F | G | T | G | T | R | V | T | V | L | S | Q | P |
| 80 | D | D | E | A | D | Y | F | C | M | S | Y | T | T | T | T | | L | L | F | G | T | G | T | R | V | T | V | L | S | Q | P |
| 84 | D | D | E | A | D | Y | F | C | M | S | Y | T | T | T | T | | L | L | F | G | T | G | T | R | V | T | V | L | S | Q | P |
| 88 | D | D | E | A | D | Y | F | C | M | S | Y | T | T | T | T | | L | L | F | G | T | G | T | R | V | T | V | L | S | Q | P |
| 92 | D | D | E | A | D | Y | F | C | M | S | Y | T | T | T | T | | L | L | F | G | T | G | T | R | V | T | V | L | S | Q | P |
| 96 | D | D | E | A | D | Y | F | C | M | S | Y | T | T | T | T | | L | L | F | G | T | G | T | R | V | T | V | L | S | Q | P |

Fig. 1B3

| Kabat No. | 1-23 (Framework) | 24-27, 27A-F, 28-34 (CDR-L1) | 35-37 |
|---|---|---|---|
| SEQ ID NO: | 1234567890123456789 0123 | 4567ABCDEF8901234 | 567 |
| 100 | DIQMTQSPSTLSLSPGERATLSC | RASQS     VSSSYLA | WYQ |
| 104 | DIQMTQSPSTLSVLSPGERATLSC | RASER    HISSNYLM | WFQ |
| 108 | DIQMTQSPATLSLSPGERATLSC | RASQS     ISSNYLA | WYQ |
| 112 | DIQMTQSPATLSLSPGERATLSC | RASQSI   RSSGYLS | WYQ |
| 116 | DIQMTQSPSTLSLSPGERATLSC | RASQS     VSSNYLG | WYQ |
| 120 | DIQMTQSPSTLSLSPGERATLSC | RASQS     VSSSYLA | WYQ |
| 124 | DIQMTQSPSTLSLSPGERATLSC | RASQS     VSSSYLA | WYQ |
| 128 | DIQMTQSPSTLSLSPGERATLSC | RASQS     VGSSYLA | WYQ |
| 132 | DIQMTQSPSTLSLSPGERATLSC | RASQN     VSSSYLA | WYQ |
| 136 | DIQMTQSPSTLSLSPGERATLSC | RASQS     VSSSYLA | WYQ |
| 140 | DIQMTQSPSTLSLSPGERATLSC | RASQS     VSSNYLA | WYQ |
| 144 | DIQMTQSPSTLSLSPGERATLSC | RASQS     VSSSYFG | WYQ |
| 148 | DIQMTQSPSTLSLSPGERATLSC | RASQS     VSSNYLA | WYQ |
| 152 | DIQMTQSPSTLSLSPGDRATLSC | RASQS     LNNNYLA | WYQ |
| 156 | DIQMTQSPSTLSLSPGERATLSC | RASQS     VSSDYLA | WYQ |
| 160 | DIQMTQSPATLSVSPGERATLSC | RASHS     VSSDYLA | WYQ |
| 164 | DIQMTQSPDTLSLSPGERATLSC | RASHS     VSSDYLA | WYQ |
| 168 | DIQMTQSPDTLSLSPGERATLSC | RASHS     VSSDYLA | WYQ |

| Kabat No. | 48-49 | 40s/50s | CDR-L2 (50-56) | FR3 region |
|---|---|---|---|---|

| SEQ ID NO: | Sequence |
|---|---|
| 100 | QKPGQAPPRLLMY GASSRAT GFPDPDRFSGSGSGTDFSLTHSRLEP |
| 104 | QRPGQAPPRLLMY GASIRAT GIPDPDRFSGESGTDFTLTHSRVEP |
| 108 | QRPGQAPPRLLIY GASSRST GTPAPDRFSGSGSGTDFTLTHSRLES |
| 112 | QKPGQAPPRLLIY GASTRAT GIHPDRFSGSGSGTDFSLTHSRLEP |
| 116 | QKPGQAPPRLLIY GASSRAT GIHPDRFSGSGSGTDFTLTHSRLEP |
| 120 | QKPGQAPPRLLIY GASSRAT GIHPARFSGSGSGTDFTLTHSRLEP |
| 124 | QKPGQAPPRLLIY GASSRAT GIHPDDRFSGSGSGTDFTLTHSRLEP |
| 128 | QKPGQAPPRLLMY GASSRAT GFPDPDRFSGSGSGTDFSLTHSRLEP |
| 132 | QKPGRAPPRLLMY GASSRAT GIHPDDRFSGSGSGTDFTLTHSRLEP |
| 136 | QKPGQAPPRLLIY GASSRAT GIHPDDRFSGSGSGTDFTLTHSRLEP |
| 140 | QKPGQAPPRLLIY GASNRAT GIHPDDRFSGSGSGTDYTLTHNSRLEQ |
| 144 | QKPGQAPPRLLMY GASSRAT GIHPDDRFSGSGSGTEDFTLTHSRLEP |
| 148 | QKPGQAPPRLLIY GASSRAT GIHPDDRFSGSGSGTDFFTLTHSRLEP |
| 152 | QKPGQAPPRLLIY GASSRAT GFPDPDRFTGSGSGTDFSLTHSRLEP |
| 156 | QKPGRAPPRVLMY GASTRAT GIHPDDRFSGSGSGTDFSLTHSRVSP |
| 160 | QKPGRAPPRLLIY GASSRAT GIHPDDRFSGSGSGTDFSLTHSRLEQ |
| 164 | QKPGRAPPRLLMY GASSRAT GFPDPDRFSGSGSGTDFTLTHSRLEP |
| 168 | QKPGQAPPRLLMY GASSRAT GFPDPARFSGSGSGTDFSLTHSRLEP |
| 172 | QKPGQAPPRLLMY GASSRAT GFPDPDRFSGSGSGTDFSSTHSRLEP |
| 176 | QKPGRAPPRLLMY GASSRAT GFPDPDRFSGSGSGTDFSSTHSRLEP |
| 180 | QKPGRAPPRLLMY GASSRAT GFPDPDRFSGSGSGTDFSSTHSRLEP |
| 184 | QKPGRAPPRLLMY GASSRAT GFPDPDRFSGSGSGTDFSSTHSRLEP |

| Kabat No. | 1 2 3 4 5 6 7 8 | 9 0 1 2 3 4 5 A B C D E F 6 7 | 8 9 0 1 2 3 4 5 6 7 8 |
|---|---|---|---|
| SEQ ID NO: | | | |
| 100 | E D F A V Y Y C | Q Q F D S S P . . . . . . P T | F G G G T K V E I K R |
| 104 | E D F A V Y Y C | Q Q Y Y S S P L . . . . . L T | F G G G T K V E M K R |
| 108 | E D F A I Y F C | Q Q F D T L P . . . . . . H T | F G G G T K V D I K R |
| 112 | E D F A V Y Y C | Q Q Y G S T . . . . . . . H V | H G G Q G T K V E M D I K R |
| 116 | E D F A V Y Y C | Q Q F D N L P . . . . . . L T | F G G G T K V E I K R |
| 120 | E D F A V Y Y C | Q Q F D T S P . . . . . . L S | F G G G T K V D V D I K R |
| 124 | E D S A V Y Y C | Q Q F D S S P . . . . . . L T | F G G G T K V E I K R |
| 128 | E D S A V Y Y C | Q Q F D S S P . . . . . . P T | F G G G T K V E I K R |
| 132 | E D F A V Y Y C | Q Q F D S S P . . . . . . P T | F G G G T K V E I K R |
| 136 | E D S A V Y Y C | Q Q F D S S P . . . . . . Y T | F G G G T K V K L E I K R |
| 140 | E D F A I H Y C | Q Q F G S S P P . . . . . W T | F G G G T K V E I K R |
| 144 | E D F A V Y Y C | Q Q F D S N P P . . . . . L T | F G G G T K V V E I K R |
| 148 | E D S A V Y Y C | Q Q F D S S P . . . . . . L S | F G G G T K V V E I K R |
| 152 | E D F A M Y Y C | Q Q F D S S P . . . . . . P T | F G G G T K V V E I K R |
| 156 | E D F A M Y Y C | Q Q F D S S P . . . . . . P T | F G G G T K V V E I K R |
| 160 | E D S A V Y Y C | Q Q F D S S P . . . . . . P T | F G G G T K V V E I K R |
| 164 | E D F A V Y Y C | Q Q F D S S P . . . . . . P T | F G G G T K V V E I K R |
| 168 | E D F A V Y Y C | Q Q F D S S P . . . . . . P T | F G G G T K V V E I K R |
| 172 | E D F A V Y Y C | Q Q F D S S P . . . . . . P T | F G G G T K V V E I K R |
| 176 | E D F A V Y Y C | Q Q F D S S P . . . . . . P T | F G G G T K V V E I K R |
| 180 | E D F A V Y Y C | Q Q F D S S P . . . . . . P T | F G G G T K V V E I K R |
| 184 | E D F A V Y Y C | Q Q F D S S P . . . . . . P T | F G G G T K V R I D I K R |

Fig. 1C3

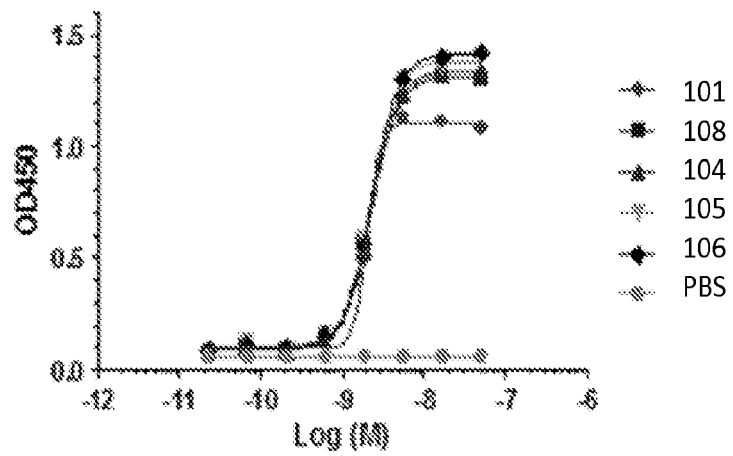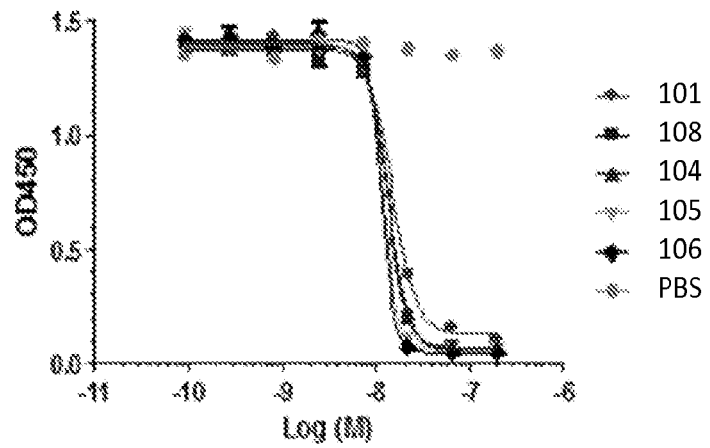
Fig. 4

A)
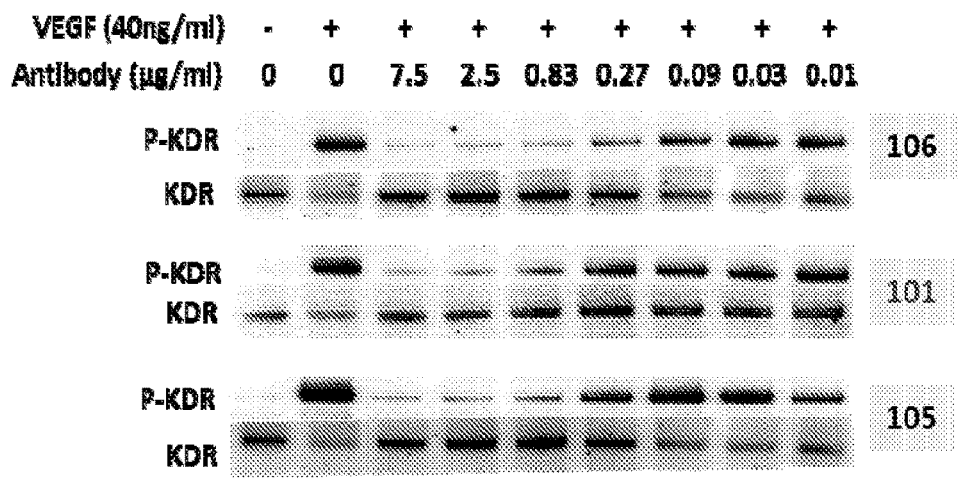
B)
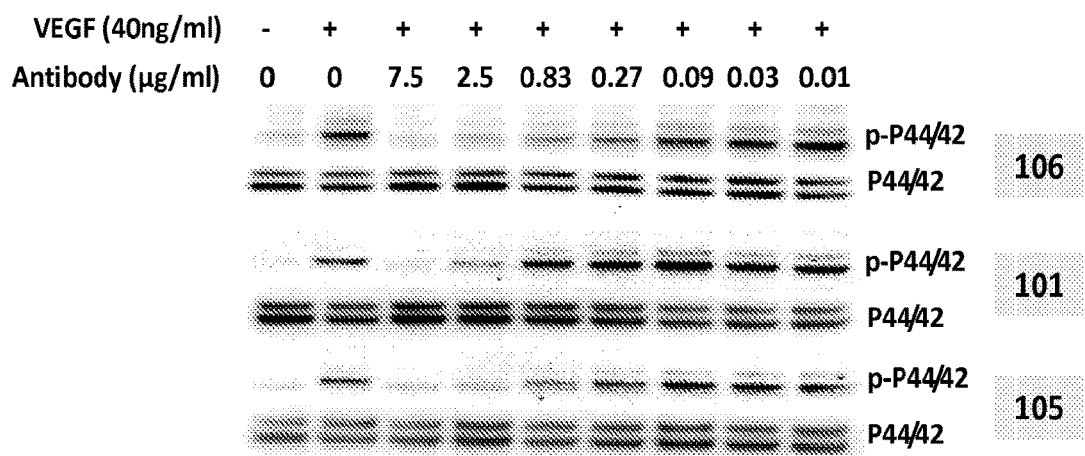
C)
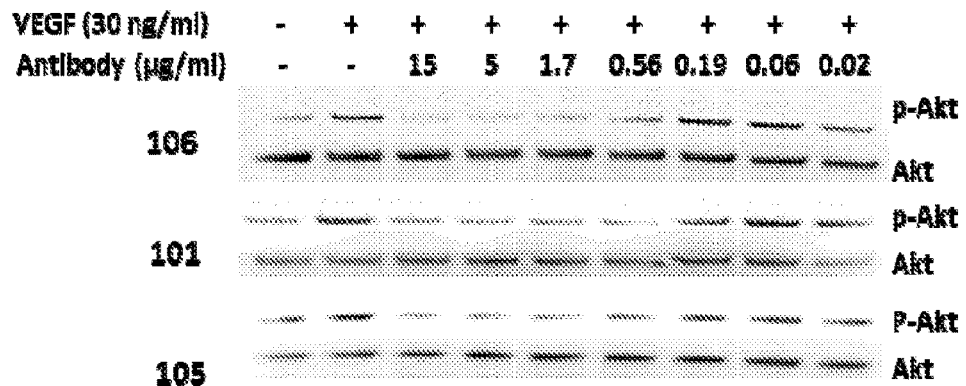
Fig. 5

| Kabat No. | 1 2 3 4 5 6 7 8 9 | 1 0 | 1 2 3 4 5 6 7 8 9 | 2 0 1 2 3 4 5 | 3 6 7 8 9 0 1 2 3 4 5 A B | 4 6 7 8 9 0 1 2 3 |
|---|---|---|---|---|---|---|
| SEQ ID NO. 4 | E V Q L L E S | G G G L V Q P G | G S L R L S C A A S | G F T F S W Y V M G – | W V R Q A P G K |
| 200 | E V Q L L E S | G G G L V Q P G | G S L R L S C A A S | G F T F S W Y V M G – | W V R Q A P G K |
| 208 | E V Q L L E S | G G G L V Q P G | G S L R L S C A A S | G F T F S W Y V M S – | W V R Q A P G K |
| 216 | E V Q L L E S | G G G L V Q P G | G S L R L S C A A S | G F T F S W Y V M G – | W V R Q A P G K |
| 224 | E V Q L L E S | G G G L V Q P G | G S L R L S C A A S | G F T F S W Y V M G – | W V R Q A P G K |
| 232 | E V Q L L E S | G G G L V Q P G | G S L R L S C A A S | G F T F S W Y V M G – | W V R Q A P G K |

| Kabat No. | 4 5 6 7 8 9 | 5 0 1 2 A B C 3 4 5 | 6 6 7 8 9 0 1 2 3 4 5 | 7 6 7 8 9 0 1 2 3 4 5 | 8 6 7 8 9 0 1 2 A B C |
|---|---|---|---|---|---|
| SEQ ID NO. 4 | G L E W V S | S I Y P – – S G G A T N Y A D S V K G | R F T T I S R D N S K N T L Y L Q M N S L |
| 200 | G L E W V S | S I Y P – – Q G G A T S Y A D S V K G | R F T T I S R D N S K N T L Y L Q M N S L |
| 208 | G L E W V S | S I Y P – – Q G G A T N Y A D S V K G | R F T T I S R D N S K N T L Y L Q M N S L |
| 216 | G L E W V S | S I Y P – – S G G A T N Y A D S V K G | R F T T I S R D N S K N T L Y L Q M N S L |
| 224 | G L E W V S | S I Y P – – S G G A T N Y A D S V K G | R F T T I S R D N S K N T L Y L Q M N S L |
| 232 | G L E W V S | S I Y P – – S G G A T N Y A D S V K G | R F T T I S R D N S K N T L Y L Q M N S L |

| Kabat No. | 3 4 5 6 7 8 9 | 9 0 1 2 3 | 1 0 0 A B C D E F G H I J K | 1 2 | 3 4 5 6 7 8 9 0 1 2 3 |
|---|---|---|---|---|---|
| SEQ ID NO. 4 | R A E D T A | V Y Y C A R | G N Y F – – – – – – – – – – – – | D Y | W G Q G T L V T V S S |
| 200 | R A E D T A | V Y Y C A R | G N Y F – – – – – – – – – – – – | D Y | W G Q G T L V T V S S |
| 208 | R A E D T A | V Y Y C A R | G N Y F – – – – – – – – – – – – | D Y | W G Q G T L V T V S S |
| 216 | R A E D T A | V Y Y C A R | G N Y L – – – – – – – – – – – – | D Y | W G Q G T L V T V S S |
| 224 | R A E D T A | V Y Y C A R | G P Y L – – – – – – – – – – – – | D Y | W G Q G T L V T V S S |
| 232 | R A E D T A | V Y Y C A R | G S Y L – – – – – – – – – – – – | D Y | W G Q G T L V T V S S |

Fig. 6A

```
Kabat                            1                   2            3
 No.          1 2 3 4 5 6 7 8 9 0 1 2 3 4 5 6 7 8 9 0 1 2 3 4 5 6 7 A B C D E F 8 9 0 1 2 3 4 5 6 7
SEQ ID NO:
    160       D I Q M T Q S P G T L S L S P G E G A T L S C R A S Q S           V S S N Y F G W Y Q
    204       D I Q M T Q S P G T L S L S P G E G A T L S C R A S Q S           V S S N Y F G W Y Q
    212       D I Q M T Q S P G T L S L S P G E G A T L S C R A S Q S           V S S N Y F G W Y Q
    220       D I Q M T Q S P G T L S L S P G E G A T L S C R A S Q S           V S S N Y F G W Y Q
    228       D I Q M T Q S P G T L S L S P G E G A T L S C R A S Q S           V S S N Y F G W Y Q
    236       D I Q M T Q S P G T L S L S P G E G A T L S C R A S Q S           V S S N Y F G W Y Q Kabat                 4                   5                   6                   7               8
 No.          8 9 0 1 2 3 4 5 6 7 8 9 0 1 2 3 4 5 6 7 8 9 0 1 2 3 4 5 6 7 8 9 0 1 2 3 4 5 6 7 8 9 0
SEQ ID NO:
    160       Q K P G Q A P R R L L I Y G A S S R A T G I P D R F S G S G S G T D F T L T I S R L E P
    204       Q K P G Q A P R R L L I Y G A S S R A T G I P D R F S G S G S G T D F T L T I S R L E P
    212       Q K P G Q A P R R L L I Y G A S S R A T G I P D R F S G S G S G T D F T L T I S R L E P
    220       Q K P G Q A P R R L L I Y G A S S R A T G I P D R F S G S G S G T D F T L T I S R L E P
    228       Q K P G Q A P R R L L I Y G A S S R A T G I P D R F S G S G S G T D F T L T I S R L E P
    236       Q K P G Q A P R R L L I Y G A S S R A T G I P D R F S G S G S G T D F T L T I S R L E P Kabat                                   9                                       1
                                                                                0
 No.          1 2 3 4 5 6 7 8 9 0 1 2 3 4 5 6 7 A B C D E F 8 9 0 1 2 3 4 5 6 7 8
SEQ ID NO:
    160       E D S A V Y Y C Q Q F D S S P                 L T F G G G T K V E I K R
    204       E D S A V Y Y C Q Q F D S L P                 L T F G G G T K V E I K R
    212       E D S A V Y Y C Q Q H D S S P                 L S F G G G T K V E I K R
    220       E D S A V Y Y C Q Q F D S S P                 L T F G G G T K V E I K R
    228       E D S A V Y Y C Q Q F D S S P                 L T F G G G T K V E I K R
    236       E D S A V Y Y C Q Q F D S S P                 L T F G G G T K V E I K R
```

Fig. 6B

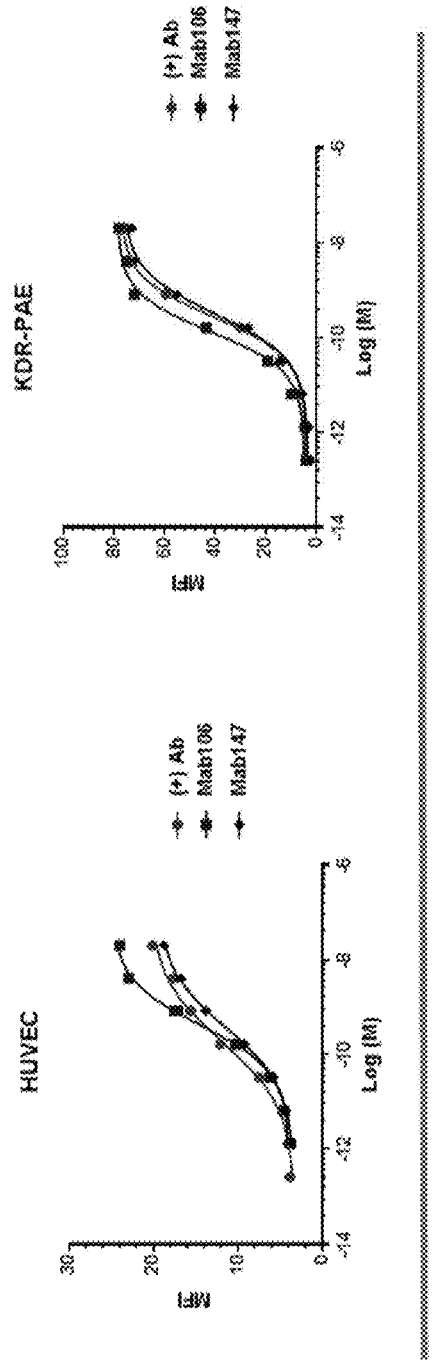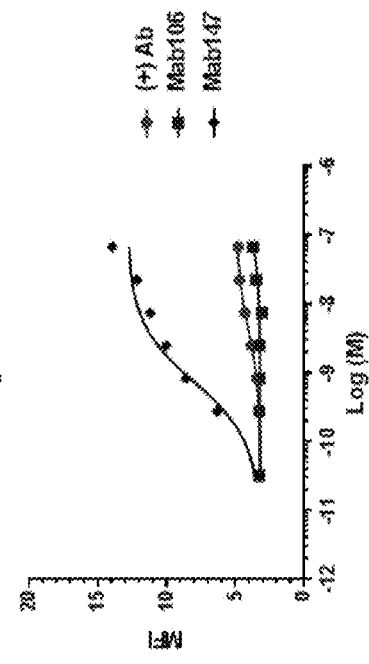
Fig. 8

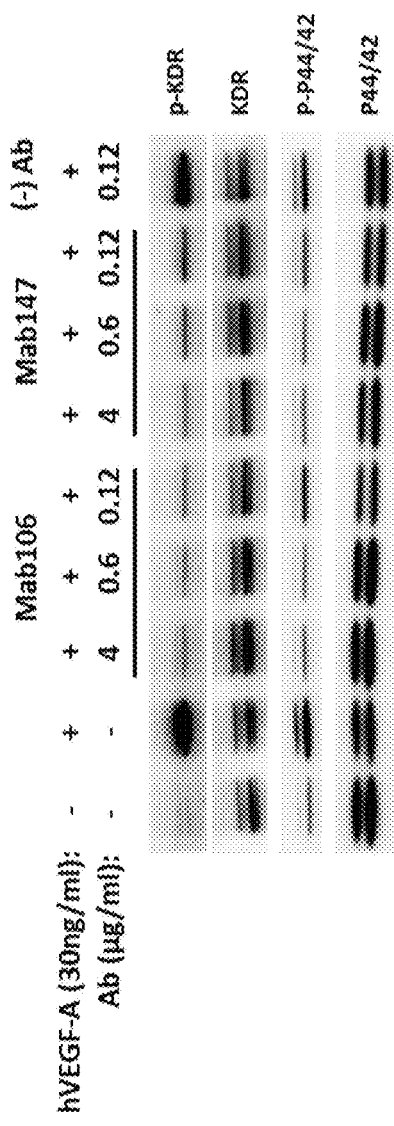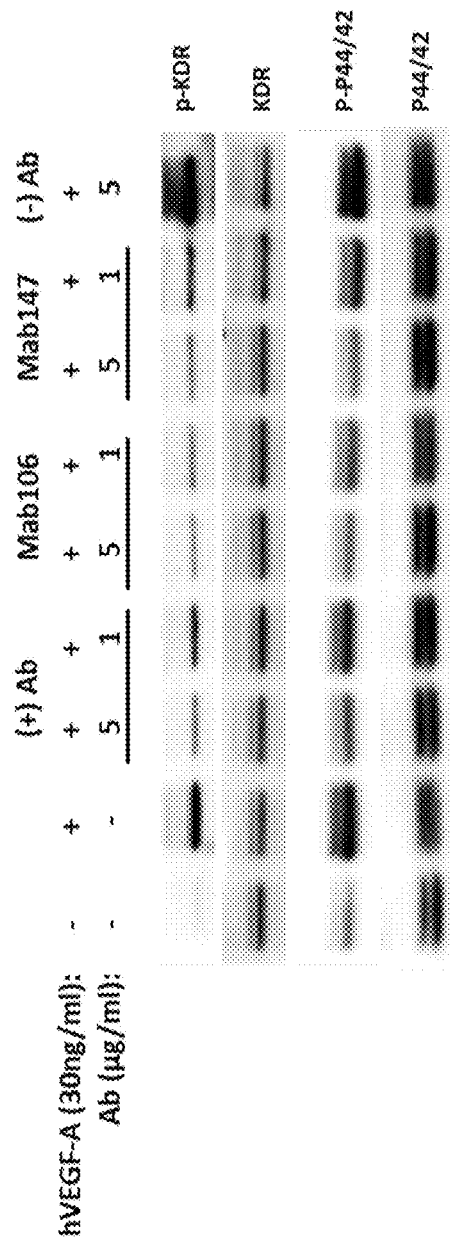
Fig. 9

A.
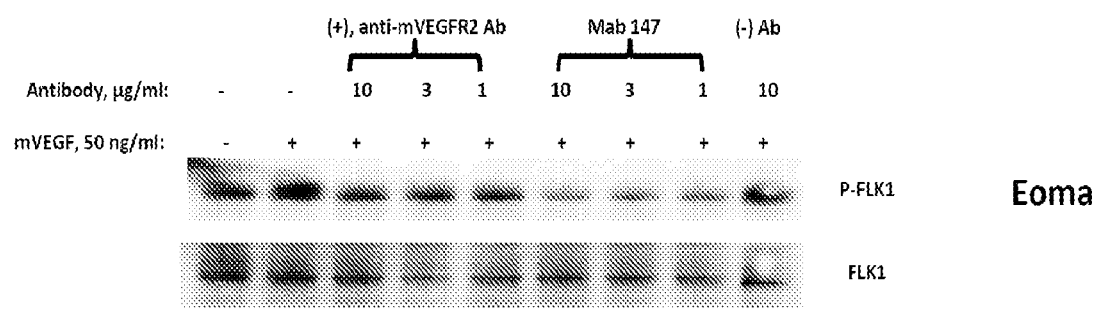
B.
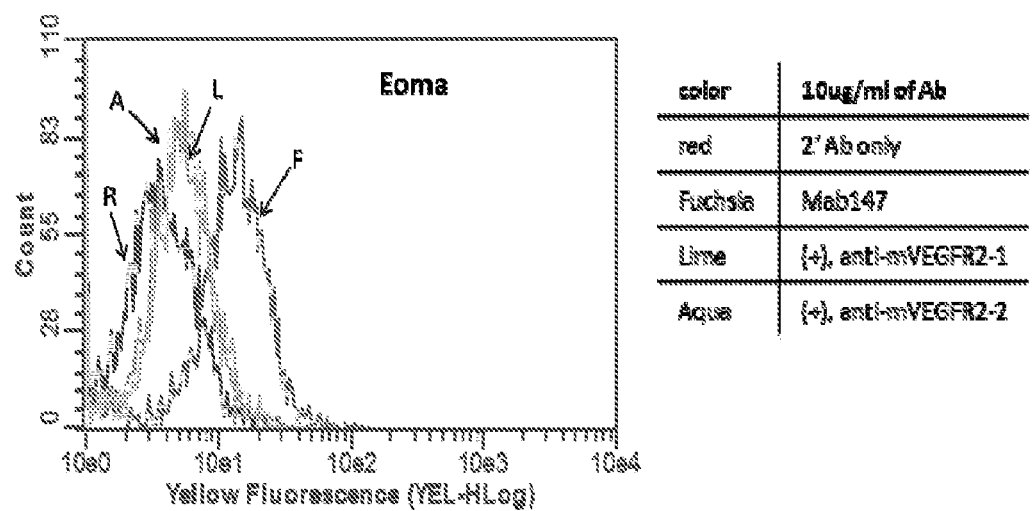
Fig. 12

HUMAN ANTI-VEGFR-2/KDR ANTIBODIES

CROSS-REFERENCE TO RELATED APPLICATIONS

This application is a 371 of PCT/US2015/054569, filed Oct. 7, 2015, which claims the benefit of priority to U.S. Application No. 62/061,097, filed on Oct. 7, 2014, which are incorporated herein by reference in their entireties. This application also relates to PCT/US2013/063754, filed Oct. 7, 2013, and to U.S. Ser. No. 61/710,420, filed Oct. 5, 2012, both of which are incorporated herein by reference in their entireties

FIELD OF THE INVENTION

The invention relates to antibodies that bind to VEGFR-2. The antibodies are used for treating neoplastic diseases and hyperproliferative disorders, and can be used alone or in combination with other agents.

BACKGROUND OF THE INVENTION

Angiogenesis is a highly complex process of developing new blood vessels that involves the proliferation and migration of, and tissue infiltration by capillary endothelial cells from pre-existing blood vessels, cell assembly into tubular structures, joining of newly forming tubular assemblies to closed-circuit vascular systems, and maturation of newly formed capillary vessels.

Angiogenesis is important in normal physiological processes including embryonic development, follicular growth, and wound healing. Undue angiogenesis also leads to neovascularization in neoplastic diseases, and in non-neoplastic diseases such as age-related macular degeneration (AMD), diabetic retinopathy, and neovascular glaucoma. Anti-angiogenic therapy that targets vascular endothelial growth factor (VEGF) with ranibizumab (Lucentis®) has been shown to be effective in delaying progression of AMD. However, neovascularization is complex and multiple angiogenic mechanisms are likely to contribute. There remains a need to develop agents and therapies for treating diseases associated with neovascularization.

SUMMARY OF THE INVENTION

The present invention provides human antibodies, and fragments thereof that bind to VEGFR-2 (KDR). In some embodiments, the antibodies block ligand binding (e.g., one or more of VEGF-A, VEGF-C, VEGF-D, or VEGF-E) to VEGFR-2. In some embodiments, the antibodies neutralize activation of VEGFR-2. The antibodies are used for treating neoplastic diseases, including, for example, solid and non-solid tumors, and hyperproliferative disorders. Accordingly, the invention provides methods of neutralizing the activation of KDR, methods of inhibiting tumor growth, including inhibition of tumor associated angiogenesis, and methods of treating angiogenesis related disorders. The present invention provides kits having human antibodies or antibody fragments that bind to VEGR receptors.

In one embodiment, the invention provides an isolated antibody or fragment thereof that binds to human VEGFR2, comprising a heavy chain variable domain, which comprises a CDR1, a CDR2, and a CDR3 sequence, wherein:

(i) the CDR1 sequence is
GFTFSWYVMG,                (SEQ ID NO: 237)

(ii) the CDR2 sequence is selected from the group consisting of
SIYPQGGATSYADSVKG,         (SEQ ID NO: 238)

SIYPQGGATNYADSVKG,         (SEQ ID NO: 239)
and

SIYPSGGATNYADSVKG;         (SEQ ID NO: 240)
and (ii) the CDR3 sequence selected from the group consisting of
GNYFDY,                    (SEQ ID NO: 241)

GNYLDY,                    (SEQ ID NO: 242)

GPYLDY                     (SEQ ID NO: 243)
and

GSYLDY,                    (SEQ ID NO: 244)

with the proviso that the heavy chain variable domain does not comprise both the CDR2 sequence of SEQ ID NO: 240 and the CDR3 sequence of SEQ ID NO: 241.

In one embodiment, the invention provides an isolated antibody or fragment thereof that binds to human VEGFR2, comprising a light chain variable domain, which comprises a CDR1, a CDR2, and a CDR3 sequence, wherein (i) the CDR1 sequence is
RASQSVSSNYFG,              (SEQ ID NO: 245)

(ii) the CDR2 sequence is
GASSRAT,                   (SEQ ID NO: 246)
and (iii) the CDR3 sequence is selected from the group consisting of
QQFDSLPLT,                 (SEQ ID NO: 247)

QQHDSSPLS,                 (SEQ ID NO: 248)

QQFDSSPLS,                 (SEQ ID NO: 249)
and

QQFDSSPLT.                 (SEQ ID NO: 250)

In one embodiment of the invention, the CDR2 of the heavy chain variable domain has the sequence SIYPQGGATSYADSVKG (SEQ ID NO: 238), and the CDR3 of the heavy chain variable domain has the sequence GNYFDY (SEQ ID NO: 241).

In one embodiment of the invention, the CDR3 of the light chain variable domain has the sequence QQFDSLPLT (SEQ ID NO: 247).

In one embodiment of the invention, the heavy chain variable domain has a sequence that is selected from the group consisting of (SEQ ID NO: 200)
EVQLLESGGGLVQPGGSLRLSCAASGFTFSWYVMGWVRQAPGKGLEWVSS

IYPQGGATSYADSVKGRFTISRDNSKNTLYLQMNSLRAEDTAVYYCARGN

YFDYWGQGTLVTVSS, (SEQ ID NO: 208)
EVQLLESGGGLVQPGGSLRLSCAASGFTFSWYVMSWVRQAPGKGLEWVSS

IYPQGGATNYADSVKGRFTISRDNSKNTLYLQMNSLRAEDTAVYYCARGN

YFDYWGQGTLVTVSS,

-continued (SEQ ID NO: 216)
EVQLLESGGGLVQPGGSLRLSCAASGFTFSWYVMGWVRQAPGKGLEWVSS

IYPSGGATNYADSVKGRFTISRDNSKNTLYLQMNSLRAEDTAVYYCARGN

YLDYWGQGTLVTVSS, (SEQ ID NO: 224)
EVQLLESGGGLVQPGGSLRLSCAASGFTFSWYVMGWVRQAPGKGLEWVSS

IYPSGGATNYADSVKGRFTISRDNSKNTLYLQMNSLRAEDTAVYYCARGP

YLDYWGQGTLVTVSS,
and (SEQ ID NO: 232)
EVQLLESGGGLVQPGGSLRLSCAASGFTFSWYVMGWVRQAPGKGLEWVSS

IYPSGGATNYADSVKGRFTISRDNSKNTLYLQMNSLRAEDTAVYYCARGS

YLDYWGQGTLVTVSS.

In one embodiment of the invention, the light chain variable domain has a sequence that is selected from the group consisting of (SEQ ID NO: 204)
DIQMTQSPGTLSLSPGEGATLSCRASQSVSSNYFGWYQQKPGQAPRLLIY

GASSRATGIPDRFSGSGSGTDFTLTISRLEPEDSAVYYCQQFDSLPLTFG

GGTKVEIKR, (SEQ ID NO: 212)
DIQMTQSPGTLSLSPGEGATLSCRASQSVSSNYFGWYQQKPGQAPRLLIY

GASSRATGIPDRFSGSGSGTDFTLTISRLEP EDSAVYYCQQHDSSPLSF

GGGTKVEIKR, (SEQ ID NO: 220)
DIQMTQSPGTLSLSPGEGATLSCRASQSVSSNYFGWYQQKPGQAPRLLIY

GASSRATGIPDRFSGSGSGTDFTLTISRLEPEDSAVYYCQQFDSSPLSFG

GGTKVEIKR, (SEQ ID NO: 228)
DIQMTQSPGTLSLSPGEGATLSCRASQSVSSNYFGWYQQKPGQAPRLLIY

GASSRATGIPDRFSGSGSGTDFTLTISRLEP EDSAVYYCQQFDSSPLTF

GGGTKVEIKR,
and (SEQ ID NO: 236)
DIQMTQSPGTLSLSPGEGATLSCRASQSVSSNYFGWYQQKPGQAPRLLIY

GASSRATGIPDRFSGSGSGTDFTLTISRLEP EDSAVYYCQQFDSSPLTF

GGGTKVEIKR.

In one embodiment of the invention, the heavy chain variable domain has a sequence that is (SEQ ID NO: 200)
EVQLLESGGGLVQPGGSLRLSCAASGFTFSWYVMGWVRQAPGKGLEWVSS

IYPQGGATSYADSVKGRFTISRDNSKNTLYLQMNSLRAEDTAVYYCARGN

YFDYWGQGTLVTVSS, and the light chain variable domain has a sequnce that is (SEQ ID NO: 204)
DIQMTQSPGTLSLSPGEGATLSCRASQSVSSNYFGWYQQKPGQAPRLLIY
GASSRATGIPDRFSGSGSGTDFTLTISRLEPEDSAVYYCQQFDSLPLTFG
GGTKVEIKR.

In one embodiment of the invention, the antibody or fragment has isotype IgG.

In one embodiment of the invention, the antibody or fragment is an scFv, Fv, Fab', Fab, F(ab')2, or diabody.

In one embodiment of the invention, the the antibody or fragment binds to human VEGFR2 and murine hVEGFR2.

The present invention provides an isolated nucleic acid encoding the antibody or fragment of the present invention.

The present invention provides a nucleic acid vector comprising an isolated nucleic acid encoding the antibody or fragment of the present invention.

The present invention provides a prokaryotic or eukaryotic host cell comprising an isolated nucleic acid encoding the antibody or fragment of the present invention.

The present invention provides a composition comprising an antibody or fragment of the present invention, and a pharmaceutically acceptable carrier.

The present invention provides a method of neutralizing activation of human VEGFR2 or murine VEGFR2 comprising contacting a cell with an effective amount of an antibody or fragment of the present invention.

The present invention provides a method of inhibiting angiogenesis comprising administering to a subject an effective amount of an antibody or fragment of the present invention.

The present invention provides a method of reducing tumor growth comprising administering to a subject an effective amount of an antibody or fragment of the present invention.

The present invention provides a method of treating a neoplastic diseases in a subject, comprising administering to a subject an effective amount of an antibody or fragment of the present invention, wherein the neoplastic diseases is selected from the group consitring of lung cancer, colorectal cancer renal cell carcinoma, glioblastoma, ovarian cancer, bladder cancer, gastric cancer, multiple myeloma, non-small cell lung cancer and pancreatic cancer.

In one embodiment of the invention, the method which further comprises administering to a subject an effective amount of an epidermal growth factor receptor (EGFR) antagonist.

In one embodiment of the invention, the method which further comprises administering to a subject an effective amount of an fms-like tyrosine kinase receptor (flt-1) antagonist.

In one embodiment of the invention, the method which further comprises administering to a subject an effective amount of a rho associated kinase 2 (ROCK2) antagonist.

In one embodiment of the invention, the method which further comprises administering to a subject an effective amount of a matrix metalloproteinase antagonist.

In one embodiment of the invention, the method which further comprises administering to a subject an effective amount of a PDGFRβ antibody.

In one embodiment of the invention, the method which further comprises administering to a subject an effective amount of a PD-L1 antibody.

In one embodiment of the invention, the patient is a human.

BRIEF DESCRIPTION OF THE FIGURES

Figure 1B2:
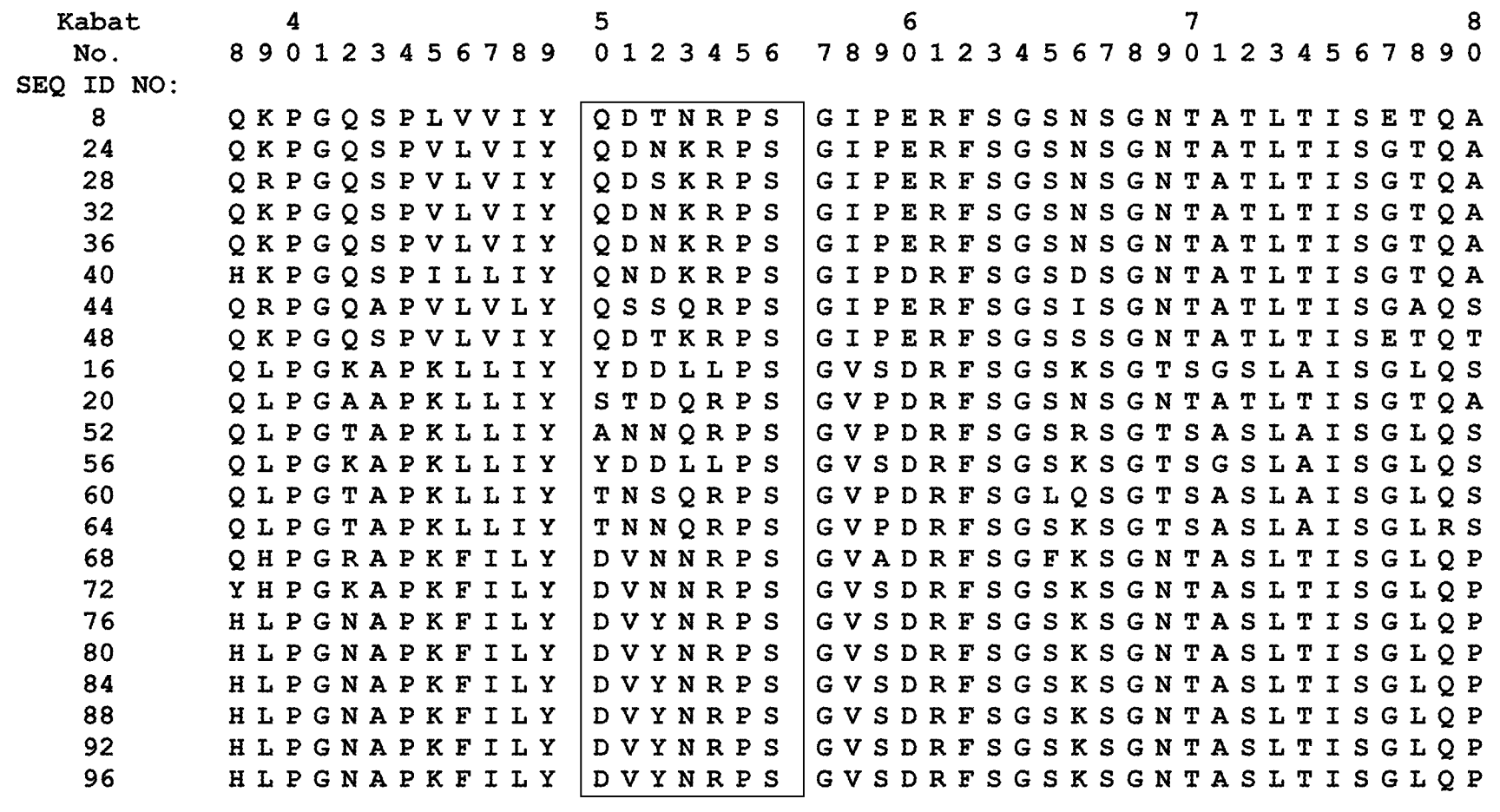

FIGS. 1A-C show human heavy chain, lambda light chain, and kappa light chain variable region sequences, respectively, of anti-VEGFR2 antibodies of the invention identified by phage display.

FIG. 4 shows binding to hVEGFR2 and VEGF$_{165}$ ligand blocking by Mabs 104, 105, 106, and 108. Similar results were obtained for Mabs 103, 107, 109, and 110 in a separate experiment. These Mabs contain the heavy chain variable domain of Mab101, recombined with different light chain variable domains.

FIG. 5 shows Mabs 105 and 106 of the invention inhibit VEGFA-stimulated phosphorylation of VEGFR2 (KDR, FIG. 5A), p44/42 MAPK (FIG. 5B), and AKT (FIG. 5C) in porcine aortic endothelial (PAE) cells overexpressing KDR (human VEGFR2).

FIG. 6A depicts heavy chain amino acid sequences of five affinity matured antibodies derived from Mab 138, which contains the V$_H$ domain having SEQ ID NO:4 (sequence as shown in this Figure). FIG. 6B depicts light chain amino acid sequences of the same five affinity matured antibodies derived from SEQ ID NO:160 (sequence as shown in this Figure).

FIG. 8A depicts the binding of Mab106 and Mab 147 to human VEGFR2 on HUVEC (Human Umbilical Vein Endothelial Cells) and porcine aortic endothelial (PAE) cells overexpressing KDR (KDR-PAE). FIG. 8B show Mab 147, but not Mab 106, binds to VEGFR2 on MS1 murine endothelial cells. In FIGS. 8A and 8B, the control is an antibody that binds to hVEGFR2 but not mVEGFR2.

FIG. 9 shows inhibition of VEGFR2-mediated signal transduction by Mab 106 and Mab 147. Mab 106 and Mab 147 inhibit phosphorylation of KDR and p44/42 in KDR-PAE (FIG. 9A) cells and in HUVEC (FIG. 9B) in a dose dependent manner.

FIG. 12A depicts inhibition of VEGFR2-mediated signal transduction in murine EOMA cells by Mab 147. And FIG. 12B depicts FACS studies demonstrating that Mab 147 has increased binding to EOMA cells by comparison to control antibodies.

DETAILED DESCRIPTION

Figure 2:
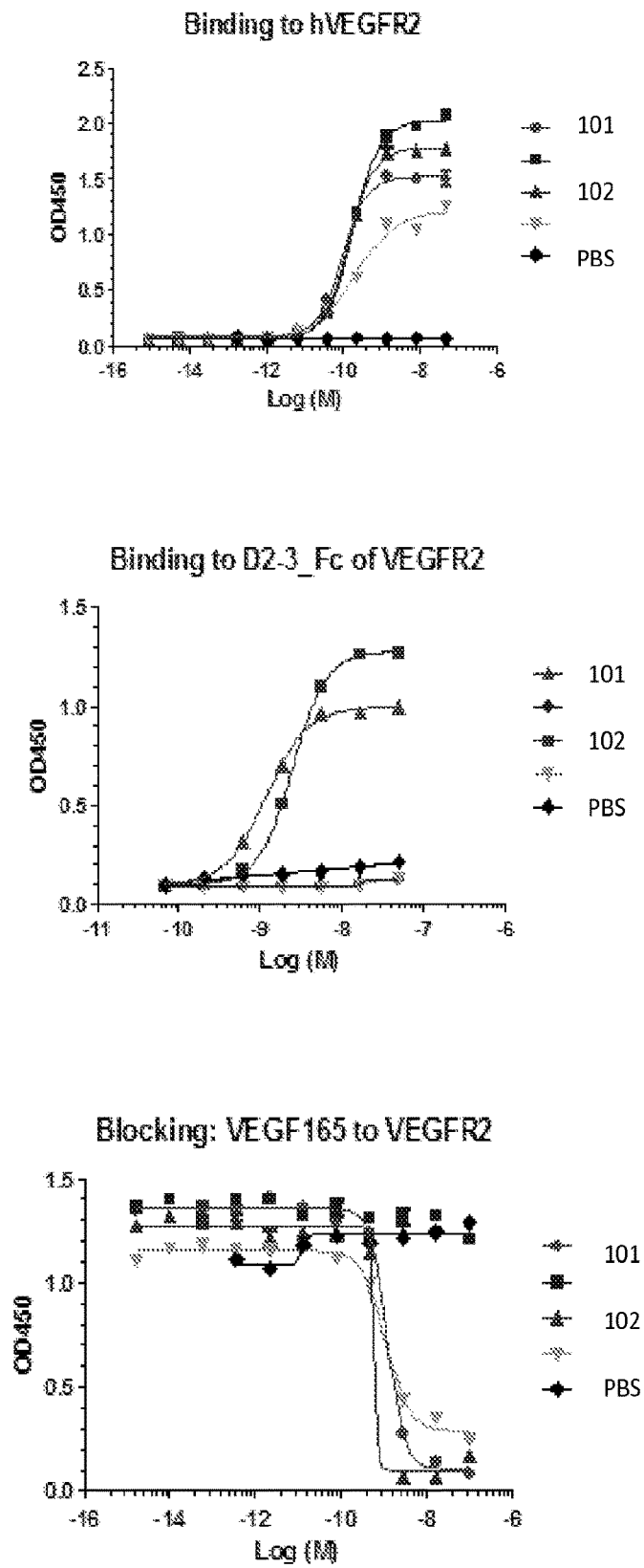
FIG. 2 shows binding of antibodies of the invention to hVEGFR2 (top) and a construct containing domains 2 and 3 of hVEGFR2 (middle). The bottom panel shows ligand (VEGF$_{165}$) blocking.

In one aspect, the invention provides novel VEGFR2 antibodies or antigen binding fragments of such antibodies are employed, which are effective to inhibit VEGFR2-dependent signal transduction. As used herein, "inhibiting a receptor" means diminishing and/or inactivating the intrinsic kinase activity of the receptor to transduce a signal. A reliable assay for VEGFR2 inhibition is reduction of receptor phosphorylation.

The present invention is not limited by any particular mechanism of VEGFR2 inhibition. The mechanism followed by one antibody is not necessarily the same as that followed by another. Some possible mechanisms include preventing binding of the VEGF ligand to the extracellular binding domain of the VEGFR2, and preventing dimerization or oligomerization of receptors. Other mechanisms cannot, however, be ruled out.

Antibodies are proteins that recognize and bind to a specific antigen or substance. In preferred embodiments, the antibodies of the present invention bind KDR at least as strongly as the natural ligand. Affinity, represented by the equilibrium constant for the dissociation of an antigen with an antibody (Kd), measures the binding strength between an antigenic determinant and an antibody binding site. Avidity is the measure of the strength of binding between an antibody with its antigen. Avidity is related to both the affinity between an antigenic determinant and an antigen binding site on the antibody, and the number of binding sites (valence) per antibody. For example, a monovalent antibody (e.g., Fab) has one binding site for a particular epitope. An IgG antibody has two antigen binding sites. Typical values of K (the reciprocal of the dissociation constant K$_d$) are $10^5$ to $10^{11}$ liters/mol. Any K weaker than $10^4$ liters/mol is considered to indicate binding which is nonspecific.

Antibodies of the invention inhibit activation of VEGFR2. One measure of VEGFR2 inhibition is reduced tyrosine kinase activity of the receptor. Tyrosine kinase inhibition can be determined using well-known methods, such as measuring the autophosphorylation level of the receptor Inhibition of VEGFR2 can also be observed through inhibition or regulation of phosphorylation events of natural or synthetic VEGFR2 substrates and other components of the VEGFR2 signal transduction pathway. Phosphorylation can be detected, for example, using an antibody specific for phosphotyrosine in an ELISA assay or on a western blot. Some assays for tyrosine kinase activity are described in Panek et al., *J. Pharmacol. Exp. Thera.*, 283: 1433-44 (1997) and Batley et al., *Life Sci.*, 62: 143-50 (1998).

In vivo assays can also be utilized. For example, receptor tyrosine kinase inhibition can be observed by mitogenic assays using cell lines stimulated with receptor ligand in the presence and absence of inhibitor. For example, HUVEC cells (ATCC) stimulated with VEGF can be used to assay VEGFR inhibition. Another method involves testing for inhibition of growth of VEGF-expressing tumor cells, using for example, human tumor cells injected into a mouse. See, U.S. Pat. No. 6,365,157 (Rockwell et al.).

The invention provides anti-VEGFR2 antibodies, including nucleic acids encoding such antibodies and compositions comprising such antibodies. In one embodiment the invention provides an isolated antibody heavy chain variable region comprising a CDR-1H, CDR-2H, and CDR-3H sequence, wherein:

(i) the CDR-1H sequence is
GFTFSWYX$_1$MX$_2$,           (SEQ ID NO: 185)
wherein X$_1$ is V or I, X$_2$ is G or L, (ii) the CDR-2H sequence is
SIX$_1$X$_2$SGGX$_3$TX$_4$YADSVKG,      (SEQ ID NO: 186)
wherein X$_1$ is Y or G, X$_2$ is P or S, X$_3$ is A or F, X$_4$ is N or D,
and (iii) the CDR-3H sequence is
GNYFDY              (SEQ ID NO: 3)
or

GLAAPRS.            (SEQ ID NO: 11)

In one embodiment, the invention provides an isolated light chain variable region comprising a CDR-L1, CDR-L2, and CDR-L3, wherein (i) the CDR-L1 sequence is
X$_1$GX$_2$X$_3$LX$_4$X$_5$X$_6$X$_7$X$_8$S,        (SEQ ID NO: 187)
wherein X$_1$ is S, Q, or T, X$_2$ is D, E, or Q, X$_3$ is K, S, N, I, or A, X$_4$ is G or R, X$_5$ is D, S, H, E, or N, X$_6$ is E, Y, Q, R, or N, X$_7$ is Y, F, or S, and X$_8$ is A or S,
or SGSX$_1$SNX$_2$X$_3$X$_4$X$_5$X$_6$X$_7$X$_8$,      (SEQ ID NO: 188)
wherein X$_1$ is S, or T, X$_2$ is I or L, X$_3$ is E or G, X$_4$ is T, S, or N, X$_5$ is N or Y, X$_6$ is T, P, A, or Y, X$_7$ is V or L, and X$_8$ is N, I, or Y,
or X$_1$GX$_2$SX$_3$DX$_4$GX$_5$YDYVS,      (SEQ ID NO: 189)
wherein X$_1$ is A or T, X$_2$ is S or T, X$_3$ is H, S, or N, X$_4$ is I or V, and X$_5$ is S or A, (ii) the CDR-L2 sequence is
X$_1$X$_2$X$_3$X$_4$X$_5$PS,           (SEQ ID NO: 190)
wherein wherein X$_1$ is Q, D, T, Y, S, or A, X$_2$ is D, N, S, T, or V, X$_3$ is D, N, S, T, or Y, X$_4$ is Q, K, N, or L, and X$_5$ is R or L,
and (iii) wherein the CDR-L3 sequence is
QX$_1$WX$_2$X$_3$X$_4$X$_5$X$_6$X$_7$X$_8$,       (SEQ ID NO: 191)
wherein X$_1$ is A or T, X$_2$ is D or G, X$_3$ is R or no amino acid, X$_4$ is S, F, or N, X$_5$ is S, T, or N, X$_6$ is S, T, or P, X$_7$ is A, V, L, I, or Y, and X$_8$ is V or L,
or AX$_1$WDDX$_2$LX$_3$X$_4$X$_5$X$_6$,        (SEQ ID NO: 192)
wherein X$_1$ is A, S, or T, X$_2$ is N or S, X$_3$ is N, I, or G, X$_4$ is G or S, X$_5$ is P, W, or V, and X$_6$ is V or L,
or MYSTITX$_1$LL,              (SEQ ID NO: 193)
wherein X$_1$ is A or T.

In one embodiment, the invention provides an isolated light chain variable region comprising a CDR-L1, CDR-L2, and CDR-L3, wherein (i) the CDR-L1 sequence is
RASX$_1$X$_2$X$_3$X$_4$X$_5$X$_6$X$_7$YX$_8$X$_9$,     (SEQ ID NO: 194)
wherein X$_1$ is Q, E, or H, X$_2$ is S, R, or N, X$_3$ is V, I, or L, X$_4$ is S, R, G or N, X$_5$ is S or N, X$_6$ is S, N, W, or D, X$_7$ is G or no amino acid, X$_8$ is L or F, and X$_9$ is A, G, M, or S, (ii) the CDR-L2 sequence is
GASX$_1$RAT,                (SEQ ID NO: 195)
wherein X$_1$ is S, T, I, or N,
and (iii) the CDR-L3 sequence is
QQX$_1$X$_2$X$_3$X$_4$X$_5$X$_6$X$_7$X$_8$,       (SEQ ID NO: 196)
wherein X$_1$ is F or Y, X$_2$ is D, G, or Y, X$_3$ is S, T, or N, X$_4$ is S, L, or W, X$_5$ is P or no amino acid, X$_6$ is P or T, X$_7$ is L, I, V, P, W, or Y, and X$_8$ is T or S.

In an embodiment of the invention, an antibody is provided which comprises a heavy chain variable domain comprising one, two, three, four, five, or six of the light chain variable domain and heavy chain variable domain CDR sequences set forth above.

Non-limiting examples of VEGFR2-binding antibody sequences are provided. As described herein, from human Fab phage display libraries, two neutralizing antibodies were identified that bind to human VEGFR2, block binding of the ligand VEGFA to hVEGFR2, and inhibit the VEGFR2 phosphorylation and downstream signal transduction stimulated by VEGFA. Table 1 indicates amino acid sequences of the CDRs and variable domains of antibodies of the antibodies. The $K_d$s of Mab 101 and Mab 102 are about 6.6 mM and 1.7 nM, respectively.

TABLE 1

Antibody Amino Acid Sequences by SEQ ID NO

| Mab | CDR-H1 | CDR-H2 | CDR-H3 | $V_H$ domain | CDR-L1 | CDR-L2 | CDR-L3 | $V_L$ domain |
|---|---|---|---|---|---|---|---|---|
| 101 | 1 | 2 | 3 | 4 | 5 | 6 | 7 | 8 |
| 102 | 9 | 10 | 11 | 12 | 13 | 14 | 15 | 16 |

The heavy chain of Mab 101 was reshuffled with κ light chain genes (κ-library) and λ light chain genes (λ-library). 20 unique λ light chain variants were found by panning the λ-library against both human VEGFR2 and mouse VEGFR2. 22 unique κ light chain variants were found by panning the λ-library against both human VEGFR2 and mouse VEGFR2. Table 2 indicates amino acid sequences of the CDRs and variable domains of the light chains. The $K_d$s of Mabs 105, 106, and 107 were increased about 10 fold (0.24 nM, 0.22 nM, and 0.12 nM, respectively). Like the parent antibody, these antibodies bind to VEGFR2 and block binding of VEGFA to VEGFR2, and inhibit VEGFA-stimulated phosphorylation of VEGFR2, AKT, and MAPK. (FIG. 4).

Several of the antibodies, including Mabs 138, 139, 140, and 146, also cross react with mouse VEGFR2. These antibodies also inhibited VEGFA-stimulated phosphorylation of VEFGR2 and downstream signal transduction molecules, including MAPK.

TABLE 2

κ and λ light chains by SEQ ID NO

| | | SEQ ID NO | | | |
|---|---|---|---|---|---|
| Mab | light chain | CDR-L1 | CDR-L2 | CDR-L3 | $V_L$ |
| 103 | λ | 17 | 18 | 19 | 20 |
| 104 | λ | 21 | 22 | 23 | 24 |

TABLE 2-continued

κ and λ light chains by SEQ ID NO

| Mab | light chain | CDR-L1 | CDR-L2 | CDR-L3 | V_L |
|---|---|---|---|---|---|
| 105 | λ | 25 | 26 | 27 | 28 |
| 106 | λ | 29 | 30 | 31 | 32 |
| 107 | λ | 33 | 34 | 35 | 36 |
| 108 | λ | 37 | 38 | 39 | 40 |
| 109 | λ | 41 | 42 | 43 | 44 |
| 110 | λ | 45 | 46 | 47 | 48 |
| 111 | λ | 49 | 50 | 51 | 52 |
| 112 | λ | 53 | 54 | 55 | 56 |
| 113 | λ | 57 | 58 | 59 | 60 |
| 114 | λ | 61 | 62 | 63 | 64 |
| 115 | λ | 65 | 66 | 67 | 68 |
| 116 | λ | 69 | 70 | 71 | 72 |
| 117 | λ | 73 | 74 | 75 | 76 |
| 118 | λ | 77 | 78 | 79 | 80 |
| 119 | λ | 81 | 82 | 83 | 84 |
| 120 | λ | 85 | 86 | 87 | 88 |
| 121 | λ | 89 | 90 | 91 | 92 |
| 122 | λ | 93 | 94 | 95 | 96 |
| 123 | κ | 97 | 98 | 99 | 100 |
| 124 | κ | 101 | 102 | 103 | 104 |
| 125 | κ | 105 | 106 | 107 | 108 |
| 126 | κ | 109 | 110 | 111 | 112 |
| 127 | κ | 113 | 114 | 115 | 116 |
| 128 | κ | 117 | 118 | 119 | 120 |
| 129 | κ | 121 | 122 | 123 | 124 |
| 130 | κ | 125 | 126 | 127 | 128 |
| 131 | κ | 129 | 130 | 131 | 132 |
| 132 | κ | 133 | 134 | 135 | 136 |
| 133 | κ | 137 | 138 | 139 | 140 |
| 134 | κ | 141 | 142 | 143 | 144 |
| 135 | κ | 145 | 146 | 147 | 148 |
| 136 | κ | 149 | 150 | 151 | 152 |
| 137 | κ | 153 | 154 | 155 | 156 |
| 138 | κ | 157 | 158 | 159 | 160 |
| 139 | κ | 161 | 162 | 163 | 164 |
| 140 | κ | 165 | 166 | 167 | 168 |
| 141 | κ | 169 | 170 | 171 | 172 |
| 142 | κ | 173 | 174 | 175 | 176 |
| 143 | κ | 177 | 178 | 179 | 180 |
| 144 | κ | 181 | 182 | 183 | 184 |

The invention provides an isolated VEGFR2 antibody, and VEGFR2 binding fragments thereof, which comprises one, two, or three heavy chain CDRs and one, two, or three light chain CDRs, selected from the sequences set forth in Table 1 and Table 2. In an antibody of the invention, when more than one CDR is selected from the sequences presented in Table 1 and Table 2, the different CDRs need not be selected from the same monoclonal antibody presented in those tables, but can be selected from two or more antibody variable domains presented in the tables. Specific embodiments include, but are not limited to, the following. In an embodiment of the invention, the isolated VEGFR2 antibody comprises one, two, or three heavy chain CDRs having SEQ ID NO:1, SEQ ID NO:2, and SEQ ID NO:3. In an embodiment, of the invention, the antibody comprises one, two, or three light chain CDRs having SEQ ID NO:5, SEQ ID NO:6, and SEQ ID NO:7. In another embodiment, the antibody comprises one, two, or three light chain CDRs having sequences as set forth in Table 1 or 2. Non-limiting examples include a light chain variable region comprising one or more of SEQ ID NO:25, SEQ ID NO:26, and SEQ ID NO:27, one or more of SEQ ID NO:29, SEQ ID NO:30, and SEQ ID NO:31, or one or more of SEQ ID NO:33, SEQ ID NO:34, and SEQ ID NO:35. In certain embodiments, the VEGFR2 antibody comprises a heavy chain variable domain comprising SEQ ID NO:4 or SEQ ID NO:12. In certain embodiments, the VEGFR2 antibody comprises a light chain variable domain comprising SEQ ID NO:8, SEQ ID NO:16, SEQ ID NO:27, SEQ ID NO:31, or SEQ ID NO:35. In certain embodiments, the antibodies comprise one of the above-mentioned heavy chain variable domains and one of the above-mentioned light chain variable domains. In certain embodiments, the VEGFR2 antibodies or binding fragments thereof comprise one or more CDRs or one or more variable domains with an amino acid sequence at least 85% at least 90%, at least 95%, at least 97%, at least 98%, or at least 99%, identical to the CDR and variable domain sequences set forth in Table 1 or 2. In certain embodiments, antibodies of the invention have CDR amino acids identical to those disclosed herein and frameworks that are at least least 85%, at least 90%, of at least 95% identical.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 80%, more preferably at least 85%, and most preferably at least 90% similar to another amino acid sequence. Methods and computer programs for determining sequence similarity are publically available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Antibodies of the invention also include those for which binding characteristics have been improved by direct mutation, methods of affinity maturation, phage display, or chain shuffling. Affinity and specificity may be modified or improved by mutating CDRs and screening for antigen binding sites having the desired characteristics. CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

To minimize the immunogenicity of antibodies that bind to VEGF receptors, the present invention provides antibodies which comprise human variable and constant domain sequences. The antibodies may be or may combine members of any immunoglobulin class, such as IgG, IgM, IgA, IgD, or IgE, and the subclasses thereof. The antibody class may be selected to optimize effector functions (e.g., complement dependent cytoxicity (CDC) and antibody dependent cellular cytoxicity (ADCC)) of natural antibodies.

Certain embodiments of the invention involve the use of VEGFR2-binding antibody fragments. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. In an embodiment of the invention, the linker is (Gly-Gly-Gly-Gly-Ser)$_3$. Since scFv fragments lack the constant domains of whole antibodies, they are considerably smaller than whole antibodies. scFv fragments are also free of normal heavy-chain constant domain interactions with other biological molecules which may be undesired in certain embodiments.

Fragments of an antibody containing $V_H$, $V_L$, and optionally $C_L$, $C_H 1$, or other constant domains can also be used. Monovalent fragments of antibodies generated by papain digestion are referred to as Fab and lack the heavy chain hinge region. Fragments generated by pepsin digestion, referred to as F(ab')$_2$, retain the heavy chain hinge and are divalent. Such fragments may also be recombinantly produced. Many other useful antigen-binding antibody fragments are known in the art, and include, without limitation, diabodies, triabodies, single domain antibodies, and other monovalent and multivalent forms.

The invention further provides multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the inimunoglobulin molecule is multispecific.

For example, a bispecific multivalent single chain antibody allows for the recognition of two different types of epitopes. Both epitopes may be on the same antigen (e.g., VEGFR2). Alternatively, one epitope may be on one antigen (e.g., VEGFR2), and the second epitope on a different antigen.

In one embodiment, a multivalent single chain antibody includes a variable light-chain fragment linked to a variable heavy-chain fragment (similar to an scFv), which is further linked by another peptide linker to at least one other antigen binding domain. Typically, the peptide linker is composed of about fifteen amino acid residues. In a preferred embodiment, the number of $V_L$ and $V_H$ domains is equivalent. For example, a bivalent single chain antibody can be represented as follows: $V_L$-$L_1$-$V_H$-$L_2$-$V_L$-$L_3$-$V_H$ or $V_L$-$L_1$-$V_H$-$L_2$-$V_H$-$L_3$-$V_L$ or $V_H$-$L_1$-$V_L$-$L_2$-$V_H$-$L_3$-$V_L$ or $V_H$-$L_1$-$V_L$-$L_2$-VL-$L_3$-$V_H$. Multivalent single chain antibodies which are trivalent or greater have one or more antibody fragments joined to a bivalent single chain antibody by additional peptide linkers. One example of a trivalent single chain antibody is: $V_L$-$L_1$-$V_H$-$L_2$-$V_L$-$L_1$-$V_H$-$L_2$-$V_L$-$L_1$-$V_H$.

Two single chain antibodies can be combined to form a diabody, also known as bivalent dimer. Diabodies have two chains. Each chain of the diabody includes a $V_H$ domain connected to a $V_L$ domain by a short linker of about 5-10 amino acid residues, e.g. (Gly-Gly-Gly-Gly-Ser), SEQ ID NO:251; (Gly-Gly-Gly-Gly-Ser)$_2$, SEQ ID NO:252. Such linkers are short enough to prevent intrachain pairing between domains on the same chain, thus driving interchain pairing between complementary domains on different chains and recreate two antigen-binding sites. The diabody structure is rigid and compact, with antigen-binding sites are at opposite ends of the molecule. Diabodies may be monospecific or bispecific.

Three single chain antibodies can be combined to form a triabody, also known as a trivalent trimers. In some embodiments, triabodies are constructed with the carboxy terminus of a $V_L$ or $V_H$ domain directly fused to the amino terminus of a $V_H$ or $V_L$ domain, i.e., without any linker sequence. The triabody has three Fv heads with the polypeptides arranged in a cyclic, head-to-tail fashion. A possible conformation of the triabody molecule is planar with the three binding sites located in a plane at an angle of 120 degrees from one another. Triabodies may be monospecific, bispecific or trispecific.

It is understood that the anti-VEGFR2 antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

In the methods of the present invention, a therapeutically effective amount of an antibody of the invention is administered to a mammal in need thereof. The term "administering" as used herein means delivering the antibodies of the present invention to a mammal by any method that may achieve the result sought. They may be administered, for example, intravenously or intramuscularly. Although human antibodies of the invention are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity. For example, depending on the disease, for an antibody, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

Antibodies of the invention are useful for inhibiting tumor growth, angiogenesis associated with tumor growth, or other pathologic condition associated with angiogenesis. Tumors that can be treated include primary tumors, metastatic tumors, and refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued. The antibodies are effective for treating vascularized tumors and tumor that are not vascularized, or not yet substantially vascularized.

Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Examples of non-solid tumors include leukemia, multiple myeloma and lymphoma. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

Antibodies of the invention can also be used to treat or preventing pathologic conditions characterized by excessive angiogenesis, involving, for example, vascularization and/or inflammation, such as atherosclerosis, rheumatoid arthritis (RA), hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

Ocular diseases characterized by excessive angiogeneis include neovascular glaucoma, proliferative retinopathy including proliferative diabetic retinopathy, and macular degeneration The invention provides methods and compounds for treating ocular diseases and disorders. In one embodiment, the invention provides for treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of, among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). Other diseases treatable according to the invention include, without limitation, iris neovascularization, uveitis, neovascular glaucoma, and retinitis of prematurity (ROP). The method of treatment can be prophylactic, such as to stave off corneal neovascularization after corneal transplant, or to modulate the wounnd healing process in trabeculectomy surgery.

Antibodies and antigen binding fragments of the invention can be advantageously administered with second agents to patients in need thereof. For example, in some embodiments, a VEGFR-2 antibody of the invention is administered to a subject with an anti-neoplastic agent. In some embodiments, a VEGFR-2 antibody is administered to a subject with a second angiogenesis inhibitor. In some embodiments, a VEGFR-2 antibody of the invention is administered with an anti-inflammatory agent or an immunosuppressant.

Antineoplastic agents include cytotoxic chemotherapeutic agents, targeted small molecules and biological molecules, and radiation. Non-limiting examples of chemotherapeutic agents include cisplatin, dacarbazine (DTIC), dactinomycin, irinotecan, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Non-limiting examples of growth factor receptors involved in tumorigenesis are the receptors for platelet-derived growth factor (PDGFR), insulin-like growth factor (IGFR), nerve growth factor (NGFR), and fibroblast growth factor (FGFR), and receptors of the epidermal growth factor receptor family, including EGFR (erbB1), HER2 (erbB2), erbB3, and erbB4.

EGFR antagonists induce antibodies that bind to EGFR or to an EGFR ligand, and inhibits ligand binding and/or receptor activation. For example, the agent can block formation of receptor dimers or heterodimer with other EGFR family members. Ligands for EGFR include, for example, EGF, TGF-α amphiregulin, heparin-binding EGF (HB-EGF) and betarecullulin. An EGFR antagonist can bind externally to the extracellular portion of EGFR, which may or may not inhibit binding of the ligand, or internally to the tyrosine kinase domain. EGFR antagonists further include agents that inhibit EGFR-dependent signal transduction, for example, by inhibiting the function of a component of the EGFR signal transduction pathway. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Small molecule and biological inhibitors include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c] pyrrol-5-yl]methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a rho-kinase inhibitor of Formula I and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and SFKs. Two other oral tyrosine kinase inhibitor of Src and Bcr-Abl are bosutinib (SKI-606) and saracatinib (AZD0530).

While VEGFR2 mediates the majority of the downstream effects of VEGF in angiogenesis, it can be advantageous to administer a second angiogenesis inhibitor. Anti-VEGFR-2 antibodies of the invention may be administered with antibodies that neutralize other receptors involved in tumor growth or angiogenesis.

Non-limiting examples of VEGF-binding agents include VEGF antibodies and VEGF traps (i.e., ligand binding domains of VEGF receptors. Two examples of antibodies (including VEGF-binding antibody fragments) are bevacizumab (Avastin), an antibody which binds to VEGF-A, and ranibizumab (Lucentis), an Fab derived from bevacizumab. In general, a VEGF trap is a protein that comprises VEGF-binding domains of one or more VEGF receptor protein. VEGF-traps include, without limitation, soluble VEGFR-1, soluble neuropilin 1 (NRP1), soluble VEGFR-3 (which binds VEGF-C and VEGF-D), and aflibercept (Zaltrap; Eylea; VEGF Trap R1R2), comprised of segments of the extracellular domains of human vascular endothelial growth factor receptors VEGFR1 and VEGFR2 fused to the constant region (Fc) of human IgG1. Conbercept (KH902) is a fusion protein which contains the extracellular domain 2 of VEGFR-1 (Flt-1) and extracellular domain 3, 4 of VEGFR-2 (KDR) fused to the Fc portion of human IgG1. Several VEGF traps containing KDR and FLT-1 Ig-like domains in various combinations are disclosed in U.S. Pat. No. 8,216,575. DARPins (an acronym for designed ankyrin repeat proteins) are genetically engineered antibody mimetic proteins typically exhibiting highly specific and high-affinity target protein binding. DARPin® MP0112 is a vascular endothelial growth factor (VEGF) inhibitor and has entered clinical trials for the treatment of wet macular degeneration and diabetic macular edema.

According to the invention, VEGF expression can be targeted. For example, VEGF inhibitor PTC299 targets VEGF post-transcriptionally by selectively binding the 5'- and 3'-untranslated regions (UTR) of VEGF messenger RNA (mRNA), thereby preventing translation of VEGF. Pegaptanib (Macugen) is an RNA aptamer directed against VEGF-165.

Placental growth factor (PlGF) has been implicated in pathological angiogenesis. PlGF is structurally related to VEGF and is also a ligand for VEGFR-1. Consequently, VEGF traps comprising the extracellular domain of VEGFR1 (see above) are useful for targeting PlGF. Anti-angiogenic agents further include those that bind to the VEGFR-1/Flt-1 receptor. In certain embodiments, the antigen-binding proteins that bind to the extracellular domain of VEGFR-1 block binding by one or both of its ligands, VEGF and PlGF, and/or neutralize VEGF-induced or PlGF-induced activation of VEGFR-1.

PDGF is composed of four polypeptide chains that form homodimers PDGF-AA, BB, CC, and DD as well as the heterodimer PDGF-AB. The PDGF receptors (PDGFR)-α and -β mediate PDGF functions. Specifically, PDGFRα binds to PDGF-AA, -BB, -AB, and -CC, whereas PDGFRβ interacts with -BB and -DD. Non-limiting examples of PDGF-binding agents include anti-PDGF antibodies and PDGF traps. Agents that target PDGF include Fovista™ (E10030, Ophthotech), a pegylated aptamer targeting PDGF-B, and AX102 (Sennino et al., 2007, Cancer Res. 75(15):7359-67), a DNA oligonucleotide aptamer that binds PDGF-B.

In certain embodiments of the present invention, an antibody or an antigen binding fragment thereof is administered to a subject together with an effective amount of a PDGFRβ antibody Agents that target PDGF receptors include ramucirumab (IMC-3G3, human IgG$_1$) an anti-PDGFRα antibody, crenolanib (CP-868596), a selective inihibitor of PDGFRα (IC$_{50}$=0.9 nM) and PDGFRβ (IC$_{50}$=1.8 nM), and nilotinib (Tasigna®), an inhibitor of PDGFRα and PDGFRβ and other tyrosine kinases.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; GW786034) inhibits VEGFR-1, -2 and -3, cKIT and PDGFR. Foretinib (GSK1363089; XL880) inhibits VEGFR2 and MET, as does cabozantinib (Cometriq; XL184). Ponatinib (Iclusig; AP24534) inhibits VEGFR, PDGFR and c kit. Tivozanib (AV-951) inhibits VEGFR-1, VEGFR-2 and VEGFR-3 at picomolar concentrations. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR.

In certain embodiments, anti-VEGFR antibodies of the invention are coadministered with matrix metalloproteinase inhibitors. Matrix metalloproteases (MMPs), such as MMP-14, MMP-16, and MMP-24, cleave components of the extracellular matrix (ECM) and basement membranes, thereby allowing cancer cells to penetrate and infiltrate the subjacent stromal matrix. Additionally, a number of growth-factor receptors, cell adhesion molecules, chemokines, cytokines, apoptotic ligands, and angiogenic factors are substrates of MMPs. Hence, MMP activity may cause activation of growth factors, suppression of tumor cell apoptosis, destruction of chemokine gradients developed by host immune response, or release of angiogenic factors. MMPs may facilitate tumor growth by promoting the release of cell proliferation factors such as insulin-like growth factors which are bound to specific binding proteins (IGFBPs) (Manes et al., 1997 J. Biol. Chem. 272: 25706-25712).

Collagenases, including MMP-2, have been found at elevated levels in melanoma and in cancers of the colon, breast, lung, prostate, and bladder. Usually, these elevated levels correlate with higher tumor grade and invasiveness. MMP-2 levels are significantly elevated in the serum of patients with metastatic lung cancer, and in those patients with high levels, response to chemotherapy is diminished. MMP-14, which cleaves proMMP-2 to release active MMP-2, is elevated in numerous cancers and can contribute to the growth of tumors, tumor embolism, and the mobility, invasiveness and metastasis of cancer (e.g., CNS tumors (e.g., gliomas), head and neck cancer, oral cavity cancer, laryngeal cancer, chondrosarcoma, breast cancer). MMP-16 and MMP-24 are also elevated in numerous cancers and can contribute to both the growth of tumors and the invasiveness and metastasis of cancer (e.g., breast cancer, laryngeal cancer, ovarian cancer, testicular carcinoma, melanoma, brain tumors (e.g., astrocytomas, glioblastomas, gliomas).

In certain embodiments, anti-VEGFR antibodies of the invention are coadministered with MMP-14 antagonists, including but not limited to anti-MMP-14 antibodies disclosed in U.S. Pat. Nos. 7,745,587 and 8,106,168. In one embodiment, the antibody is human monoclonal antibody DX-2400 (Dyax Corp). Coadministration with such an antibody is suitable for treatment of human carcinomas, including but not limited to, uterine cervix, stomach, lung, breast, colon, head and neck, malignant brain tumors, and melanoma.

In another embodiment, a VEGFR2 antibody of the invention can be administered in combination with one or more suitable adjuvants, such as, for example, cytokines (IL-10 and IL-13, for example) or other immune stimulators. It should be appreciated, however, that administration of only an anti-KDR antibody is sufficient to prevent, inhibit, or reduce the progression of the tumor in a therapeutically effective manner.

Anti-inflammatories and immunosuppressants include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), and mycophenolic acid.

Certain embodiments comprise administering an antibody of the invention and a second agent as follows: docetaxel for solid tumors, including breast cancer and urinary tract and renal cancers, paclitaxel (solid tumors, gastric adenocarcinoma), FOLFRI (i.e, irinotican, folinic acid, 5-Florouracil) for colorectal cancer, capecitabine (breast cancer), FOLFOX (i.e., oxaliplatin, leucovorin, 5-Fluorouracil) (gastric, esophageal, gastroesophageal cancers), eribulin (breast cancer), FOLFIRI (i.e., irinotecan, levofolinate, 5-Fluorouracil) (colorectal carcinoma), carboplatin (NSCLC), mitoxantrone and prednisone (prostate cancer), OFF (oxaliplatin folinic acid, 5-Florouracil) (colorectal cancer), irinotican and cetuximab (colorectal cancer), and dacarbazine (malignant melanoma).

The antibodies and antigen binding fragments of the invention can be conjugated to an agent, e.g., a cytotoxic drug, cytotoxin enzyme, or radioisotope. This method includes administering the binding protein alone or attached to an agent (e.g., a cytotoxic drug), to a subject requiring such treatment. For example, VEGFR2 antibodies or fragments thereof may be used to deliver nanoparticles containing agents, such as toxins, to VEGFR2 associated cells or tissues, e.g., tumors.

The VEGFR2 binding proteins can be used directly in vivo to eliminate antigen-expressing cells via natural complement-dependent cytotoxicity (CDC) or antibody dependent cellular cytotoxicity (ADCC). The binding proteins described herein can include complement binding effector domain, such as the Fc portions from IgG1, -2, or -3 or corresponding portions of IgM which bind complement.

When a VEGFR-2 antibody of the invention is administered with a second agent, the first and second agents can be administered sequentially or simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration includes administering a second agent to a patient in which administration of the first agent did not treat, or did not sufficiently treat, the disease or disease symptom. In other embodiments, adjunctive administration includes administration of the second agent to a patient whose disease has been effectively treated by administration of the first agent.

In one embodiment of the invention, an antibody or an antigen binding fragment thereof is administered by injection, a small molecule administered orally. In one such embodiment, the antibody is administered weekly or once or twice per month and the small molecule is administered daily.

In an embodiment of the invention, an antibody or an antigen binding fragment thereof is administered by injection, and a ROCK2 inhibitor is administered orally. In a preferred embodiment, the agents are administered once daily. According to the invention, when a ROCK inhibitor, or a VEGFR2 antibody are administered to a subject to treat an ocular disease, a TGF-β antagonist can be administered to the subject to reduce or prevent scarring. For example, in an embodiment of the invention, when a ROCK inhibitor is administered to treat an ocular disorder, a TGF-β antagonist is also administered. In another embodiment, when a VEGF antagonist is administered to a subject to treat an ocular disorder, a TGF-β antagonist is also administered. In another embodiment of the invention, when a ROCK inhibitor and a VEGF antagonist are administered to a subject to treat an ocular disorder, a TGF-β antagonist is also administered. In ocular diseases involving neovascularization, leakage of new blood vessels is followed by scar formation (e.g., discaform scar). The invention includes administration of a TGF-β antagonist as well as a VEGF antagonist and a ROCK2 inhibitor to a subject to treat neovascularization in ocular disease.

Useful TGF-β antagonists include, without imitation, the following: (i) anti-TGF-β antibodies and antigen binding fragments thereof, such as pan-TGF-β antibody GC-1008 (Genzyme), anti-TGF-$β_1$ antibody metelimumab (CAT-192) (Cambridge Antibody Technology), and antigen binding fragments of those antibodies, (ii) soluble TGF-β receptors or ligand binding fragments thereof, such as P144, a synthetic peptide encompassing amino acids 730-743 from the membraneproximal ligand-binding domain of TGF-β type III receptor (Esparza-López et al., 2001, J. Biol. Chem. 276(18):14588-96), and a type II TGF-β receptor-Fc ($IgG_1$) fusion (Smith, J. et al., 1999, Circulation Res. 84:1212-22), (iii) peptides that bind to TGF-β receptors that block one or more isoforms of TGF-β, such as the 25 amino acid peptides from TGF-$β_1$, TGF-$β_2$, and TGF-$β_3$ disclosed by Huang et al., 1997, J. Biol. Chem. 272:27155-59, that bind to TGF-β receptors, and (iv) antisense agents that inhibit TGF-β synthesis, such as trabedersen (Antisense Pharma GmbH), an oligonucleotide that inhibits the synthesis of TGF-β2. Additional antagonists are disclosed in WO2006/052568, WO 02/094833, WO 04/048382, WO 04/048381, WO 04/050659, WO 04/021989, WO 04/026871, and WO 04/026307.

In certain embodiments of the present invention, an antibody or an antigen binding fragment thereof is administered to a subject together with an effective amount of a PD-L1 antibody (see U.S. 61/927,907 and PCT/US15/11657, which are incorporated herein by reference in their entirety).

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

Methods of administration include but are not limited to parenteral, intradermal, intravitrial, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream. For treatment of ocular disease, intravitrial administration of biological agents is preferred.

In specific embodiments, it may be desirable to administer a compound locally. This may be achieved, for example, and not by way of limitation, by local infusion, topical application, by injection, by means of a catheter, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Identification of Antibodies that Bind to VEGFR Domains 2 and 3 and Block Ligand Binding.

Figure 3:
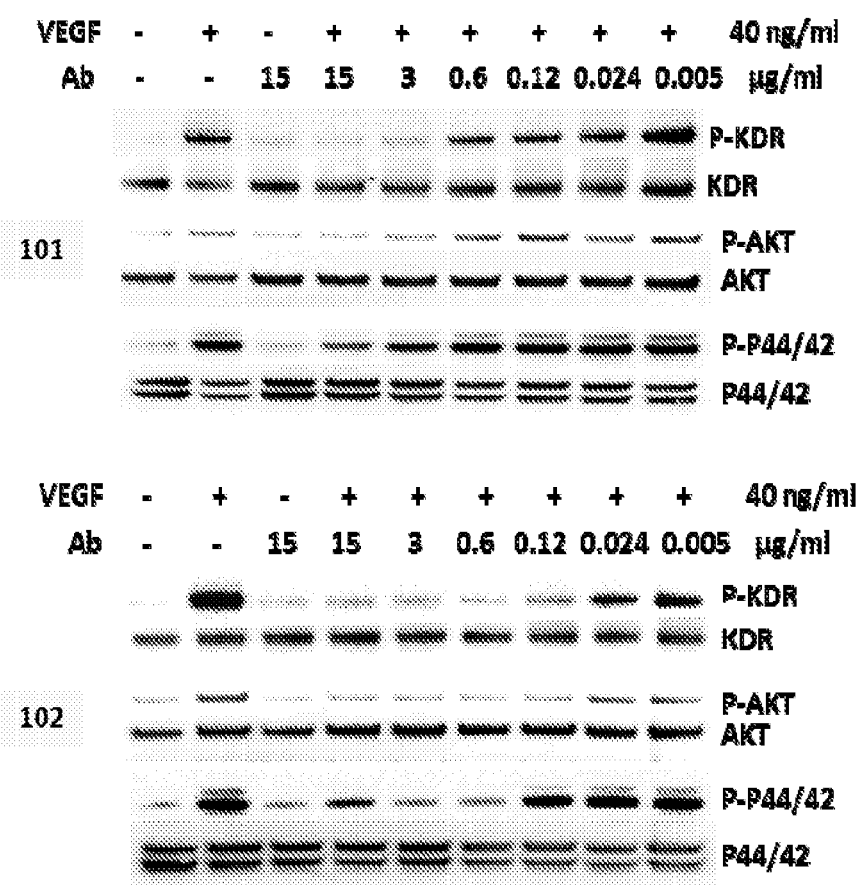
FIG. 3 shows Mabs 101 and 102 of the invention inhibit VEGFA-stimulated phosphorylation of VEGFR2, AKT, and MAPK in porcine aortic endothelial (PAE) cells overexpressing KDR (human VEGFR2).

Two antibodies that bind to and neutralize human VEGFR2, identified in Table 1, were isolated from human Fab phage display libraries. The antibodies block binding of the ligand VEGFA to hVEGFR2 (FIG. 2). The antibodies also bind to porcine aortic endothelial (PAE) cells expressing KDR, and inhibit VEGFA-stimulated phosphorylation of VEGFR2, AKT, and MAPK. (FIG. 3). Table 1 indicates amino acid sequences of the CDRs and variable domains of the antibodies. The $K_d$s of Mab 101 and Mab 102 are about 6.6 mM and 1.7 nM, respectively.

The heavy chain of Mab 101 was reshuffled with κ light chain genes (κ-library) and λ light chain genes (λ-library).

20 unique λ light chain variants were found by panning the λ-library against both human VEGFR2 and mouse VEGFR2. 22 unique κ light chain variants were found by panning the λ-library against both human VEGFR2 and mouse VEGFR2. Table 2 indicates amino acid sequences of the CDRs and variable domains of the light chains. The $K_d$s of Mabs 105, 106, and 107 were increased about 10 fold (0.24 nM, 0.22 nM, and 0.12 nM, respectively) (Table 3). These antibodies, and antibody Mab101 from which they are derived, bind to domains 2 and 3 of VEGFR and to constructs containing those domains.

TABLE 3

Antibody Binding Data

| Antibody | ka $10^4 M^{-1} s^{-1}$ | kd $10^{-4} s^{-1}$ | KD nM |
|---|---|---|---|
| 107 | 55.8 | 0.934 | 0.167 |
| 109 | 30.6 | 3.80 | 1.24 |
| 104 | 79.2 | 1.13 | 0.165 |
| 110 | 44.9 | 3.10 | 0.69 |
| 108 | 71.9 | 1.75 | 0.244 |
| 105 | 24.3 | 0.591 | 0.243 |
| 101 | 29.8 | 5.93 | 1.81 |

Like the parent antibody, these antibodies bind to VEGFR2 and block binding of VEGFA to VEGFR2 (FIG. 4), and inhibit VEGFA-stimulated phosphorylation of VEGFR2, AKT, and MAPK (FIG. 5).

Several of the antibodies, including Mabs 138, 139, 140, and 146, also cross react with mouse VEGFR2.

TABLE 4

Cross Reactivity

| | hVEGFR2 | | | mVEGFR2 | | |
|---|---|---|---|---|---|---|
| Antibody | ka $10^4 M^{-1} s^{-1}$ | kd $10^{-4} s^{-1}$ | KD nM | ka $10^4 M^{-1} s^{-1}$ | kd $10^{-4} s^{-1}$ | KD nM |
| 138 | 19.7 | 1.42 | 0.72 | 23.4 | 5.90 | 2.55 |
| 139 | 14.6 | 1.75 | 1.20 | 13.0 | 3.17 | 2.44 |
| 106 | 35.6 | 0.512 | 0.144 | | | |

Mabs 138, 139, and 140 inhibited VEGFA-stimulated phosphorylation of VEFGR2 and downstream signal transduction molecules, including MAPK.

Example 2

Inhibition of Tumor Growth In Vivo 6 to 8-week-old sex-matched (female) NOD-SCID mice are irradiated with 3.5 Gy from a $^{137}$Cs gamma-ray source at a dose rate of about 0.9 Gy/min and intravenously inoculated with $2 \times 10^7$ HL60 cells. Three days after tumor inoculation, groups of mice are treated twice weekly with various doses of Mab 106 and recorded for time of survival.

All untreated mice died within about two weeks. Even with the high tumor load, the survival time for mice treatment with 10 mg/kg Mab 106 is extended to as much as 28 days.

Example 3

Treatment of Colon Cancer in a Human Patient

Human subjects diagnosed with colon cancer are divided into treatment groups and given the standard chemotherapeutic regimen. Two patient groups are treated weekly with 5 mg/kg/week or 15 mg/kg/week for 4 months. A control group is given only the standard chemotherapeutic regimen. Tumor burden is assessed periodically by magnetic resonance imaging (MRI). Compared to the control group, it is expected that the patients who have received weekly antibody treatments show significant reductions in tumor growth or tumor size, increased delay to progression or prolonged survival compared to patients that do not receive the antibody treatment.

Mab 138 (Table 2), containing the heavy chain of Mab 101 (SEQ ID NO. 4; see FIG. 6A), was selected for affinity maturation. Mutations were introduced into CDR3 of the light chan and CDR1, CDR2, and CDR3 of the heavy chain. The resulting library was panned on human and murine VEGFR2. Table 5 indicates amino acid sequences of the heavy and light chain CDRs and variable domains of five of the resulting antibodies. FIG. 6 shows a comparison of the sequences to the Mab 138 heavy chain (SEQ ID NO. 4) and kappa light chain (i.e. SEQ ID NO:160).

TABLE 5

Antibody Amino Acid Sequences by SEQ ID NO

| Mab # | CDR-H1 | CDR-H2 | CDR-H3 | $V_H$ domain | CDR-L1 | CDR-L2 | CDR-L3 | $V_L$ domain |
|---|---|---|---|---|---|---|---|---|
| 147 (B1C4_A7) | 197 | 198 | 199 | 200 | 201 | 202 | 203 | 204 |
| 148 (B1C4_H9) | 205 | 206 | 207 | 208 | 209 | 210 | 211 | 212 |
| 149 (B1C4_E5) | 213 | 214 | 215 | 216 | 217 | 218 | 219 | 220 |
| 150 (B1C4_A6) | 221 | 222 | 223 | 224 | 225 | 226 | 227 | 228 |
| 151 (B1C4_G3) | 229 | 230 | 231 | 232 | 233 | 234 | 235 | 236 |

The binding constants of Mab 147 and Mab 149 as well as the parent Mab 138 for human, murine, and rat VEGFR2 were determined by Biacore analysis (Table 6).

TABLE 6

Biacore Analysis of Binding to Human, Murine, and Rat VEGFR2

| Mab | antigen | $k_a$ | $k_d$ | $K_D$ |
|---|---|---|---|---|
| 138 | rat | 4.30E+04 | 1.34E−03 | 3.12E−08 |
|  | murine | 2.86E+04 | 2.33E−03 | 8.17E−08 |
|  | human | 8.98E+04 | 6.00E−04 | 6.68E−09 |
| 147 | rat | 6.45E+04 | 8.99E−04 | 1.39E−08 |
|  | murine | 4.38E+04 | 1.28E−03 | 2.94E−08 |
|  | human | 1.13E+05 | 2.82E−04 | 2.51E−09 |
| 149 | rat | 3.32E+04 | 1.43E−03 | 4.31E−08 |
|  | murine | 2.29E+04 | 1.81E−03 | 7.92E−08 |
|  | human | 8.62E+04 | 6.59E−04 | 7.65E−09 |

Figure 7:
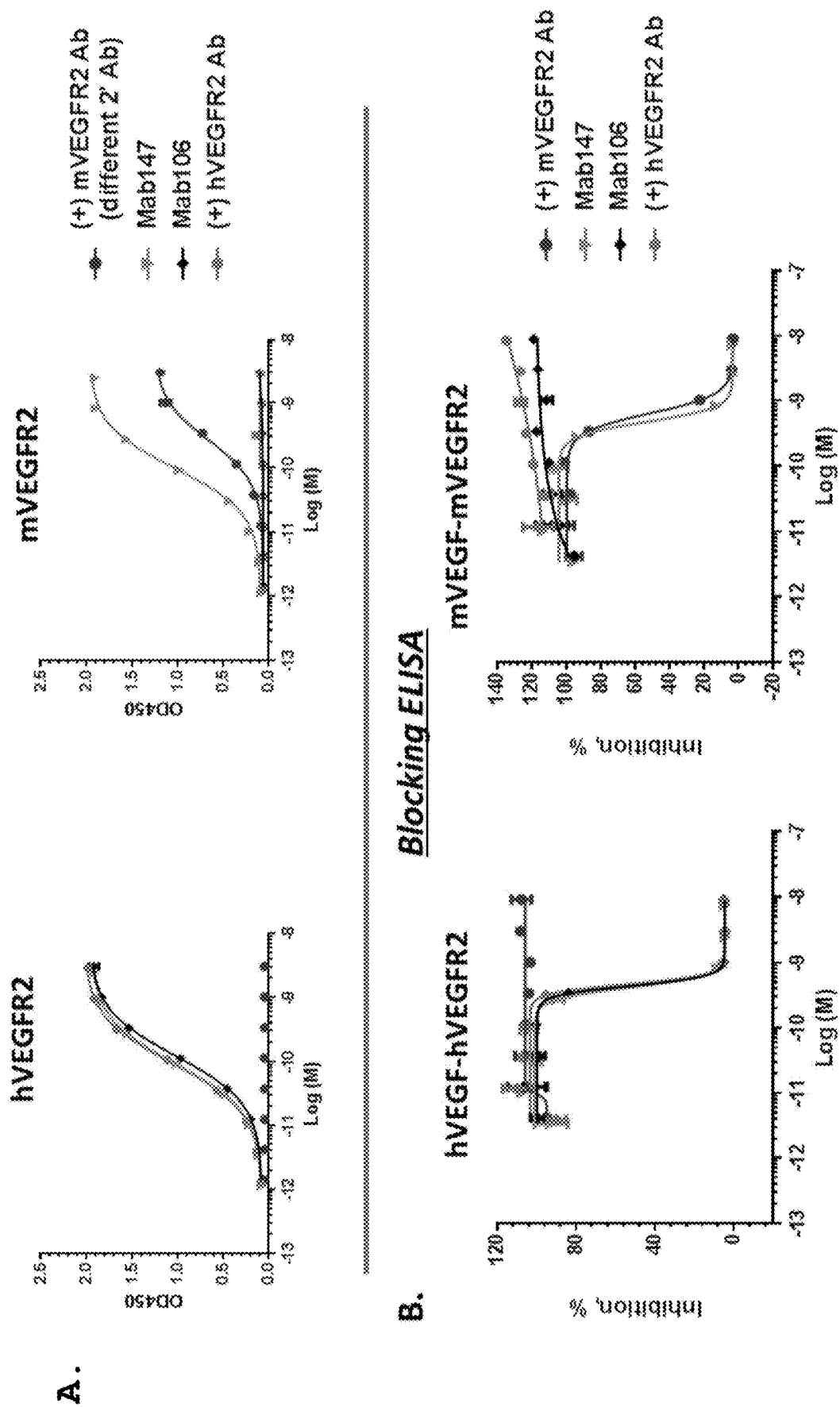
FIG. 7A depicts binding of antibodies of the invention to soluble human and murine VEGFR2 compared to DC101 (a murine monoclonal Ab that binds to murine VEGFR2) and a control antibody that binds only to human VEGFR2. Mab 147 binds to both human and murine VEGFR2. Mab 106 binds to human VEGFR2 but not murine VEGFR2.
FIG. 7B depicts data from ligand blocking experiments. Mab 147 blocks the binding of human VEGF with human VEGFR2 and the binding of murine VEGF with murine VEGFR2. Mab 106 blocks the binding of human VEGF with human VEGFR2 but not the binding of murine VEGF with murine VEGFR2.

Mab 147 was examined by ELISA for its receptor binding and ligand blocking properties. Mab 147 binds to both soluble hVEGFR2 and soluble mVEGFR2 with similar affinity (FIG. 7A). Mab 147 blocks ligand binding to hVEGFR2 similar to a hVEGFR specific control antibody and also blocks ligangd binding to mVEGFR2 similar to a mVEGFR2-specific control antibody (FIG. 7B).

Binding of Mab 147 to hVEGFR2 and mVEGFR2 expressed on cell membranes was also confirmed. FIG. 8A shows binding to hVEGR2 expressed by human umbilical vein entothelial cells (HUVEC) as well as procine aortic endothelial (PAE) cells overexpressing KDR (i.e., human VEGFR2). Mab 147 also bound to mVEGFR expressed by MS1 murine endothelial cells (FIG. 8B).

Figure 10:
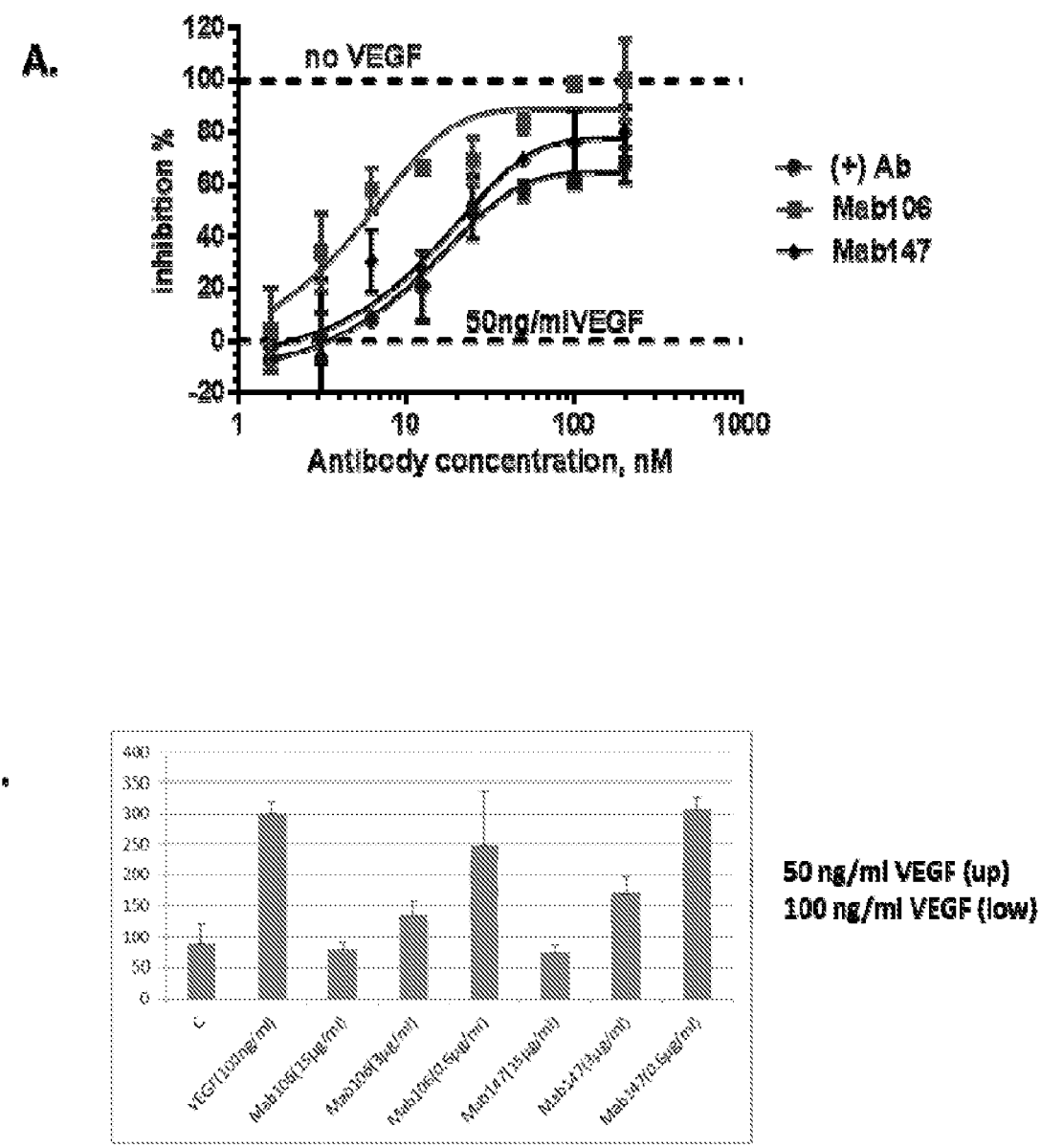
FIG. 10A depicts inhibition of proliferation of KDR-PAE cells by Mab 106, Mab 147, and a control antibody that binds to hVEGFR2.
FIG. 10B shows inhibition of induced cell migration. Migration of KDR-PAE cells was induced with a VEGF gradient (50 ng/ml VEGF (up), 100 ng/ml VEGF (low)). The plot depicts cell counts in the presence of 0.6 µg/ml, 3 µg/ml, or 15 µg/ml of Mab 106 or Mab 147 antibody.
Figure 11:
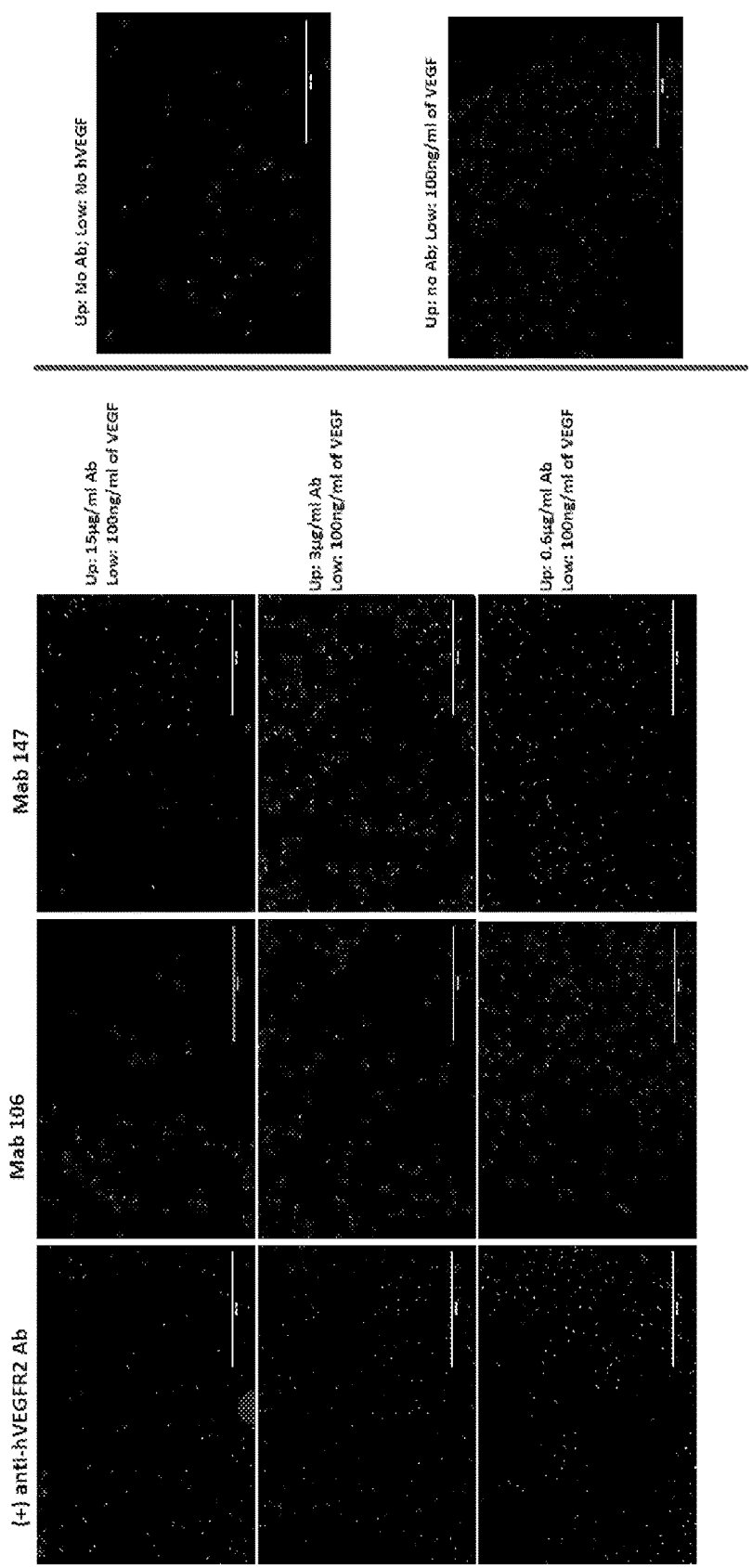
FIG. 11 depicts inhibition of VEGF-induced migration of KDR-PAE cells by Mab 147.

Mab 147 inhibit VEGFR-2 mediated signal transduction, as indicated by reduced phosphorylation of KDR and p42/44 in KDR-PAE cells (FIG. 9A) and in HUVEC cells (FIG. 9B). Mab 106 and Mab 147 inhibit proliferation of KDR-PAE cells (FIG. 10A), as well as inhibit VEGF-induced migration of KDR-PAE cells (FIG. 10B). The effect of Mab 147 on inhibition of VEGF-induced migration by KDR-PAE cells is also shown in FIG. 11.

Mab 147 also inhibits VEGFR-2 mediated signal transduction in murine EOMA cells, as indicated by reduced phosphorylation of mVEGFR2 (FIG. 12A). FACS studies demonstrated that Mab 147 has increased binding to EOMA cells by comparison to control antibodies (FIG. 12B).

We claim:

1. An isolated antibody or antigen binding fragment thereof that binds to human VEGFR2, comprising a heavy chain variable domain, which comprises a CDR1H, a CDR2H, and a CDR3H sequence, and a light chain variable domain, which comprises a CDR1L, a CDR2L, and a CDR3L sequence wherein:
   (i) the CDR1H sequence is GFTFSWYVMG (SEQ ID NO: 237);
   (ii) the CDR2H sequence is SIYPQGGATSYADSVKG (SEQ ID NO: 238);
   (iii) the CDR3H sequence is GNYFDY (SEQ ID NO: 241);
   (iv) the CDR1L sequence is RASQSVSSNYFG (SEQ ID NO: 245);
   (v) the CDR2L sequence is GASSRAT (SEQ ID NO: 246); and
   (vi) the CDR3L sequence is QQFDSLPLT (SEQ ID NO: 247).

2. The antibody or antigen binding fragment of claim 1, wherein the heavy chain variable domain has a sequence that is SEQ ID NO: 200, and wherein the light chain variable domain has a sequence that is SEQ ID NO: 204.

3. The antibody or antigen binding fragment of claim 1, which has isotype IgG.

4. The antibody or antigen binding fragment of claim 1, which is an scFv, Fv, Fab', Fab, F(ab')2, or diabody.

5. The antibody or antigen binding fragment of claim 1, wherein the antibody or antigen binding fragment binds to human VEGFR2 and murine hVEGFR2.

6. The antibody or antigen binding fragment of claim 1, wherein the heavy chain variable domain has a sequence that is at least 85% identical to the sequence of SEQ ID NO: 200, and wherein the light chain variable domain has a sequence that is at least 85% identical to the sequence of SEQ ID NO: 204.

7. A composition comprising an antibody or antigen binding fragment of claim 1, and a pharmaceutically acceptable carrier.

8. A method of neutralizing activation of human VEGFR2 or murine VEGFR2 comprising contacting a cell with an effective amount of an antibody or antigen binding fragment of claim 1.

9. A method of inhibiting angiogenesis associated with tumor growth in a subject in need thereof, the method comprising administering to the subject an effective amount of an antibody or antigen binding fragment of claim 1.

10. A method of reducing tumor growth in a subject in need thereof, the method comprising administering to the subject an effective amount of an antibody or antigen binding fragment of claim 1.

11. The method of claim 10, the method further comprising administering to the subject an antineoplastic agent.

12. The method of claim 10, the method further comprising administering to the subject an anti-inflammatory agent or an immunosuppressant.

13. A method of treating a neoplastic disease in a subject, the method comprising administering to the subject an effective amount of an antibody or antigen binding fragment of claim 1, wherein the neoplastic diseases is selected from the group consisting of lung cancer, colorectal cancer, renal cell carcinoma, glioblastoma, ovarian cancer, bladder cancer, gastric cancer, multiple myeloma, non-small cell lung cancer, and pancreatic cancer.

* * * * *

SEQUENCE LISTING

```
<160> NUMBER OF SEQ ID NOS: 252

<210> SEQ ID NO 1
<211> LENGTH: 7
<212> TYPE: PRT
<213> ORGANISM: Artificial Sequence
<220> FEATURE:
<223> OTHER INFORMATION: Human antibody library

<400> SEQUENCE: 1

Gly Phe Thr Phe Ser Trp Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Human antibody library

<400> SEQUENCE: 2

Ile Tyr Pro Ser Gly Gly Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Human antibody library

<400> SEQUENCE: 3

Gly Asn Tyr Phe Asp Tyr
1               5

<210> SEQ ID NO 4
<211> LENGTH: 115
<212> TYPE: PRT
<213> ORGANISM: Artificial Sequence
<220> FEATURE:
<223> OTHER INFORMATION: Human antibody library

<400> SEQUENCE: 4
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Ser
        115

<210> SEQ ID NO 5
<211> LENGTH: 11
<212> TYPE: PRT
<213> ORGANISM: Artificial Sequence
<220> FEATURE:
<223> OTHER INFORMATION: Human antibody library

<400> SEQUENCE: 5

Gln Gly Asp Ser Leu Arg Ser Tyr Tyr Ala Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Human antibody library

<400> SEQUENCE: 6

Gln Asp Thr Asn Arg Pro Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Human antibody library

<400> SEQUENCE: 7

Gln Ala Trp Asp Ser Asn Thr Ala Val
1               5

<210> SEQ ID NO 8
<211> LENGTH: 109
<212> TYPE: PRT
<213> ORGANISM: Artificial Sequence
<220> FEATURE:
<223> OTHER INFORMATION: Human antibody library

<400> SEQUENCE: 8

Gln Ser Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30
```

-continued

```
Ser Trp Tyr Gln Gln Lys Pro Gly Gln Ser Pro Leu Val Ile Tyr
        35                  40                  45

Gln Asp Thr Asn Arg Pro Ser Gly Ile Pro Glu Arg Phe Ser Gly Ser
 50                  55                  60

Asn Ser Gly Asn Thr Ala Thr Leu Thr Ile Ser Glu Thr Gln Ala Met
 65                  70                  75                  80

Asp Glu Ala Asp Tyr Tyr Cys Gln Ala Trp Asp Ser Asn Thr Ala Val
                 85                  90                  95

Phe Gly Gly Gly Thr Lys Leu Thr Val Leu Gly Gln Pro
                100                 105
```

<210> SEQ ID NO 9
<211> LENGTH: 7
<212> TYPE: PRT
<213> ORGANISM: Artificial Sequence
<220> FEATURE:
<223> OTHER INFORMATION: Human antibody library

<400> SEQUENCE: 9

```
Gly Phe Thr Phe Ser Trp Tyr
 1               5
```

<210> SEQ ID NO 10
<211> LENGTH: 6
<212> TYPE: PRT
<213> ORGANISM: Artificial Sequence
<220> FEATURE:
<223> OTHER INFORMATION: Human antibody library

<400> SEQUENCE: 10

```
Gly Ser Ser Gly Gly Phe
 1               5
```

<210> SEQ ID NO 11
<211> LENGTH: 7
<212> TYPE: PRT
<213> ORGANISM: Artificial Sequence
<220> FEATURE:
<223> OTHER INFORMATION: Human antibody library

<400> SEQUENCE: 11

```
Gly Leu Ala Ala Pro Arg Ser
 1               5
```

<210> SEQ ID NO 12
<211> LENGTH: 116
<212> TYPE: PRT
<213> ORGANISM: Artificial Sequence
<220> FEATURE:
<223> OTHER INFORMATION: Human antibody library

<400> SEQUENCE: 12

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
             20                  25                  30

Ile Met Leu Trp Val Arg Gln Ala Pro Gly Lys Gly Leu Glu Trp Val
         35                  40                  45

Ser Ser Ile Gly Ser Ser Gly Gly Phe Thr Asp Tyr Ala Asp Ser Val
     50                  55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Arg Gly Leu Ala Ala Pro Arg Ser Trp Gly Arg Gly Thr Leu Val
            100                 105                 110

Thr Val Ser Ser
        115

<210> SEQ ID NO 13
<211> LENGTH: 13
<212> TYPE: PRT
<213> ORGANISM: Artificial Sequence
<220> FEATURE:
<223> OTHER INFORMATION: Human antibody library

<400> SEQUENCE: 13

Ser Gly Ser Thr Ser Asn Ile Gly Asn Asn Ala Val Ile
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Human antibody library

<400> SEQUENCE: 14

Tyr Asp Asp Leu Leu Pro Ser
1               5

<210> SEQ ID NO 15
<211> LENGTH: 11
<212> TYPE: PRT
<213> ORGANISM: Artificial Sequence
<220> FEATURE:
<223> OTHER INFORMATION: Human antibody library

<400> SEQUENCE: 15

Ala Ser Trp Asp Asp Asn Leu Asn Gly Pro Leu
1               5                   10

<210> SEQ ID NO 16
<211> LENGTH: 113
<212> TYPE: PRT
<213> ORGANISM: Artificial Sequence
<220> FEATURE:
<223> OTHER INFORMATION: Human antibody library

<400> SEQUENCE: 16

Gln Ser Ala Leu Thr Gln Pro Pro Ser Val Ser Glu Ala Pro Gly Gln
1               5                   10                  15

Arg Val Thr Ile Ser Cys Ser Gly Ser Thr Ser Asn Ile Gly Asn Asn
            20                  25                  30

Ala Val Ile Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala Asp Tyr Tyr Cys Ala Ser Trp Asp Asp Asn Leu
                85                  90                  95

Asn Gly Pro Leu Phe Gly Gly Gly Thr Lys Leu Thr Val Leu Arg Gln
            100                 105                 110

Pro

<210> SEQ ID NO 17
<211> LENGTH: 13
<212> TYPE: PRT
<213> ORGANISM: Artificial Sequence
<220> FEATURE:
<223> OTHER INFORMATION: Human antibody library

<400> SEQUENCE: 17

Ser Gly Ser Ser Ser Asn Ile Gly Thr Tyr Pro Val Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Human antibody library

<400> SEQUENCE: 18

Ser Thr Asp Gln Arg Pro Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Human antibody library

<400> SEQUENCE: 19

Gln Ala Trp Asp Ser Ser Thr Val Val
1               5

<210> SEQ ID NO 20
<211> LENGTH: 111
<212> TYPE: PRT
<213> ORGANISM: Artificial Sequence
<220> FEATURE:
<223> OTHER INFORMATION: Human antibody library

<400> SEQUENCE: 20

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Tyr
                20                  25                  30

Pro Val Asn Trp Tyr Gln Gln Leu Pro Gly Ala Ala Pro Lys Leu Leu
            35                  40                  45

Ile Tyr Ser Thr Asp Gln Arg Pro Ser Gly Val Pro Asp Arg Phe Ser
    50                  55                  60

Gly Ser Asn Ser Gly Asn Thr Ala Thr Leu Thr Ile Ser Gly Thr Gln
65                  70                  75                  80

Ala Met Asp Glu Ala Asp Tyr Tyr Cys Gln Ala Trp Asp Ser Ser Thr
                85                  90                  95

Val Val Phe Gly Gly Gly Thr Lys Leu Thr Val Leu Gly Gln Pro
                100                 105                 110

<210> SEQ ID NO 21
<211> LENGTH: 11
<212> TYPE: PRT
<213> ORGANISM: Artificial Sequence
<220> FEATURE:

<223> OTHER INFORMATION: Human antibody library

<400> SEQUENCE: 21

Ser Gly Asp Lys Leu Gly Asp Glu Tyr Ala Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Human antibody library

<400> SEQUENCE: 22

Gln Asp Asn Lys Arg Pro Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Human antibody library

<400> SEQUENCE: 23

Gln Ala Trp Asp Ser Ser Thr Val Val
1               5

<210> SEQ ID NO 24
<211> LENGTH: 109
<212> TYPE: PRT
<213> ORGANISM: Artificial Sequence
<220> FEATURE:
<223> OTHER INFORMATION: Human antibody library

<400> SEQUENCE: 24

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Asp Glu Tyr Ala
                20                  25                  30

Ser Trp Tyr Gln Gln Lys Pro Gly Gln Ser Pro Val Leu Val Ile Tyr
            35                  40                  45

Gln Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly Gln Pro
            100                 105

<210> SEQ ID NO 25
<211> LENGTH: 11
<212> TYPE: PRT
<213> ORGANISM: Artificial Sequence
<220> FEATURE:
<223> OTHER INFORMATION: Human antibody library

<400> SEQUENCE: 25

Ser Gly Asp Asn Leu Arg His Glu Tyr Ser Ser
1               5                   10

<210> SEQ ID NO 26

```
<211> LENGTH: 7
<212> TYPE: PRT
<213> ORGANISM: Artificial Sequence
<220> FEATURE:
<223> OTHER INFORMATION: Human antibody library

<400> SEQUENCE: 26

Gln Asp Ser Lys Arg Pro Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Human antibody library

<400> SEQUENCE: 27

Gln Ala Trp Gly Ser Ser Thr Val Val
1               5

<210> SEQ ID NO 28
<211> LENGTH: 109
<212> TYPE: PRT
<213> ORGANISM: Artificial Sequence
<220> FEATURE:
<223> OTHER INFORMATION: Human antibody library

<400> SEQUENCE: 28

Gln Tyr Glu Leu Thr Gln Pro Pro Ser Val Ser Val Ser Pro Gly Gln
1               5                   10                  15

Thr Ala Ser Ile Thr Cys Ser Gly Asp Asn Leu Arg His Glu Tyr Ser
            20                  25                  30

Ser Trp Tyr Gln Gln Arg Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Gly Ser Ser Thr Val Val
                85                  90                  95

Phe Gly Gly Gly Thr Lys Leu Thr Val Leu Arg Gln Pro
            100                 105

<210> SEQ ID NO 29
<211> LENGTH: 11
<212> TYPE: PRT
<213> ORGANISM: Artificial Sequence
<220> FEATURE:
<223> OTHER INFORMATION: Human antibody library

<400> SEQUENCE: 29

Ser Gly Glu Lys Leu Gly Asp Glu Tyr Ala Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Human antibody library

<400> SEQUENCE: 30

Gln Asp Asn Lys Arg Pro Ser
```

```
1               5

<210> SEQ ID NO 31
<211> LENGTH: 9
<212> TYPE: PRT
<213> ORGANISM: Artificial Sequence
<220> FEATURE:
<223> OTHER INFORMATION: Human antibody library

<400> SEQUENCE: 31

Gln Ala Trp Asp Ser Ser Thr Leu Leu
1               5

<210> SEQ ID NO 32
<211> LENGTH: 109
<212> TYPE: PRT
<213> ORGANISM: Artificial Sequence
<220> FEATURE:
<223> OTHER INFORMATION: Human antibody library

<400> SEQUENCE: 32

Gln Ser Val Leu Thr Gln Pro Pro Ser Val Ser Val Ser Pro Gly Gln
1               5                   10                  15

Thr Ala Ser Ile Thr Cys Ser Gly Glu Lys Leu Gly Asp Glu Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Leu Leu
                85                  90                  95

Phe Gly Gly Gly Thr Lys Leu Thr Val Leu Gly Gln Pro
            100                 105

<210> SEQ ID NO 33
<211> LENGTH: 11
<212> TYPE: PRT
<213> ORGANISM: Artificial Sequence
<220> FEATURE:
<223> OTHER INFORMATION: from human Fab library

<400> SEQUENCE: 33

Ser Gly Glu Lys Leu Gly Asp Glu Tyr Ala Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: from human Fab library

<400> SEQUENCE: 34

Gln Asp Asn Lys Arg Pro Ser
1               5

<210> SEQ ID NO 35
<211> LENGTH: 9
<212> TYPE: PRT
<213> ORGANISM: Artificial Sequence
<220> FEATURE:
<223> OTHER INFORMATION: from human Fab library
```

<400> SEQUENCE: 35

Gln Ala Trp Asp Ser Ser Thr Leu Leu
1               5

<210> SEQ ID NO 36
<211> LENGTH: 109
<212> TYPE: PRT
<213> ORGANISM: Artificial Sequence
<220> FEATURE:
<223> OTHER INFORMATION: from human Fab library

<400> SEQUENCE: 36

Gln Ser Glu Leu Thr Gln Pro Pro Ser Val Ser Val Ser Pro Gly Gln
1               5                   10                  15

Thr Ala Ser Ile Thr Cys Ser Gly Glu Lys Leu Gly Asp Glu Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Leu Leu
                85                  90                  95

Phe Gly Gly Gly Thr Lys Leu Thr Val Leu Gly Gln Pro
            100                 105

<210> SEQ ID NO 37
<211> LENGTH: 11
<212> TYPE: PRT
<213> ORGANISM: Artificial Sequence
<220> FEATURE:
<223> OTHER INFORMATION: Human antibody library

<400> SEQUENCE: 37

Thr Gly Asp Lys Leu Gly Asp Gln Phe Ala Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Human antibody library

<400> SEQUENCE: 38

Gln Asn Asp Lys Arg Pro Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Human antibody library

<400> SEQUENCE: 39

Gln Ala Trp Asp Phe Ser Ser Ala Leu
1               5

<210> SEQ ID NO 40
<211> LENGTH: 109

<212> TYPE: PRT
<213> ORGANISM: Artificial Sequence
<220> FEATURE:
<223> OTHER INFORMATION: Human antibody library

<400> SEQUENCE: 40

Gln Tyr Glu Leu Thr Gln Pro Pro Ser Val Ser Val Ser Pro Gly Gln
1               5                   10                  15

Thr Ala Thr Ile Thr Cys Thr Gly Asp Lys Leu Gly Asp Gln Phe Ala
            20                  25                  30

Ser Trp Tyr Gln His Lys Pro Gly Gln Ser Pro Ile Leu Leu Ile Tyr
        35                  40                  45

Gln Asn Asp Lys Arg Pro Ser Gly Ile Pro Asp Arg Phe Ser Gly Ser
    50                  55                  60

Asp Ser Gly Asn Thr Ala Thr Leu Thr Ile Ser Gly Thr Gln Ala Met
65                  70                  75                  80

Asp Glu Ala His Tyr Tyr Cys Gln Ala Trp Asp Phe Ser Ser Ala Leu
                85                  90                  95

Phe Gly Gly Gly Thr Lys Leu Thr Val Leu Gly Gln Pro
            100                 105

<210> SEQ ID NO 41
<211> LENGTH: 11
<212> TYPE: PRT
<213> ORGANISM: Artificial Sequence
<220> FEATURE:
<223> OTHER INFORMATION: Human antibody library

<400> SEQUENCE: 41

Ser Gly Gln Ile Leu Gly Glu Arg Ser Ala Ser
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Human antibody library

<400> SEQUENCE: 42

Gln Ser Ser Gln Arg Pro Ser
1               5

<210> SEQ ID NO 43
<211> LENGTH: 8
<212> TYPE: PRT
<213> ORGANISM: Artificial Sequence
<220> FEATURE:
<223> OTHER INFORMATION: Human antibody library

<400> SEQUENCE: 43

Gln Thr Trp Asp Thr Ser Ile Leu
1               5

<210> SEQ ID NO 44
<211> LENGTH: 108
<212> TYPE: PRT
<213> ORGANISM: Artificial Sequence
<220> FEATURE:
<223> OTHER INFORMATION: Human antibody library

<400> SEQUENCE: 44

Gln Ser Ala Leu Thr Gln Pro Pro Ser Val Ser Val Ser Pro Gly His
1               5                   10                  15

```
Thr Ala Thr Ile Thr Cys Ser Gly Gln Ile Leu Gly Glu Arg Ser Ala
            20                  25                  30

Ser Trp Tyr Gln Gln Arg Pro Gly Gln Ala Pro Val Leu Val Leu Tyr
        35                  40                  45

Gln Ser Ser Gln Arg Pro Ser Gly Ile Pro Glu Arg Phe Ser Gly Ser
    50                  55                  60

Ile Ser Gly Asn Thr Ala Thr Leu Thr Ile Ser Gly Ala Gln Ser Ile
65                  70                  75                  80

Asp Glu Ala Asp Tyr Tyr Cys Gln Thr Trp Asp Thr Ser Ile Leu Phe
                85                  90                  95

Gly Gly Gly Thr Lys Leu Thr Val Leu Ser Gln Pro
            100                 105
```

<210> SEQ ID NO 45
<211> LENGTH: 11
<212> TYPE: PRT
<213> ORGANISM: Artificial Sequence
<220> FEATURE:
<223> OTHER INFORMATION: Human antibody library

<400> SEQUENCE: 45

```
Ser Gly Asp Ala Leu Gly Asn Asn Tyr Ala Ser
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: Human antibody library

<400> SEQUENCE: 46

```
Gln Asp Thr Lys Arg Pro Ser
1               5
```

<210> SEQ ID NO 47
<211> LENGTH: 10
<212> TYPE: PRT
<213> ORGANISM: Artificial Sequence
<220> FEATURE:
<223> OTHER INFORMATION: Human antibody library

<400> SEQUENCE: 47

```
Gln Thr Trp Asp Arg Asn Thr Pro Tyr Val
1               5                   10
```

<210> SEQ ID NO 48
<211> LENGTH: 110
<212> TYPE: PRT
<213> ORGANISM: Artificial Sequence
<220> FEATURE:
<223> OTHER INFORMATION: Human antibody library

<400> SEQUENCE: 48

```
Gln Ser Ala Leu Thr Gln Pro Pro Ser Val Ser Val Ser Pro Gly Gln
1               5                   10                  15

Thr Ala Ile Ile Thr Cys Ser Gly Asp Ala Leu Gly Asn Asn Tyr Ala
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60
```

```
Ser Ser Gly Asn Thr Ala Thr Leu Thr Ile Ser Glu Thr Gln Thr Met
 65                  70                  75                  80

Asp Glu Ala Asp Tyr Tyr Cys Gln Thr Trp Asp Arg Asn Thr Pro Tyr
                 85                  90                  95

Val Phe Gly Ala Gly Thr Lys Val Thr Val Leu Gly Gln Pro
            100                 105                 110

<210> SEQ ID NO 49
<211> LENGTH: 13
<212> TYPE: PRT
<213> ORGANISM: Artificial Sequence
<220> FEATURE:
<223> OTHER INFORMATION: Human antibody library

<400> SEQUENCE: 49

Ser Gly Ser Ser Ser Asn Ile Gly Thr Asn Thr Leu Asn
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Human antibody library

<400> SEQUENCE: 50

Ala Asn Asn Gln Arg Pro Ser
1               5

<210> SEQ ID NO 51
<211> LENGTH: 11
<212> TYPE: PRT
<213> ORGANISM: Artificial Sequence
<220> FEATURE:
<223> OTHER INFORMATION: Human antibody library

<400> SEQUENCE: 51

Ala Thr Trp Asp Asp Ser Leu Ile Gly Pro Val
1               5                   10

<210> SEQ ID NO 52
<211> LENGTH: 113
<212> TYPE: PRT
<213> ORGANISM: Artificial Sequence
<220> FEATURE:
<223> OTHER INFORMATION: Human antibody library

<400> SEQUENCE: 52

Gln Ser Ala Leu Thr Gln Pro Pro Ser Val Ser Gly Thr Pro Gly Gln
1               5                   10                  15

Arg Val Thr Ile Ser Cys Ser Gly Ser Ser Ser Asn Ile Gly Thr Asn
             20                  25                  30

Thr Leu Asn Trp Tyr Gln Gln Leu Pro Gly Thr Ala Pro Lys Leu Leu
         35                  40                  45

Ile Tyr Ala Asn Asn Gln Arg Pro Ser Gly Val Pro Asp Arg Phe Ser
     50                  55                  60

Gly Ser Arg Ser Gly Thr Ser Ala Ser Leu Ala Ile Ser Gly Leu Gln
 65                  70                  75                  80

Ser Asp Asp Glu Ala Asp Tyr Tyr Cys Ala Thr Trp Asp Asp Ser Leu
                 85                  90                  95

Ile Gly Pro Val Phe Gly Gly Gly Thr Lys Leu Thr Val Leu Gly Gln
            100                 105                 110
```

Pro

<210> SEQ ID NO 53
<211> LENGTH: 13
<212> TYPE: PRT
<213> ORGANISM: Artificial Sequence
<220> FEATURE:
<223> OTHER INFORMATION: from human Fab library

<400> SEQUENCE: 53

Ser Gly Ser Thr Ser Asn Ile Gly Asn Asn Ala Val Ile
1               5                   10

<210> SEQ ID NO 54
<211> LENGTH: 7
<212> TYPE: PRT
<213> ORGANISM: Artificial Sequence
<220> FEATURE:
<223> OTHER INFORMATION: from human Fab library

<400> SEQUENCE: 54

Tyr Asp Asp Leu Leu Pro Ser
1               5

<210> SEQ ID NO 55
<211> LENGTH: 11
<212> TYPE: PRT
<213> ORGANISM: Artificial Sequence
<220> FEATURE:
<223> OTHER INFORMATION: from human Fab library

<400> SEQUENCE: 55

Ala Ser Trp Asp Asp Asn Leu Asn Gly Pro Leu
1               5                   10

<210> SEQ ID NO 56
<211> LENGTH: 113
<212> TYPE: PRT
<213> ORGANISM: Artificial Sequence
<220> FEATURE:
<223> OTHER INFORMATION: from human Fab library

<400> SEQUENCE: 56

Gln Tyr Glu Leu Thr Gln Pro Pro Ser Val Ser Glu Ala Pro Gly Gln
1               5                   10                  15

Arg Val Thr Ile Ser Cys Ser Gly Ser Thr Ser Asn Ile Gly Asn Asn
                20                  25                  30

Ala Val Ile Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala Asp Tyr Tyr Cys Ala Ser Trp Asp Asp Asn Leu
                85                  90                  95

Asn Gly Pro Leu Phe Gly Gly Gly Thr Lys Leu Thr Val Leu Arg Gln
            100                 105                 110

Pro

<210> SEQ ID NO 57
<211> LENGTH: 13
<212> TYPE: PRT

```
<213> ORGANISM: Artificial Sequence
<220> FEATURE:
<223> OTHER INFORMATION: Human antibody library

<400> SEQUENCE: 57

Ser Gly Ser Ser Ser Asn Leu Gly Ser Asn Thr Val Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Human antibody library

<400> SEQUENCE: 58

Thr Asn Ser Gln Arg Pro Ser
1               5

<210> SEQ ID NO 59
<211> LENGTH: 11
<212> TYPE: PRT
<213> ORGANISM: Artificial Sequence
<220> FEATURE:
<223> OTHER INFORMATION: Human antibody library

<400> SEQUENCE: 59

Ala Ala Trp Asp Asp Ser Leu Asn Gly Trp Val
1               5                   10

<210> SEQ ID NO 60
<211> LENGTH: 113
<212> TYPE: PRT
<213> ORGANISM: Artificial Sequence
<220> FEATURE:
<223> OTHER INFORMATION: Human antibody library

<400> SEQUENCE: 60

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Ser Gln Arg Pro Ser Gly Val Pro Asp Arg Phe Ser
    50                  55                  60

Gly Leu Gln Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Ser Gln
            100                 105                 110

Pro

<210> SEQ ID NO 61
<211> LENGTH: 13
<212> TYPE: PRT
<213> ORGANISM: Artificial Sequence
<220> FEATURE:
<223> OTHER INFORMATION: Human antibody library

<400> SEQUENCE: 61

Ser Gly Ser Ser Ser Asn Ile Glu Ser Asn Tyr Val Tyr
```

<210> SEQ ID NO 62
<211> LENGTH: 7
<212> TYPE: PRT
<213> ORGANISM: Artificial Sequence
<220> FEATURE:
<223> OTHER INFORMATION: Human antibody library

<400> SEQUENCE: 62

Thr Asn Asn Gln Arg Pro Ser
1               5

<210> SEQ ID NO 63
<211> LENGTH: 11
<212> TYPE: PRT
<213> ORGANISM: Artificial Sequence
<220> FEATURE:
<223> OTHER INFORMATION: Human antibody library

<400> SEQUENCE: 63

Ala Ser Trp Asp Asp Ser Leu Ser Gly Val Val
1               5                   10

<210> SEQ ID NO 64
<211> LENGTH: 113
<212> TYPE: PRT
<213> ORGANISM: Artificial Sequence
<220> FEATURE:
<223> OTHER INFORMATION: Human antibody library

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Glu Ser Asn
                20                  25                  30

Tyr Val Tyr Trp Tyr Gln Gln Leu Pro Gly Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Val Val Phe Gly Gly Gly Thr Lys Leu Thr Val Leu Arg Gln
            100                 105                 110

Pro

<210> SEQ ID NO 65
<211> LENGTH: 14
<212> TYPE: PRT
<213> ORGANISM: Artificial Sequence
<220> FEATURE:
<223> OTHER INFORMATION: Human antibody library

<400> SEQUENCE: 65

Thr Gly Ser Ser Asn Asp Ile Gly Ser Tyr Asp Tyr Val Ser
1               5                   10

<210> SEQ ID NO 66
<211> LENGTH: 7
<212> TYPE: PRT
<213> ORGANISM: Artificial Sequence

```
<220> FEATURE:
<223> OTHER INFORMATION: Human antibody library

<400> SEQUENCE: 66

Asp Val Asn Asn Arg Pro Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Human antibody library

<400> SEQUENCE: 67

Met Ser Tyr Thr Ile Thr Ala Leu Leu
1               5

<210> SEQ ID NO 68
<211> LENGTH: 112
<212> TYPE: PRT
<213> ORGANISM: Artificial Sequence
<220> FEATURE:
<223> OTHER INFORMATION: Human antibody library

<400> SEQUENCE: 68

Gln Ser Glu Leu Thr Gln Pro Asp Ser Val Ser Gly Ser Pro Gly Gln
1               5                   10                  15

Ser Ile Thr Ile Ser Cys Thr Gly Ser Ser Asn Asp Ile Gly Ser Tyr
            20                  25                  30

Asp Tyr Val Ser Trp Tyr Gln Gln His Pro Gly Arg Ala Pro Lys Phe
        35                  40                  45

Ile Leu Tyr Asp Val Asn Asn Arg Pro Ser Gly Val Ala Asp Arg Phe
    50                  55                  60

Ser Gly Phe Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Ala Leu Leu Phe Gly Gly Gly Thr Arg Val Thr Val Leu Gly Gln Pro
            100                 105                 110

<210> SEQ ID NO 69
<211> LENGTH: 14
<212> TYPE: PRT
<213> ORGANISM: Artificial Sequence
<220> FEATURE:
<223> OTHER INFORMATION: Human antibody library

<400> SEQUENCE: 69

Thr Gly Ser Ser His Asp Ile Gly Ser Tyr Asp Tyr Val Ser
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Human antibody library

<400> SEQUENCE: 70

Asp Val Asn Asn Arg Pro Ser
1               5
```

```
<210> SEQ ID NO 71
<211> LENGTH: 9
<212> TYPE: PRT
<213> ORGANISM: Artificial Sequence
<220> FEATURE:
<223> OTHER INFORMATION: Human antibody library

<400> SEQUENCE: 71

Met Ser Tyr Thr Ile Thr Thr Leu Leu
1               5

<210> SEQ ID NO 72
<211> LENGTH: 112
<212> TYPE: PRT
<213> ORGANISM: Artificial Sequence
<220> FEATURE:
<223> OTHER INFORMATION: Human antibody library

<400> SEQUENCE: 72

Gln Ser Ala Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ser Tyr
            20                  25                  30

Asp Tyr Val Ser Trp Tyr Gln Tyr His Pro Gly Lys Ala Pro Lys Phe
        35                  40                  45

Ile Leu Tyr Asp Val Asn Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 73
<211> LENGTH: 14
<212> TYPE: PRT
<213> ORGANISM: Artificial Sequence
<220> FEATURE:
<223> OTHER INFORMATION: Human antibody library

<400> SEQUENCE: 73

Ala Gly Thr Ser Ser Asp Val Gly Ala Tyr Asp Tyr Val Ser
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Human antibody library

<400> SEQUENCE: 74

Asp Val Tyr Asn Arg Pro Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Human antibody library

<400> SEQUENCE: 75
```

```
Met Ser Tyr Thr Ile Thr Thr Leu Leu
1               5

<210> SEQ ID NO 76
<211> LENGTH: 112
<212> TYPE: PRT
<213> ORGANISM: Artificial Sequence
<220> FEATURE:
<223> OTHER INFORMATION: Human antibody library

<400> SEQUENCE: 76

Gln Ser Ala Leu Thr Gln Pro Ala Ser Met Ser Gly Ser Arg Gly Gln
1               5                   10                  15

Ser Ile Thr Ile Ser Cys Ala Gly Thr Ser Ser Asp Val Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 77
<211> LENGTH: 14
<212> TYPE: PRT
<213> ORGANISM: Artificial Sequence
<220> FEATURE:
<223> OTHER INFORMATION: Human antibody library

<400> SEQUENCE: 77

Thr Gly Ser Ser His Asp Ile Gly Ala Tyr Asp Tyr Val Ser
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Human antibody library

<400> SEQUENCE: 78

Asp Val Tyr Asn Arg Pro Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Human antibody library

<400> SEQUENCE: 79

Met Ser Tyr Thr Ile Thr Thr Leu Leu
1               5

<210> SEQ ID NO 80
<211> LENGTH: 112
<212> TYPE: PRT
<213> ORGANISM: Artificial Sequence
<220> FEATURE:
```

<223> OTHER INFORMATION: Human antibody library

<400> SEQUENCE: 80

Gln Ser Val Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 81
<211> LENGTH: 14
<212> TYPE: PRT
<213> ORGANISM: Artificial Sequence
<220> FEATURE:
<223> OTHER INFORMATION: from human Fab library

<400> SEQUENCE: 81

Thr Gly Ser Ser His Asp Ile Gly Ala Tyr Asp Tyr Val Ser
1               5                   10

<210> SEQ ID NO 82
<211> LENGTH: 7
<212> TYPE: PRT
<213> ORGANISM: Artificial Sequence
<220> FEATURE:
<223> OTHER INFORMATION: from human Fab library

<400> SEQUENCE: 82

Asp Val Tyr Asn Arg Pro Ser
1               5

<210> SEQ ID NO 83
<211> LENGTH: 9
<212> TYPE: PRT
<213> ORGANISM: Artificial Sequence
<220> FEATURE:
<223> OTHER INFORMATION: from human Fab library

<400> SEQUENCE: 83

Met Ser Tyr Thr Ile Thr Thr Leu Leu
1               5

<210> SEQ ID NO 84
<211> LENGTH: 112
<212> TYPE: PRT
<213> ORGANISM: Artificial Sequence
<220> FEATURE:
<223> OTHER INFORMATION: from human Fab library

<400> SEQUENCE: 84

Gln Ser Val Leu Thr Gln Pro Ala Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
          35                  40                  45

Ile Leu Tyr Asp Val Tyr Asn Arg Pro Ser Gly Val Ser Asp Arg Phe
      50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 85
<211> LENGTH: 14
<212> TYPE: PRT
<213> ORGANISM: Artificial Sequence
<220> FEATURE:
<223> OTHER INFORMATION: from human Fab library

<400> SEQUENCE: 85

Thr Gly Ser Ser His Asp Ile Gly Ala Tyr Asp Tyr Val Ser
1               5                   10

<210> SEQ ID NO 86
<211> LENGTH: 7
<212> TYPE: PRT
<213> ORGANISM: Artificial Sequence
<220> FEATURE:
<223> OTHER INFORMATION: from human Fab library

<400> SEQUENCE: 86

Asp Val Tyr Asn Arg Pro Ser
1               5

<210> SEQ ID NO 87
<211> LENGTH: 9
<212> TYPE: PRT
<213> ORGANISM: Artificial Sequence
<220> FEATURE:
<223> OTHER INFORMATION: from human Fab library

<400> SEQUENCE: 87

Met Ser Tyr Thr Ile Thr Thr Leu Leu
1               5

<210> SEQ ID NO 88
<211> LENGTH: 112
<212> TYPE: PRT
<213> ORGANISM: Artificial Sequence
<220> FEATURE:
<223> OTHER INFORMATION: from human Fab library

<400> SEQUENCE: 88

Gln Ser Val Leu Thr Gln Pro Tyr Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
          35                  40                  45

Ile Leu Tyr Asp Val Tyr Asn Arg Pro Ser Gly Val Ser Asp Arg Phe
      50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 89
<211> LENGTH: 14
<212> TYPE: PRT
<213> ORGANISM: Artificial Sequence
<220> FEATURE:
<223> OTHER INFORMATION: Human antibody library

<400> SEQUENCE: 89

Thr Gly Ser Ser His Asp Ile Gly Ala Tyr Asp Tyr Val Ser
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Human antibody library

<400> SEQUENCE: 90

Asp Val Tyr Asn Arg Pro Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Human antibody library

<400> SEQUENCE: 91

Met Ser Tyr Thr Ile Thr Thr Leu Leu
1               5

<210> SEQ ID NO 92
<211> LENGTH: 112
<212> TYPE: PRT
<213> ORGANISM: Artificial Sequence
<220> FEATURE:
<223> OTHER INFORMATION: Human antibody library

<400> SEQUENCE: 92

Gln Ser Ala Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 93

```
<211> LENGTH: 14
<212> TYPE: PRT
<213> ORGANISM: Artificial Sequence
<220> FEATURE:
<223> OTHER INFORMATION: from human Fab library

<400> SEQUENCE: 93

Thr Gly Ser Ser His Asp Ile Gly Ala Tyr Asp Tyr Val Ser
1               5                   10

<210> SEQ ID NO 94
<211> LENGTH: 7
<212> TYPE: PRT
<213> ORGANISM: Artificial Sequence
<220> FEATURE:
<223> OTHER INFORMATION: from human Fab library

<400> SEQUENCE: 94

Asp Val Tyr Asn Arg Pro Ser
1               5

<210> SEQ ID NO 95
<211> LENGTH: 9
<212> TYPE: PRT
<213> ORGANISM: Artificial Sequence
<220> FEATURE:
<223> OTHER INFORMATION: from human Fab library

<400> SEQUENCE: 95

Met Ser Tyr Thr Ile Thr Thr Leu Leu
1               5

<210> SEQ ID NO 96
<211> LENGTH: 112
<212> TYPE: PRT
<213> ORGANISM: Artificial Sequence
<220> FEATURE:
<223> OTHER INFORMATION: from human Fab library

<400> SEQUENCE: 96

Gln Ser Glu Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 97
<211> LENGTH: 12
<212> TYPE: PRT
<213> ORGANISM: Artificial Sequence
<220> FEATURE:
<223> OTHER INFORMATION: Human antibody library

<400> SEQUENCE: 97

Arg Ala Ser Gln Ser Val Ser Ser Ser Tyr Leu Ala
```

-continued

<210> SEQ ID NO 98
<211> LENGTH: 7
<212> TYPE: PRT
<213> ORGANISM: Artificial Sequence
<220> FEATURE:
<223> OTHER INFORMATION: Human antibody library

<400> SEQUENCE: 98

Gly Ala Ser Ser Arg Ala Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Human antibody library

<400> SEQUENCE: 99

Gln Gln Phe Asp Ser Ser Pro Pro Thr
1               5

<210> SEQ ID NO 100
<211> LENGTH: 109
<212> TYPE: PRT
<213> ORGANISM: Artificial Sequence
<220> FEATURE:
<223> OTHER INFORMATION: Human antibody library

<400> SEQUENCE: 100

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 101
<211> LENGTH: 12
<212> TYPE: PRT
<213> ORGANISM: Artificial Sequence
<220> FEATURE:
<223> OTHER INFORMATION: Human antibody library

<400> SEQUENCE: 101

Arg Ala Ser Glu Arg Ile Ser Ser Asn Tyr Leu Met
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Human antibody library

<400> SEQUENCE: 102

Gly Ala Ser Ile Arg Ala Thr
1               5

<210> SEQ ID NO 103
<211> LENGTH: 9
<212> TYPE: PRT
<213> ORGANISM: Artificial Sequence
<220> FEATURE:
<223> OTHER INFORMATION: Human antibody library

<400> SEQUENCE: 103

Gln Gln Tyr Tyr Ser Ser Pro Leu Thr
1               5

<210> SEQ ID NO 104
<211> LENGTH: 109
<212> TYPE: PRT
<213> ORGANISM: Artificial Sequence
<220> FEATURE:
<223> OTHER INFORMATION: Human antibody library

<400> SEQUENCE: 104

Asp Ile Gln Met Thr Gln Ser Pro Gly Thr Leu Ser Val Leu Pro Gly
1               5                   10                  15

Glu Arg Ala Thr Leu Ser Cys Arg Ala Ser Glu Arg Ile Ser Ser Asn
            20                  25                  30

Tyr Leu Met Trp Tyr Gln Gln Lys Pro Gly Gln Ala Pro Arg Leu Leu
        35                  40                  45

Met Tyr Gly Ala Ser Ile Arg Ala Thr Gly Ile Pro Asp Arg Phe Ser
    50                  55                  60

Gly Ser Glu Ser Gly Thr Asp Phe Thr Leu Thr Ile Ser Arg Val Glu
65                  70                  75                  80

Pro Glu Asp Phe Ala Val Tyr Tyr Cys Gln Gln Tyr Tyr Ser Ser Pro
                85                  90                  95

Leu Thr Phe Gly Gly Gly Thr Lys Val Glu Met Lys Arg
                100                 105

<210> SEQ ID NO 105
<211> LENGTH: 12
<212> TYPE: PRT
<213> ORGANISM: Artificial Sequence
<220> FEATURE:
<223> OTHER INFORMATION: Human antibody library

<400> SEQUENCE: 105

Arg Ala Ser Gln Ser Ile Ser Ser Asn Tyr Leu Ala
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Human antibody library

<400> SEQUENCE: 106

Gly Ala Ser Ser Arg Ser Thr
1               5

<210> SEQ ID NO 107
<211> LENGTH: 9

```
<212> TYPE: PRT
<213> ORGANISM: Artificial Sequence
<220> FEATURE:
<223> OTHER INFORMATION: Human antibody library

<400> SEQUENCE: 107

Gln Gln Phe Asp Thr Leu Pro Ile Thr
1               5

<210> SEQ ID NO 108
<211> LENGTH: 109
<212> TYPE: PRT
<213> ORGANISM: Artificial Sequence
<220> FEATURE:
<223> OTHER INFORMATION: Human antibody library

<400> SEQUENCE: 108

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ser Thr Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Ile Tyr Tyr Cys Gln Gln Phe Asp Thr Leu Pro
                85                  90                  95

Ile Thr Phe Gly Gln Gly Thr Arg Leu Asp Ile Lys Arg
            100                 105

<210> SEQ ID NO 109
<211> LENGTH: 13
<212> TYPE: PRT
<213> ORGANISM: Artificial Sequence
<220> FEATURE:
<223> OTHER INFORMATION: Human antibody library

<400> SEQUENCE: 109

Arg Ala Ser Gln Ser Ile Arg Ser Ser Gly Tyr Leu Ser
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Human antibody library

<400> SEQUENCE: 110

Gly Ala Ser Thr Arg Ala Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Human antibody library

<400> SEQUENCE: 111

Gln Gln Tyr Gly Ser Ser Thr Ile Thr
1               5
```

<210> SEQ ID NO 112
<211> LENGTH: 110
<212> TYPE: PRT
<213> ORGANISM: Artificial Sequence
<220> FEATURE:
<223> OTHER INFORMATION: Human antibody library

<400> SEQUENCE: 112

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Ile Arg Ser Ser
            20                  25                  30

Gly Tyr Leu Ser Trp Phe Gln Gln Lys Pro Gly Gln Ala Pro Arg Leu
        35                  40                  45

Leu Ile Tyr Gly Ala Ser Thr Arg Ala Thr Gly Thr Pro Ala Arg Phe
    50                  55                  60

Ser Gly Ser Gly Ser Gly Thr Asp Phe Thr Leu Thr Ile Asp Arg Leu
65                  70                  75                  80

Glu Ser Glu Asp Phe Ala Val Tyr Phe Cys Gln Gln Tyr Gly Ser Ser
                85                  90                  95

Thr Ile Thr Phe Gly Gln Gly Thr Arg Leu Glu Ile Lys Arg
            100                 105                 110

<210> SEQ ID NO 113
<211> LENGTH: 12
<212> TYPE: PRT
<213> ORGANISM: Artificial Sequence
<220> FEATURE:
<223> OTHER INFORMATION: Human antibody library

<400> SEQUENCE: 113

Arg Ala Ser Gln Ser Val Ser Ser Asn Tyr Leu Gly
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Human antibody library

<400> SEQUENCE: 114

Gly Ala Ser Ser Arg Ala Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Human antibody library

<400> SEQUENCE: 115

Gln Gln Phe Asp Asn Leu Pro Val Thr
1               5

<210> SEQ ID NO 116
<211> LENGTH: 109
<212> TYPE: PRT
<213> ORGANISM: Artificial Sequence
<220> FEATURE:
<223> OTHER INFORMATION: Human antibody library

<400> SEQUENCE: 116

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Gly Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Gln Gln Phe Asp Asn Leu Pro
                85                  90                  95

Val Thr Phe Gly Gly Gly Thr Lys Val Glu Met Lys Arg
            100                 105

<210> SEQ ID NO 117
<211> LENGTH: 12
<212> TYPE: PRT
<213> ORGANISM: Artificial Sequence
<220> FEATURE:
<223> OTHER INFORMATION: Human antibody library

<400> SEQUENCE: 117

Arg Ala Ser Gln Ser Val Ser Ser Asn Tyr Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Human antibody library

<400> SEQUENCE: 118

Gly Ala Ser Ser Arg Ala Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Human antibody library

<400> SEQUENCE: 119

Gln Gln Phe Asp Thr Ser Pro Leu Thr
1               5

<210> SEQ ID NO 120
<211> LENGTH: 109
<212> TYPE: PRT
<213> ORGANISM: Artificial Sequence
<220> FEATURE:
<223> OTHER INFORMATION: Human antibody library

<400> SEQUENCE: 120

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu

```
            35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Phe Asp Thr Ser Pro
                85                  90                  95
Leu Thr Ile Gly Gly Gly Thr Arg Val Asp Ile Lys Arg
                100                 105

<210> SEQ ID NO 121
<211> LENGTH: 12
<212> TYPE: PRT
<213> ORGANISM: Artificial Sequence
<220> FEATURE:
<223> OTHER INFORMATION: Human antibody library

<400> SEQUENCE: 121

Arg Ala Ser Gln Ser Val Ser Ser Asn Tyr Leu Ala
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Human antibody library

<400> SEQUENCE: 122

Gly Ala Ser Ser Arg Ala Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Human antibody library

<400> SEQUENCE: 123

Gln Gln Phe Asp Ser Ser Pro Leu Ser
1               5

<210> SEQ ID NO 124
<211> LENGTH: 109
<212> TYPE: PRT
<213> ORGANISM: Artificial Sequence
<220> FEATURE:
<223> OTHER INFORMATION: Human antibody library

<400> SEQUENCE: 124

Asp Ile Gln Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Ser Leu Thr Ile Ser Arg Leu Glu
65                  70                  75                  80
Pro Glu Asp Ser Ala Val Tyr Tyr Cys Gln Gln Phe Asp Ser Ser Pro
```

```
                    85                  90                  95

Leu Ser Phe Gly Gly Gly Thr Lys Val Glu Ile Lys Arg
            100                 105

<210> SEQ ID NO 125
<211> LENGTH: 12
<212> TYPE: PRT
<213> ORGANISM: Artificial Sequence
<220> FEATURE:
<223> OTHER INFORMATION: Human antibody library

<400> SEQUENCE: 125

Arg Ala Ser Gln Ser Val Ser Ser Trp Tyr Leu Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Human antibody library

<400> SEQUENCE: 126

Gly Ala Ser Asn Arg Ala Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Human antibody library

<400> SEQUENCE: 127

Gln Gln Phe Asp Ser Ser Pro Leu Thr
1               5

<210> SEQ ID NO 128
<211> LENGTH: 109
<212> TYPE: PRT
<213> ORGANISM: Artificial Sequence
<220> FEATURE:
<223> OTHER INFORMATION: Human antibody library

<400> SEQUENCE: 128

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Trp
            20                  25                  30

Tyr Leu Ala Trp Tyr Gln Gln Lys Pro Gly Gln Ala Pro Arg Leu Leu
        35                  40                  45

Met Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Ile Gly Gly Gly Thr Lys Val Glu Ile Lys Arg
            100                 105

<210> SEQ ID NO 129
<211> LENGTH: 12
<212> TYPE: PRT
```

<213> ORGANISM: Artificial Sequence
<220> FEATURE:
<223> OTHER INFORMATION: Human antibody library

<400> SEQUENCE: 129

Arg Ala Ser Gln Asn Val Gly Ser Ser Tyr Leu Ala
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Human antibody library

<400> SEQUENCE: 130

Gly Ala Ser Ser Arg Ala Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Human antibody library

<400> SEQUENCE: 131

Gln Gln Phe Asp Ser Ser Pro Pro Thr
1               5

<210> SEQ ID NO 132
<211> LENGTH: 109
<212> TYPE: PRT
<213> ORGANISM: Artificial Sequence
<220> FEATURE:
<223> OTHER INFORMATION: Human antibody library

<400> SEQUENCE: 132

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Asn Val Gly Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 133
<211> LENGTH: 12
<212> TYPE: PRT
<213> ORGANISM: Artificial Sequence
<220> FEATURE:
<223> OTHER INFORMATION: Human antibody library

<400> SEQUENCE: 133

Arg Ala Ser Gln Ser Val Ser Ser Ser Tyr Leu Ala
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Human antibody library

<400> SEQUENCE: 134

Gly Ala Ser Ser Arg Ala Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Human antibody library

<400> SEQUENCE: 135

Gln Gln Phe Asp Ser Ser Pro Pro Thr
1               5

<210> SEQ ID NO 136
<211> LENGTH: 109
<212> TYPE: PRT
<213> ORGANISM: Artificial Sequence
<220> FEATURE:
<223> OTHER INFORMATION: Human antibody library

<400> SEQUENCE: 136

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
                100                 105

<210> SEQ ID NO 137
<211> LENGTH: 12
<212> TYPE: PRT
<213> ORGANISM: Artificial Sequence
<220> FEATURE:
<223> OTHER INFORMATION: from human antibody library

<400> SEQUENCE: 137

Arg Ala Ser Gln Ser Val Ser Ser Ser Tyr Leu Ala
1               5                   10

<210> SEQ ID NO 138
<211> LENGTH: 7
<212> TYPE: PRT
<213> ORGANISM: Artificial Sequence
<220> FEATURE:
<223> OTHER INFORMATION: from human antibody library

<400> SEQUENCE: 138

```
Gly Ala Ser Ser Arg Ala Thr
1               5

<210> SEQ ID NO 139
<211> LENGTH: 9
<212> TYPE: PRT
<213> ORGANISM: Artificial Sequence
<220> FEATURE:
<223> OTHER INFORMATION: from human antibody library

<400> SEQUENCE: 139

Gln Gln Phe Asp Ser Ser Pro Pro Thr
1               5

<210> SEQ ID NO 140
<211> LENGTH: 109
<212> TYPE: PRT
<213> ORGANISM: Artificial Sequence
<220> FEATURE:
<223> OTHER INFORMATION: from human antibody library

<400> SEQUENCE: 140

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 141
<211> LENGTH: 12
<212> TYPE: PRT
<213> ORGANISM: Artificial Sequence
<220> FEATURE:
<223> OTHER INFORMATION: Human antibody library

<400> SEQUENCE: 141

Arg Ala Ser Gln Ser Val Ser Ser Ser Tyr Leu Ala
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Human antibody library

<400> SEQUENCE: 142

Gly Ala Ser Ser Arg Ala Thr
1               5

<210> SEQ ID NO 143
<211> LENGTH: 10
<212> TYPE: PRT
<213> ORGANISM: Artificial Sequence
```

<220> FEATURE:
<223> OTHER INFORMATION: Human antibody library

<400> SEQUENCE: 143

Gln Gln Phe Gly Ser Ser Pro Pro Tyr Thr
1               5                   10

<210> SEQ ID NO 144
<211> LENGTH: 110
<212> TYPE: PRT
<213> ORGANISM: Artificial Sequence
<220> FEATURE:
<223> OTHER INFORMATION: Human antibody library

<400> SEQUENCE: 144

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Tyr Thr Leu Thr Ile Asn Arg Leu Glu
65                  70                  75                  80

Pro Glu Asp Phe Ala Val Tyr Tyr Cys Gln Gln Phe Gly Ser Ser Pro
                85                  90                  95

Pro Tyr Thr Phe Gly Gln Gly Thr Lys Leu Glu Ile Lys Arg
            100                 105                 110

<210> SEQ ID NO 145
<211> LENGTH: 12
<212> TYPE: PRT
<213> ORGANISM: Artificial Sequence
<220> FEATURE:
<223> OTHER INFORMATION: Human antibody library

<400> SEQUENCE: 145

Arg Ala Ser Gln Ser Val Ser Ser Ser Tyr Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Human antibody library

<400> SEQUENCE: 146

Gly Ala Ser Thr Arg Ala Thr
1               5

<210> SEQ ID NO 147
<211> LENGTH: 10
<212> TYPE: PRT
<213> ORGANISM: Artificial Sequence
<220> FEATURE:
<223> OTHER INFORMATION: Human antibody library

<400> SEQUENCE: 147

Gln Gln Phe Asp Asn Trp Pro Pro Trp Thr
1               5                   10

```
<210> SEQ ID NO 148
<211> LENGTH: 110
<212> TYPE: PRT
<213> ORGANISM: Artificial Sequence
<220> FEATURE:
<223> OTHER INFORMATION: Human antibody library

<400> SEQUENCE: 148
```

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Pro Arg Phe Ser
    50                  55                  60

Gly Ser Gly Ser Gly Thr Glu Phe Thr Leu Thr Ile Ser Ser Val Gln
65                  70                  75                  80

Ser Glu Asp Phe Ala Ile Tyr Tyr Cys Gln Gln Phe Asp Asn Trp Pro
                85                  90                  95

Pro Trp Thr Phe Gly Gln Gly Thr Lys Val Glu Ile Lys Arg
            100                 105                 110

```
<210> SEQ ID NO 149
<211> LENGTH: 12
<212> TYPE: PRT
<213> ORGANISM: Artificial Sequence
<220> FEATURE:
<223> OTHER INFORMATION: Human antibody library

<400> SEQUENCE: 149
```

Arg Ala Ser Gln Ser Val Ser Ser Asn Tyr Phe Gly
1               5                   10

```
<210> SEQ ID NO 150
<211> LENGTH: 7
<212> TYPE: PRT
<213> ORGANISM: Artificial Sequence
<220> FEATURE:
<223> OTHER INFORMATION: Human antibody library

<400> SEQUENCE: 150
```

Gly Ala Ser Ser Arg Ala Thr
1               5

```
<210> SEQ ID NO 151
<211> LENGTH: 9
<212> TYPE: PRT
<213> ORGANISM: Artificial Sequence
<220> FEATURE:
<223> OTHER INFORMATION: Human antibody library

<400> SEQUENCE: 151
```

Gln Gln Phe Asp Ser Ser Pro Leu Thr
1               5

```
<210> SEQ ID NO 152
<211> LENGTH: 109
<212> TYPE: PRT
<213> ORGANISM: Artificial Sequence
<220> FEATURE:
<223> OTHER INFORMATION: Human antibody library

<400> SEQUENCE: 152
```

```
Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105
```

<210> SEQ ID NO 153
<211> LENGTH: 12
<212> TYPE: PRT
<213> ORGANISM: Artificial Sequence
<220> FEATURE:
<223> OTHER INFORMATION: from human antibody library

<400> SEQUENCE: 153

```
Arg Ala Ser Gln Ser Val Ser Ser Asn Tyr Leu Ala
1               5                   10
```

<210> SEQ ID NO 154
<211> LENGTH: 7
<212> TYPE: PRT
<213> ORGANISM: Artificial Sequence
<220> FEATURE:
<223> OTHER INFORMATION: Human antibody library

<400> SEQUENCE: 154

```
Gly Ala Ser Ser Arg Ala Thr
1               5
```

<210> SEQ ID NO 155
<211> LENGTH: 9
<212> TYPE: PRT
<213> ORGANISM: Artificial Sequence
<220> FEATURE:
<223> OTHER INFORMATION: Human antibody library

<400> SEQUENCE: 155

```
Gln Gln Phe Asp Ser Ser Pro Leu Ser
1               5
```

<210> SEQ ID NO 156
<211> LENGTH: 109
<212> TYPE: PRT
<213> ORGANISM: Artificial Sequence
<220> FEATURE:
<223> OTHER INFORMATION: Human antibody library

<400> SEQUENCE: 156

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Ser Leu Thr Ile Ser Arg Leu Glu
 65                  70                  75                  80

Pro Glu Asp Ser Ala Val Tyr Tyr Cys Gln Gln Phe Asp Ser Ser Pro
                 85                  90                  95

Leu Ser Phe Gly Gly Gly Thr Lys Val Glu Ile Lys Arg
            100                 105
```

<210> SEQ ID NO 157
<211> LENGTH: 12
<212> TYPE: PRT
<213> ORGANISM: Artificial Sequence
<220> FEATURE:
<223> OTHER INFORMATION: Human antibody library

<400> SEQUENCE: 157

```
Arg Ala Ser Gln Ser Val Ser Ser Asn Tyr Leu Ala
 1               5                  10
```

<210> SEQ ID NO 158
<211> LENGTH: 7
<212> TYPE: PRT
<213> ORGANISM: Artificial Sequence
<220> FEATURE:
<223> OTHER INFORMATION: Human antibody library

<400> SEQUENCE: 158

```
Gly Ala Ser Thr Arg Ala Thr
 1               5
```

<210> SEQ ID NO 159
<211> LENGTH: 9
<212> TYPE: PRT
<213> ORGANISM: Artificial Sequence
<220> FEATURE:
<223> OTHER INFORMATION: Human antibody library

<400> SEQUENCE: 159

```
Gln Gln Phe Asp Ser Ser Pro Leu Ser
 1               5
```

<210> SEQ ID NO 160
<211> LENGTH: 109
<212> TYPE: PRT
<213> ORGANISM: Artificial Sequence
<220> FEATURE:
<223> OTHER INFORMATION: Human antibody library

<400> SEQUENCE: 160

```
Asp Ile Gln Met Thr Gln Ser Pro Gly Thr Leu Ser Leu Ser Pro Gly
 1               5                  10                  15

Asp Arg Ala Thr Leu Ser Cys Arg Ala Ser Gln Ser Val Ser Ser Asn
                 20                  25                  30

Tyr Leu Ala Trp Tyr Gln Gln Lys Pro Gly Gln Ala Pro Arg Val Leu
             35                  40                  45

Ile Tyr Gly Ala Ser Thr Arg Ala Thr Gly Ile Pro Asp Arg Phe Thr
 50                  55                  60

Gly Ser Gly Ser Gly Thr Asp Phe Thr Leu Thr Ile Ser Arg Leu Glu
 65                  70                  75                  80

Pro Glu Asp Ser Ala Val Tyr Tyr Cys Gln Gln Phe Asp Ser Ser Pro
                 85                  90                  95
```

Leu Ser Phe Gly Gly Gly Thr Lys Val Glu Ile Lys Arg
            100                 105

<210> SEQ ID NO 161
<211> LENGTH: 12
<212> TYPE: PRT
<213> ORGANISM: Artificial Sequence
<220> FEATURE:
<223> OTHER INFORMATION: Human antibody library

<400> SEQUENCE: 161

Arg Ala Ser Gln Ser Leu Asn Asn Asn Tyr Leu Ala
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Human antibody library

<400> SEQUENCE: 162

Gly Ala Ser Thr Arg Ala Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Human antibody library

<400> SEQUENCE: 163

Gln Gln Phe Asp Ser Ser Pro Pro Thr
1               5

<210> SEQ ID NO 164
<211> LENGTH: 109
<212> TYPE: PRT
<213> ORGANISM: Artificial Sequence
<220> FEATURE:
<223> OTHER INFORMATION: Human antibody library

<400> SEQUENCE: 164

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Asn Asn
            20                  25                  30

Tyr Leu Ala Trp Tyr Gln Gln Lys Pro Gly Gln Ala Pro Arg Leu Leu
        35                  40                  45

Met Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 165
<211> LENGTH: 12
<212> TYPE: PRT
<213> ORGANISM: Artificial Sequence
<220> FEATURE:

<223> OTHER INFORMATION: Human antibody library

<400> SEQUENCE: 165

Arg Ala Ser His Ser Val Ser Ser Asp Tyr Leu Ala
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Human antibody library

<400> SEQUENCE: 166

Gly Ala Ser Ser Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Human antibody library

<400> SEQUENCE: 167

Gln Gln Phe Asp Ser Ser Pro Pro Thr
1               5

<210> SEQ ID NO 168
<211> LENGTH: 109
<212> TYPE: PRT
<213> ORGANISM: Artificial Sequence
<220> FEATURE:
<223> OTHER INFORMATION: Human antibody library

<400> SEQUENCE: 168

Asp Ile Gln Met Thr Gln Ser Pro Ala Thr Leu Ser Leu Ser Pro Gly
1               5                   10                  15

Glu Arg Ala Thr Leu Ser Cys Arg Ala Ser His Ser Val Ser Ser Asp
                20                  25                  30

Tyr Leu Ala Trp Tyr Gln Gln Lys Pro Gly Arg Ala Pro Arg Leu Leu
            35                  40                  45

Met Tyr Gly Ala Ser Ser Arg Ala Thr Gly Phe Pro Asp Arg Phe Ser
        50                  55                  60

Gly Ser Gly Ser Gly Thr Asp Phe Ser Leu Thr Ile Ser Arg Leu Glu
65                  70                  75                  80

Pro Glu Asp Phe Ala Met Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 169
<211> LENGTH: 12
<212> TYPE: PRT
<213> ORGANISM: Artificial Sequence
<220> FEATURE:
<223> OTHER INFORMATION: from human antibody library

<400> SEQUENCE: 169

Arg Ala Ser His Ser Val Ser Ser Asp Tyr Leu Ala
1               5                   10

<210> SEQ ID NO 170

```
<211> LENGTH: 7
<212> TYPE: PRT
<213> ORGANISM: Artificial Sequence
<220> FEATURE:
<223> OTHER INFORMATION: from human antibody library

<400> SEQUENCE: 170

Gly Ala Ser Ser Arg Ala Thr
1               5

<210> SEQ ID NO 171
<211> LENGTH: 9
<212> TYPE: PRT
<213> ORGANISM: Artificial Sequence
<220> FEATURE:
<223> OTHER INFORMATION: from human antibody library

<400> SEQUENCE: 171

Gln Gln Phe Asp Ser Ser Pro Pro Thr
1               5

<210> SEQ ID NO 172
<211> LENGTH: 109
<212> TYPE: PRT
<213> ORGANISM: Artificial Sequence
<220> FEATURE:
<223> OTHER INFORMATION: from human antibody library

<400> SEQUENCE: 172

Asp Ile Gln Met Thr Gln Ser Pro Ala Thr Leu Ser Val Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Met Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 173
<211> LENGTH: 12
<212> TYPE: PRT
<213> ORGANISM: Artificial Sequence
<220> FEATURE:
<223> OTHER INFORMATION: Human antibody library

<400> SEQUENCE: 173

Arg Ala Ser His Ser Val Ser Ser Asp Tyr Leu Ala
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Human antibody library

<400> SEQUENCE: 174

Gly Ala Ser Ser Arg Ala Thr
```

```
<210> SEQ ID NO 175
<211> LENGTH: 9
<212> TYPE: PRT
<213> ORGANISM: Artificial Sequence
<220> FEATURE:
<223> OTHER INFORMATION: Human antibody library

<400> SEQUENCE: 175

Gln Gln Phe Asp Ser Ser Pro Pro Thr
1               5

<210> SEQ ID NO 176
<211> LENGTH: 109
<212> TYPE: PRT
<213> ORGANISM: Artificial Sequence
<220> FEATURE:
<223> OTHER INFORMATION: Human antibody library

<400> SEQUENCE: 176

Asp Ile Gln Met Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 177
<211> LENGTH: 12
<212> TYPE: PRT
<213> ORGANISM: Artificial Sequence
<220> FEATURE:
<223> OTHER INFORMATION: Human antibody library

<400> SEQUENCE: 177

Arg Ala Ser His Ser Val Ser Ser Asp Tyr Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Human antibody library

<400> SEQUENCE: 178

Gly Ala Ser Ser Arg Ala Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Human antibody library
```

<400> SEQUENCE: 179

Gln Gln Phe Asp Ser Ser Pro Pro Thr
1               5

<210> SEQ ID NO 180
<211> LENGTH: 111
<212> TYPE: PRT
<213> ORGANISM: Artificial Sequence
<220> FEATURE:
<223> OTHER INFORMATION: from human Fab library

<400> SEQUENCE: 180

Ile Ala Asp Ile Gln Met Thr Gln Ser Pro Asp Thr Leu Ser Leu Ser
1               5                   10                  15

Pro Gly Glu Arg Ala Thr Leu Ser Cys Arg Ala Ser His Ser Val Ser
            20                  25                  30

Ser Asp Tyr Leu Ala Trp Tyr Gln Gln Lys Pro Gly Arg Ala Pro Arg
        35                  40                  45

Leu Leu Met Tyr Gly Ala Ser Ser Arg Ala Thr Gly Phe Pro Asp Arg
    50                  55                  60

Phe Ser Gly Ser Gly Ser Gly Thr Asp Phe Ser Leu Thr Ile Ser Arg
65                  70                  75                  80

Leu Glu Pro Glu Asp Phe Ala Val Tyr Tyr Cys Gln Gln Phe Asp Ser
                85                  90                  95

Ser Pro Pro Thr Phe Gly Gly Gly Thr Lys Val Glu Ile Lys Arg
            100                 105                 110

<210> SEQ ID NO 181
<211> LENGTH: 12
<212> TYPE: PRT
<213> ORGANISM: Artificial Sequence
<220> FEATURE:
<223> OTHER INFORMATION: from human antibody library

<400> SEQUENCE: 181

Arg Ala Ser His Ser Val Ser Ser Asp Tyr Leu Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: from human antibody library

<400> SEQUENCE: 182

Gly Ala Ser Ser Arg Ala Thr
1               5

<210> SEQ ID NO 183
<211> LENGTH: 9
<212> TYPE: PRT
<213> ORGANISM: Artificial Sequence
<220> FEATURE:
<223> OTHER INFORMATION: from human antibody library

<400> SEQUENCE: 183

Gln Gln Phe Asp Ser Ser Pro Pro Thr
1               5

<210> SEQ ID NO 184
<211> LENGTH: 109

```
<212> TYPE: PRT
<213> ORGANISM: Artificial Sequence
<220> FEATURE:
<223> OTHER INFORMATION: from human antibody library

<400> SEQUENCE: 184

Asp Ile Gln Met Thr Gln Ser Pro Asp Thr Leu Ser Leu Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Arg Ile Asp Ile Lys Arg
            100                 105

<210> SEQ ID NO 185
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (8)..(8)
<223> OTHER INFORMATION: residue is V or I
<220> FEATURE:
<221> NAME/KEY: VARIANT
<222> LOCATION: (10)..(10)
<223> OTHER INFORMATION: residue is G or L

<400> SEQUENCE: 185

Gly Phe Thr Phe Ser Trp Tyr Xaa Met Xaa
1               5                   10

<210> SEQ ID NO 186
<211> LENGTH: 17
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (3)..(3)
<223> OTHER INFORMATION: residue is Y or G
<220> FEATURE:
<221> NAME/KEY: VARIANT
<222> LOCATION: (4)..(4)
<223> OTHER INFORMATION: residue is P or S
<220> FEATURE:
<221> NAME/KEY: VARIANT
<222> LOCATION: (8)..(8)
<223> OTHER INFORMATION: residue is A or F
<220> FEATURE:
<221> NAME/KEY: VARIANT
<222> LOCATION: (10)..(10)
<223> OTHER INFORMATION: residue is N or D

<400> SEQUENCE: 186

Ser Ile Xaa Xaa Ser Gly Gly Xaa Thr Xaa Tyr Ala Asp Ser Val Lys
1               5                   10                  15

Gly
```

```
<210> SEQ ID NO 187
<211> LENGTH: 11
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is S Q or T
<220> FEATURE:
<221> NAME/KEY: VARIANT
<222> LOCATION: (3)..(3)
<223> OTHER INFORMATION: residue is D E or Q
<220> FEATURE:
<221> NAME/KEY: VARIANT
<222> LOCATION: (4)..(4)
<223> OTHER INFORMATION: residue is K S N I or A
<220> FEATURE:
<221> NAME/KEY: VARIANT
<222> LOCATION: (6)..(6)
<223> OTHER INFORMATION: residue is G or R
<220> FEATURE:
<221> NAME/KEY: VARIANT
<222> LOCATION: (7)..(7)
<223> OTHER INFORMATION: residue is D S H E or N
<220> FEATURE:
<221> NAME/KEY: VARIANT
<222> LOCATION: (8)..(8)
<223> OTHER INFORMATION: residue is E Y Q R or N
<220> FEATURE:
<221> NAME/KEY: VARIANT
<222> LOCATION: (9)..(9)
<223> OTHER INFORMATION: residue is Y F or S
<220> FEATURE:
<221> NAME/KEY: VARIANT
<222> LOCATION: (10)..(10)
<223> OTHER INFORMATION: residue is A or S

<400> SEQUENCE: 187

Xaa Gly Xaa Xaa Leu Xaa Xaa Xaa Xaa Xaa Ser
1               5                   10

<210> SEQ ID NO 188
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
<223> OTHER INFORMATION: residue is S or T
<220> FEATURE:
<221> NAME/KEY: VARIANT
<222> LOCATION: (7)..(7)
<223> OTHER INFORMATION: residue is I or L
<220> FEATURE:
<221> NAME/KEY: VARIANT
<222> LOCATION: (8)..(8)
<223> OTHER INFORMATION: residue is E or G
<220> FEATURE:
<221> NAME/KEY: VARIANT
<222> LOCATION: (9)..(9)
<223> OTHER INFORMATION: residue is T S or N
<220> FEATURE:
<221> NAME/KEY: VARIANT
<222> LOCATION: (10)..(10)
<223> OTHER INFORMATION: residue is N or Y
<220> FEATURE:
<221> NAME/KEY: VARIANT
<222> LOCATION: (11)..(11)
<223> OTHER INFORMATION: residue is T P A or Y
<220> FEATURE:
<221> NAME/KEY: VARIANT
```

```
<222> LOCATION: (12)..(12)
<223> OTHER INFORMATION: residue is V or L
<220> FEATURE:
<221> NAME/KEY: VARIANT
<222> LOCATION: (13)..(13)
<223> OTHER INFORMATION: residue is N I or Y

<400> SEQUENCE: 188

Ser Gly Ser Xaa Ser Asn Xaa Xaa Xaa Xaa Xaa Xaa
1               5                   10

<210> SEQ ID NO 189
<211> LENGTH: 14
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is A or T
<220> FEATURE:
<221> NAME/KEY: VARIANT
<222> LOCATION: (3)..(3)
<223> OTHER INFORMATION: residue is S or T
<220> FEATURE:
<221> NAME/KEY: VARIANT
<222> LOCATION: (5)..(5)
<223> OTHER INFORMATION: residue is H S or N
<220> FEATURE:
<221> NAME/KEY: VARIANT
<222> LOCATION: (7)..(7)
<223> OTHER INFORMATION: residue is I or V
<220> FEATURE:
<221> NAME/KEY: VARIANT
<222> LOCATION: (9)..(9)
<223> OTHER INFORMATION: residue is S or A

<400> SEQUENCE: 189

Xaa Gly Xaa Ser Xaa Asp Xaa Gly Xaa Tyr Asp Tyr Val Ser
1               5                   10

<210> SEQ ID NO 190
<211> LENGTH: 7
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is Q D T Y S or A
<220> FEATURE:
<221> NAME/KEY: VARIANT
<222> LOCATION: (2)..(2)
<223> OTHER INFORMATION: residue is D N S T or V
<220> FEATURE:
<221> NAME/KEY: VARIANT
<222> LOCATION: (3)..(3)
<223> OTHER INFORMATION: residue is D N S T or Y
<220> FEATURE:
<221> NAME/KEY: VARIANT
<222> LOCATION: (4)..(4)
<223> OTHER INFORMATION: residue is Q K N or L
<220> FEATURE:
<221> NAME/KEY: VARIANT
<222> LOCATION: (5)..(5)
<223> OTHER INFORMATION: residue is R or L

<400> SEQUENCE: 190

Xaa Xaa Xaa Xaa Xaa Pro Ser
1               5
```

```
<210> SEQ ID NO 191
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A or T
<220> FEATURE:
<221> NAME/KEY: VARIANT
<222> LOCATION: (4)..(4)
<223> OTHER INFORMATION: residue is D or G
<220> FEATURE:
<221> NAME/KEY: VARIANT
<222> LOCATION: (5)..(5)
<223> OTHER INFORMATION: residue is R or no amino acid
<220> FEATURE:
<221> NAME/KEY: VARIANT
<222> LOCATION: (6)..(6)
<223> OTHER INFORMATION: residue is S F or N
<220> FEATURE:
<221> NAME/KEY: VARIANT
<222> LOCATION: (7)..(7)
<223> OTHER INFORMATION: residue is S T or N
<220> FEATURE:
<221> NAME/KEY: VARIANT
<222> LOCATION: (8)..(8)
<223> OTHER INFORMATION: residue is S T or P
<220> FEATURE:
<221> NAME/KEY: VARIANT
<222> LOCATION: (9)..(9)
<223> OTHER INFORMATION: residue is A V L I or Y
<220> FEATURE:
<221> NAME/KEY: VARIANT
<222> LOCATION: (10)..(10)
<223> OTHER INFORMATION: residue is V or L

<400> SEQUENCE: 191

Gln Xaa Trp Xaa Xaa Xaa Xaa Xaa Xaa Xaa
1               5                   10

<210> SEQ ID NO 192
<211> LENGTH: 11
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A S or T
<220> FEATURE:
<221> NAME/KEY: VARIANT
<222> LOCATION: (6)..(6)
<223> OTHER INFORMATION: residue is N or S
<220> FEATURE:
<221> NAME/KEY: VARIANT
<222> LOCATION: (8)..(8)
<223> OTHER INFORMATION: residue is N I or G
<220> FEATURE:
<221> NAME/KEY: VARIANT
<222> LOCATION: (9)..(9)
<223> OTHER INFORMATION: residue is G or S
<220> FEATURE:
<221> NAME/KEY: VARIANT
<222> LOCATION: (10)..(10)
<223> OTHER INFORMATION: residue is P W or V
<220> FEATURE:
<221> NAME/KEY: VARIANT
<222> LOCATION: (11)..(11)
<223> OTHER INFORMATION: residue is V or L

<400> SEQUENCE: 192

Ala Xaa Trp Asp Asp Xaa Leu Xaa Xaa Xaa Xaa
```

<210> SEQ ID NO 193
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (7)..(7)
<223> OTHER INFORMATION: residue is A or T

<400> SEQUENCE: 193

Met Tyr Ser Thr Ile Thr Xaa Leu Leu
1               5

<210> SEQ ID NO 194
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
<223> OTHER INFORMATION: residue is Q E or H
<220> FEATURE:
<221> NAME/KEY: VARIANT
<222> LOCATION: (5)..(5)
<223> OTHER INFORMATION: residue is S R or N
<220> FEATURE:
<221> NAME/KEY: VARIANT
<222> LOCATION: (6)..(6)
<223> OTHER INFORMATION: residue is V I or L
<220> FEATURE:
<221> NAME/KEY: VARIANT
<222> LOCATION: (7)..(7)
<223> OTHER INFORMATION: residue is S R G or N
<220> FEATURE:
<221> NAME/KEY: VARIANT
<222> LOCATION: (8)..(8)
<223> OTHER INFORMATION: residue is S or N
<220> FEATURE:
<221> NAME/KEY: VARIANT
<222> LOCATION: (9)..(9)
<223> OTHER INFORMATION: residue is S N W or D
<220> FEATURE:
<221> NAME/KEY: VARIANT
<222> LOCATION: (10)..(10)
<223> OTHER INFORMATION: residue is G or no amino acid
<220> FEATURE:
<221> NAME/KEY: VARIANT
<222> LOCATION: (12)..(12)
<223> OTHER INFORMATION: residue is L or F
<220> FEATURE:
<221> NAME/KEY: VARIANT
<222> LOCATION: (13)..(13)
<223> OTHER INFORMATION: residue is A G M or S

<400> SEQUENCE: 194

Arg Ala Ser Xaa Xaa Xaa Xaa Xaa Xaa Xaa Tyr Xaa Xaa
1               5                   10

<210> SEQ ID NO 195
<211> LENGTH: 7
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
<223> OTHER INFORMATION: residue is S T I or N

<400> SEQUENCE: 195

Gly Ala Ser Xaa Arg Ala Thr
1               5

<210> SEQ ID NO 196
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (3)..(3)
<223> OTHER INFORMATION: residue is F or Y
<220> FEATURE:
<221> NAME/KEY: VARIANT
<222> LOCATION: (4)..(4)
<223> OTHER INFORMATION: residue is D G or Y
<220> FEATURE:
<221> NAME/KEY: VARIANT
<222> LOCATION: (5)..(5)
<223> OTHER INFORMATION: residue is S T or N
<220> FEATURE:
<221> NAME/KEY: VARIANT
<222> LOCATION: (6)..(6)
<223> OTHER INFORMATION: residue is S L or W
<220> FEATURE:
<221> NAME/KEY: VARIANT
<222> LOCATION: (7)..(7)
<223> OTHER INFORMATION: residue is P or no amino acid
<220> FEATURE:
<221> NAME/KEY: VARIANT
<222> LOCATION: (8)..(8)
<223> OTHER INFORMATION: residue is P or T
<220> FEATURE:
<221> NAME/KEY: VARIANT
<222> LOCATION: (9)..(9)
<223> OTHER INFORMATION: residue is L I V P W or Y
<220> FEATURE:
<221> NAME/KEY: VARIANT
<222> LOCATION: (10)..(10)
<223> OTHER INFORMATION: residue is T or S

<400> SEQUENCE: 196

Gln Gln Xaa Xaa Xaa Xaa Xaa Xaa Xaa Xaa
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Mutation of library member

<400> SEQUENCE: 197

Gly Phe Thr Phe Ser Trp Tyr
1               5

<210> SEQ ID NO 198
<211> LENGTH: 6
<212> TYPE: PRT
<213> ORGANISM: Artificial Sequence
<220> FEATURE:
<223> OTHER INFORMATION: Mutation of library member

<400> SEQUENCE: 198

Tyr Pro Gln Gly Gly Ala
1               5

<210> SEQ ID NO 199

```
<211> LENGTH: 6
<212> TYPE: PRT
<213> ORGANISM: Artificial Sequence
<220> FEATURE:
<223> OTHER INFORMATION: Mutation of library member

<400> SEQUENCE: 199

Gly Asn Tyr Phe Asp Tyr
1               5

<210> SEQ ID NO 200
<211> LENGTH: 115
<212> TYPE: PRT
<213> ORGANISM: Artificial Sequence
<220> FEATURE:
<223> OTHER INFORMATION: Mutation of library member

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Gln Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Ser
        115

<210> SEQ ID NO 201
<211> LENGTH: 12
<212> TYPE: PRT
<213> ORGANISM: Artificial Sequence
<220> FEATURE:
<223> OTHER INFORMATION: Mutation of library member

<400> SEQUENCE: 201

Arg Ala Ser Gln Ser Val Ser Ser Asn Tyr Phe Gly
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Mutation of library member

<400> SEQUENCE: 202

Gly Ala Ser Ser Arg Ala Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Mutation of library member
```

```
<400> SEQUENCE: 203

Gln Gln Phe Asp Ser Leu Pro Leu Thr
1               5

<210> SEQ ID NO 204
<211> LENGTH: 109
<212> TYPE: PRT
<213> ORGANISM: Artificial Sequence
<220> FEATURE:
<223> OTHER INFORMATION: Mutation of library member

<400> SEQUENCE: 204

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Leu Pro
                85                  90                  95

Leu Thr Phe Gly Gly Gly Thr Lys Val Glu Ile Lys Arg
            100                 105

<210> SEQ ID NO 205
<211> LENGTH: 7
<212> TYPE: PRT
<213> ORGANISM: Artificial Sequence
<220> FEATURE:
<223> OTHER INFORMATION: Mutation of library member

<400> SEQUENCE: 205

Gly Phe Thr Phe Ser Trp Tyr
1               5

<210> SEQ ID NO 206
<211> LENGTH: 6
<212> TYPE: PRT
<213> ORGANISM: Artificial Sequence
<220> FEATURE:
<223> OTHER INFORMATION: Mutation of library member

<400> SEQUENCE: 206

Tyr Pro Gln Gly Gly Ala
1               5

<210> SEQ ID NO 207
<211> LENGTH: 6
<212> TYPE: PRT
<213> ORGANISM: Artificial Sequence
<220> FEATURE:
<223> OTHER INFORMATION: Mutation of library member

<400> SEQUENCE: 207

Gly Asn Tyr Phe Asp Tyr
1               5

<210> SEQ ID NO 208
<211> LENGTH: 115
<212> TYPE: PRT
```

<213> ORGANISM: Artificial Sequence
<220> FEATURE:
<223> OTHER INFORMATION: Mutation of library member

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Ser Trp Val Arg Gln Ala Pro Gly Lys Gly Leu Glu Trp Val
        35                  40                  45

Ser Ser Ile Tyr Pro Gln Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Ser
        115

<210> SEQ ID NO 209
<211> LENGTH: 12
<212> TYPE: PRT
<213> ORGANISM: Artificial Sequence
<220> FEATURE:
<223> OTHER INFORMATION: Mutation of library member

<400> SEQUENCE: 209

Arg Ala Ser Gln Ser Val Ser Ser Asn Tyr Phe Gly
1               5                   10

<210> SEQ ID NO 210
<211> LENGTH: 7
<212> TYPE: PRT
<213> ORGANISM: Artificial Sequence
<220> FEATURE:
<223> OTHER INFORMATION: Mutation of library member

<400> SEQUENCE: 210

Gly Ala Ser Ser Arg Ala Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Mutation of library member

<400> SEQUENCE: 211

Gln Gln His Asp Ser Ser Pro Leu Ser
1               5

<210> SEQ ID NO 212
<211> LENGTH: 109
<212> TYPE: PRT
<213> ORGANISM: Artificial Sequence
<220> FEATURE:
<223> OTHER INFORMATION: Mutated library sequence

<400> SEQUENCE: 212

```
Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln His Asp Ser Ser Pro
                85                  90                  95

Leu Ser Phe Gly Gly Gly Thr Lys Val Glu Ile Lys Arg
            100                 105
```

<210> SEQ ID NO 213
<211> LENGTH: 7
<212> TYPE: PRT
<213> ORGANISM: Artificial Sequence
<220> FEATURE:
<223> OTHER INFORMATION: Mutated library sequence

<400> SEQUENCE: 213

```
Gly Phe Thr Phe Ser Trp Tyr
1               5
```

<210> SEQ ID NO 214
<211> LENGTH: 6
<212> TYPE: PRT
<213> ORGANISM: Artificial Sequence
<220> FEATURE:
<223> OTHER INFORMATION: Mutated library sequence

<400> SEQUENCE: 214

```
Tyr Pro Ser Gly Gly Ala
1               5
```

<210> SEQ ID NO 215
<211> LENGTH: 6
<212> TYPE: PRT
<213> ORGANISM: Artificial Sequence
<220> FEATURE:
<223> OTHER INFORMATION: Mutated library sequence

<400> SEQUENCE: 215

```
Gly Asn Tyr Leu Asp Tyr
1               5
```

<210> SEQ ID NO 216
<211> LENGTH: 115
<212> TYPE: PRT
<213> ORGANISM: Artificial Sequence
<220> FEATURE:
<223> OTHER INFORMATION: Mutated library sequence

<400> SEQUENCE: 216

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45
```

```
Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asn Tyr Leu Asp Tyr Trp Gly Gln Gly Thr Leu Val Thr
            100                 105                 110

Val Ser Ser
        115
```

<210> SEQ ID NO 217
<211> LENGTH: 12
<212> TYPE: PRT
<213> ORGANISM: Artificial Sequence
<220> FEATURE:
<223> OTHER INFORMATION: Mutated library sequence

<400> SEQUENCE: 217

```
Arg Ala Ser Gln Ser Val Ser Ser Asn Tyr Phe Gly
 1               5                  10
```

<210> SEQ ID NO 218
<211> LENGTH: 7
<212> TYPE: PRT
<213> ORGANISM: Artificial Sequence
<220> FEATURE:
<223> OTHER INFORMATION: Mutated library sequence

<400> SEQUENCE: 218

```
Gly Ala Ser Ser Arg Ala Thr
 1               5
```

<210> SEQ ID NO 219
<211> LENGTH: 9
<212> TYPE: PRT
<213> ORGANISM: Artificial Sequence
<220> FEATURE:
<223> OTHER INFORMATION: Mutated library sequence

<400> SEQUENCE: 219

```
Gln Gln Phe Asp Ser Ser Pro Leu Ser
 1               5
```

<210> SEQ ID NO 220
<211> LENGTH: 109
<212> TYPE: PRT
<213> ORGANISM: Artificial Sequence
<220> FEATURE:
<223> OTHER INFORMATION: Mutated library sequence

<400> SEQUENCE: 220

```
Asp Ile Gln Met Thr Gln Ser Pro Gly Thr Leu Ser Leu Ser Pro Gly
 1               5                  10                  15

Glu Gly Ala Thr Leu Ser Cys Arg Ala Ser Gln Ser Val Ser Ser Asn
                 20                  25                  30

Tyr Phe Gly Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80
```

```
Pro Glu Asp Ser Ala Val Tyr Tyr Cys Gln Gln Phe Asp Ser Ser Pro
                85                  90                  95

Leu Ser Phe Gly Gly Gly Thr Lys Val Glu Ile Lys Arg
            100                 105
```

<210> SEQ ID NO 221
<211> LENGTH: 7
<212> TYPE: PRT
<213> ORGANISM: Artificial Sequence
<220> FEATURE:
<223> OTHER INFORMATION: Mutated library sequence

<400> SEQUENCE: 221

```
Gly Phe Thr Phe Ser Trp Tyr
1               5
```

<210> SEQ ID NO 222
<211> LENGTH: 6
<212> TYPE: PRT
<213> ORGANISM: Artificial Sequence
<220> FEATURE:
<223> OTHER INFORMATION: Mutated library sequence

<400> SEQUENCE: 222

```
Tyr Pro Ser Gly Gly Ala
1               5
```

<210> SEQ ID NO 223
<211> LENGTH: 6
<212> TYPE: PRT
<213> ORGANISM: Artificial Sequence
<220> FEATURE:
<223> OTHER INFORMATION: Mutated library sequence

<400> SEQUENCE: 223

```
Gly Pro Tyr Leu Asp Tyr
1               5
```

<210> SEQ ID NO 224
<211> LENGTH: 115
<212> TYPE: PRT
<213> ORGANISM: Artificial Sequence
<220> FEATURE:
<223> OTHER INFORMATION: Mutated library sequence

<400> SEQUENCE: 224

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
                20                  25                  30

Val Met Gly Trp Val Arg Gln Ala Pro Gly Lys Gly Leu Glu Trp Val
            35                  40                  45

Ser Ser Ile Tyr Pro Ser Gly Gly Ala Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Leu Asp Tyr Trp Gly Gln Gly Thr Leu Val Thr
            100                 105                 110

Val Ser Ser
        115
```

<210> SEQ ID NO 225
<211> LENGTH: 12
<212> TYPE: PRT
<213> ORGANISM: Artificial Sequence
<220> FEATURE:
<223> OTHER INFORMATION: Mutated library sequence

<400> SEQUENCE: 225

Arg Ala Ser Gln Ser Val Ser Ser Asn Tyr Phe Gly
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Mutated library sequence

<400> SEQUENCE: 226

Gly Ala Ser Ser Arg Ala Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Mutated library sequence

<400> SEQUENCE: 227

Gln Gln Phe Asp Ser Ser Pro Leu Thr
1               5

<210> SEQ ID NO 228
<211> LENGTH: 109
<212> TYPE: PRT
<213> ORGANISM: Artificial Sequence
<220> FEATURE:
<223> OTHER INFORMATION: Mutated library sequence

<400> SEQUENCE: 228

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105

<210> SEQ ID NO 229
<211> LENGTH: 7
<212> TYPE: PRT
<213> ORGANISM: Artificial Sequence
<220> FEATURE:
<223> OTHER INFORMATION: Mutated library sequence

<400> SEQUENCE: 229

Gly Phe Thr Phe Ser Trp Tyr
1               5

<210> SEQ ID NO 230
<211> LENGTH: 6
<212> TYPE: PRT
<213> ORGANISM: Artificial Sequence
<220> FEATURE:
<223> OTHER INFORMATION: Mutated library sequence

<400> SEQUENCE: 230

Tyr Pro Ser Gly Gly Ala
1               5

<210> SEQ ID NO 231
<211> LENGTH: 6
<212> TYPE: PRT
<213> ORGANISM: Artificial Sequence
<220> FEATURE:
<223> OTHER INFORMATION: Mutated library sequence

<400> SEQUENCE: 231

Gly Ser Tyr Leu Asp Tyr
1               5

<210> SEQ ID NO 232
<211> LENGTH: 115
<212> TYPE: PRT
<213> ORGANISM: Artificial Sequence
<220> FEATURE:
<223> OTHER INFORMATION: Mutated library sequence

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Leu Asp Tyr Trp Gly Gln Gly Thr Leu Val Thr
            100                 105                 110

Val Ser Ser
        115

<210> SEQ ID NO 233
<211> LENGTH: 12
<212> TYPE: PRT
<213> ORGANISM: Artificial Sequence
<220> FEATURE:
<223> OTHER INFORMATION: Mutated library sequence

<400> SEQUENCE: 233

Arg Ala Ser Gln Ser Val Ser Ser Asn Tyr Phe Gly
1               5                   10

<210> SEQ ID NO 234

```
<211> LENGTH: 7
<212> TYPE: PRT
<213> ORGANISM: Artificial Sequence
<220> FEATURE:
<223> OTHER INFORMATION: Mutated library sequence

<400> SEQUENCE: 234

Gly Ala Ser Ser Arg Ala Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Mutated library sequence

<400> SEQUENCE: 235

Gln Gln Phe Asp Ser Ser Pro Leu Thr
1               5

<210> SEQ ID NO 236
<211> LENGTH: 109
<212> TYPE: PRT
<213> ORGANISM: Artificial Sequence
<220> FEATURE:
<223> OTHER INFORMATION: Mutated library sequence

<400> SEQUENCE: 236

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105

<210> SEQ ID NO 237
<211> LENGTH: 10
<212> TYPE: PRT
<213> ORGANISM: Artificial Sequence
<220> FEATURE:
<223> OTHER INFORMATION: Mutated library sequence

<400> SEQUENCE: 237

Gly Phe Thr Phe Ser Trp Tyr Val Met Gly
1               5                   10

<210> SEQ ID NO 238
<211> LENGTH: 17
<212> TYPE: PRT
<213> ORGANISM: Artificial Sequence
<220> FEATURE:
<223> OTHER INFORMATION: Mutated library sequence

<400> SEQUENCE: 238

Ser Ile Tyr Pro Gln Gly Gly Ala Thr Ser Tyr Ala Asp Ser Val Lys
```

<210> SEQ ID NO 239
<211> LENGTH: 17
<212> TYPE: PRT
<213> ORGANISM: Artificial Sequence
<220> FEATURE:
<223> OTHER INFORMATION: Mutated library sequence

<400> SEQUENCE: 239

Ser Ile Tyr Pro Gln Gly Gly Ala Thr Asn Tyr Ala Asp Ser Val Lys
1               5                   10                  15
Gly

<210> SEQ ID NO 240
<211> LENGTH: 17
<212> TYPE: PRT
<213> ORGANISM: Artificial Sequence
<220> FEATURE:
<223> OTHER INFORMATION: Mutated library sequence

<400> SEQUENCE: 240

Ser Ile Tyr Pro Ser Gly Gly Ala Thr Asn Tyr Ala Asp Ser Val Lys
1               5                   10                  15
Gly

<210> SEQ ID NO 241
<211> LENGTH: 6
<212> TYPE: PRT
<213> ORGANISM: Artificial Sequence
<220> FEATURE:
<223> OTHER INFORMATION: Mutated library sequence

<400> SEQUENCE: 241

Gly Asn Tyr Phe Asp Tyr
1               5

<210> SEQ ID NO 242
<211> LENGTH: 6
<212> TYPE: PRT
<213> ORGANISM: Artificial Sequence
<220> FEATURE:
<223> OTHER INFORMATION: Mutated library sequence

<400> SEQUENCE: 242

Gly Asn Tyr Leu Asp Tyr
1               5

<210> SEQ ID NO 243
<211> LENGTH: 6
<212> TYPE: PRT
<213> ORGANISM: Artificial Sequence
<220> FEATURE:
<223> OTHER INFORMATION: Mutated library sequence

<400> SEQUENCE: 243

Gly Pro Tyr Leu Asp Tyr
1               5

<210> SEQ ID NO 244
<211> LENGTH: 6
<212> TYPE: PRT
<213> ORGANISM: Artificial Sequence
<220> FEATURE:

<223> OTHER INFORMATION: Mutated library sequence

<400> SEQUENCE: 244

Gly Ser Tyr Leu Asp Tyr
1               5

<210> SEQ ID NO 245
<211> LENGTH: 12
<212> TYPE: PRT
<213> ORGANISM: Artificial Sequence
<220> FEATURE:
<223> OTHER INFORMATION: Mutated library sequence

<400> SEQUENCE: 245

Arg Ala Ser Gln Ser Val Ser Ser Asn Tyr Phe Gly
1               5                   10

<210> SEQ ID NO 246
<211> LENGTH: 7
<212> TYPE: PRT
<213> ORGANISM: Artificial Sequence
<220> FEATURE:
<223> OTHER INFORMATION: Mutated library sequence

<400> SEQUENCE: 246

Gly Ala Ser Ser Arg Ala Thr
1               5

<210> SEQ ID NO 247
<211> LENGTH: 9
<212> TYPE: PRT
<213> ORGANISM: Artificial Sequence
<220> FEATURE:
<223> OTHER INFORMATION: Mutated library sequence

<400> SEQUENCE: 247

Gln Gln Phe Asp Ser Leu Pro Leu Thr
1               5

<210> SEQ ID NO 248
<211> LENGTH: 9
<212> TYPE: PRT
<213> ORGANISM: Artificial Sequence
<220> FEATURE:
<223> OTHER INFORMATION: Mutated library sequence

<400> SEQUENCE: 248

Gln Gln His Asp Ser Ser Pro Leu Ser
1               5

<210> SEQ ID NO 249
<211> LENGTH: 9
<212> TYPE: PRT
<213> ORGANISM: Artificial Sequence
<220> FEATURE:
<223> OTHER INFORMATION: Mutated library sequence

<400> SEQUENCE: 249

Gln Gln Phe Asp Ser Ser Pro Leu Ser
1               5

<210> SEQ ID NO 250
<211> LENGTH: 9
<212> TYPE: PRT
<213> ORGANISM: Artificial Sequence
<220> FEATURE:
<223> OTHER INFORMATION: Mutated library sequence

```
<400> SEQUENCE: 250

Gln Gln Phe Asp Ser Ser Pro Leu Thr
1               5

<210> SEQ ID NO 251
<211> LENGTH: 5
<212> TYPE: PRT
<213> ORGANISM: Artificial Sequence
<220> FEATURE:
<223> OTHER INFORMATION: glycine serine linker

<400> SEQUENCE: 251

Gly Gly Gly Gly Ser
1               5

<210> SEQ ID NO 252
<211> LENGTH: 10
<212> TYPE: PRT
<213> ORGANISM: Artificial Sequence
<220> FEATURE:
<223> OTHER INFORMATION: glycine serine linker

<400> SEQUENCE: 252

Gly Gly Gly Gly Ser Gly Gly Gly Gly Ser
1               5                   10
```